United States Patent
Yakubov et al.

(10) Patent No.: US 11,497,708 B2
(45) Date of Patent: Nov. 15, 2022

(54) CUSTOMIZED COSMETIC COMPOSITIONS, AND METHODS OF REJUVENATING AND UTILIZING CONDITIONED MEDIA AND/OR COMPONENTS THEREOF

(71) Applicant: BEMY Cosmetics, Inc., Houston, TX (US)

(72) Inventors: Eduard Yakubov, Houston, TX (US); Yohannes Tsegai Ghebre, Houston, TX (US); Mark Christian Johnson, Houston, TX (US); Bradley Pylant, Houston, TX (US)

(73) Assignee: BEMY Cosmetics, Inc., Houston, TX (US)

( * ) Notice: Subject to any disclaimer, the term of this patent is extended or adjusted under 35 U.S.C. 154(b) by 0 days.

(21) Appl. No.: 15/624,047

(22) Filed: Jun. 15, 2017

(65) Prior Publication Data
US 2017/0360693 A1    Dec. 21, 2017

Related U.S. Application Data

(60) Provisional application No. 62/351,187, filed on Jun. 16, 2016.

(51) Int. Cl.
| | | |
|---|---|---|
| *A61K 8/98* | (2006.01) | |
| *G06Q 30/06* | (2012.01) | |
| *A61Q 19/00* | (2006.01) | |
| *A61Q 5/00* | (2006.01) | |
| *A61Q 19/08* | (2006.01) | |
| *A61K 31/7088* | (2006.01) | |

(52) U.S. Cl.
CPC .......... *A61K 8/981* (2013.01); *A61K 31/7088* (2013.01); *A61Q 5/00* (2013.01); *A61Q 19/00* (2013.01); *A61Q 19/08* (2013.01); *G06Q 30/0621* (2013.01)

(58) Field of Classification Search
CPC .................. A61K 31/7088; A61K 2300/00
See application file for complete search history.

(56) References Cited

U.S. PATENT DOCUMENTS

| | | | | |
|---|---|---|---|---|
| 8,025,907 B2 * | 9/2011 | Belfer | ............... | A61K 36/23 424/78.03 |
| 2004/0087016 A1 * | 5/2004 | Keating | ............. | A61K 38/1709 435/366 |
| 2009/0274770 A1 * | 11/2009 | Gammelsaeter | ....... | A61K 8/987 424/581 |
| 2011/0081402 A1 | 4/2011 | Kojima et al. | | |
| 2011/0171185 A1 * | 7/2011 | Klimanskaya | ....... | C12N 5/0696 424/93.21 |
| 2012/0141399 A1 | 6/2012 | You et al. | | |
| 2014/0066381 A1 * | 3/2014 | Dal Farra | ................ | C07K 7/06 514/18.8 |
| 2015/0299650 A1 | 10/2015 | Chuang et al. | | |
| 2018/0161373 A1 * | 6/2018 | Lunyak | ................ | G01N 33/574 |

FOREIGN PATENT DOCUMENTS

| | | |
|---|---|---|
| EP | 2 586 864 A1 | 5/2013 |
| FR | 2912916 A1 | 8/2008 |
| WO | WO-2007/070850 A2 | 6/2007 |
| WO | WO-2008/082524 A1 | 7/2008 |
| WO | WO-2012/135237 A2 | 10/2012 |
| WO | WO-2015/002892 A1 | 1/2015 |
| WO | WO-2015/095794 A1 | 6/2015 |

OTHER PUBLICATIONS

MiScript miRNA mimics, 2013, https://www.qiagen.com/us/products/discovery-and-translational-research/pcr-qpcr-dpcr/qpcr-assays-and-instruments/mirna-qpcr-assay-and-panels/miscript-mirna-mimics/, 6 pages (Year: 2013).*
Oct. 27, 2017 International Search Report and Written Opinion mailed in International Patent Application No. PCT/US17/37926, filed Jun. 16, 2017.
Jan. 22, 2020 Supplementary European Search Report and Search Opinion mailed in EP 17814193.3.

* cited by examiner

*Primary Examiner* — Kyle A Purdy
(74) *Attorney, Agent, or Firm* — Foley & Lardner LLP

(57) ABSTRACT

Cosmetic formulations and compositions customized and/or personalized for rejuvenation of skin and/or hair are described. The cosmetic formulations are customized and/or personalized to include an extract and/or one or more molecular components in amounts and ratios naturally produced by rejuvenated cells or by cells modified toward rejuvenation. These cells are of skin and/or hair origin that have been reprogrammed, in which the skin and/or hair cells, having been rejuvenated and/or modified from the original cell, are initially obtained from a subject for which a customized cosmetic composition is for, or from a subject representative of a person for which a customized cosmetic composition is for. Reprogramming of the skin and/or hair cells provide rejuvenated cells, embryonic stem cell-like pluripotent cells, and/or transdifferentiated or differentiated young or younger cells that have been transdifferentiated from the rejuvenated or modified cells or differentiated from the embryonic stem cell-like pluripotent cells. Methods of selecting, preparing, and formulating the customized cosmetic products are also described.

32 Claims, 8 Drawing Sheets
(2 of 8 Drawing Sheet(s) Filed in Color)

CUSTOMIZED COSMETIC COMPOSITIONS, AND METHODS OF REJUVENATING AND UTILIZING CONDITIONED MEDIA AND/OR COMPONENTS THEREOF

PRIOR RELATED APPLICATIONS

This application claims benefit of U.S. Provisional Patent Application No. 62/351,187 entitled "Customized Cosmetic Compositions, and Methods of Safely Rejuvenating and Utilizing Cells and/or Components Thereof,' filed on Jun. 16, 2016.

FEDERALLY SPONSORED RESEARCH STATEMENT

Not Applicable ("N/A")

Reference to Microfiche Appendix

N/A

FIELD OF INVENTION

The disclosed is related in general to cosmetic compositions formulated as skin or hair care products, and methods of preparing the cosmetic compositions.

BACKGROUND OF THE INVENTION

Without limiting the scope of the invention, its background is described in connection with providing one or more improved cosmetic compositions for skin and/or hair, in which each of the cosmetic compositions include novel formulations for rejuvenating the skin and/or hair that is characterized by having or having had, or experiencing or having experienced, one or more hair and/or skin cosmetic, morphological, functional, molecular, cellular, extracellular, or tissue changes commonly associated with aging.

Heretofore, while certain products for skin and/or hair profess to be suitable for use on the skin and/or hair, respectively, there remains little evidence that most of such products are capable of providing individualized needs of the skin and/or hair, or that such products provide rejuvenation based on individual needs of the skin and/or hair. These and other needs are addressed by the rejuvenating cosmetic compositions and formulations described below.

SUMMARY OF THE INVENTION

Described herein are rejuvenating cosmetic compositions formulated as skin care products for the skin, and methods of preparing the rejuvenating cosmetic compositions, in which such cosmetic compositions may be custom formulated for personalized needs of the programmable skin rejuvenation. As used herein, one or more of the rejuvenating cosmetic compositions may be for dermatologic use, such as when formulated as such.

Described herein are cosmetic rejuvenating compositions formulated as hair care products for the hair, and methods of preparing the cosmetic rejuvenating compositions, in which the cosmetic compositions may be custom formulated for personalized needs of the programmable hair rejuvenation.

In one or more embodiments, customization includes initially rejuvenating cells, the cells being skin and/or hair cells of a subject, meaning a person or an animal, in need of rejuvenation of the skin and/or hair, or from a subject representative of a subject in need of rejuvenation of the skin and/or hair. Without limiting the scope of the invention, examples of ways in which one subject might be representative of another subject, include having similar genetic background, SNP profile, telomere length, gene expression profile in one or more specific cell types, skin appearance, hair appearance, gender, age, ethnicity, lifestyle, blood type, profession, height, weight, elements of medical history, etc. Rejuvenating such cells involves one of the following: (i) direct rejuvenation of such cells via overexpression of one or more genes encoding for human telomerase reverse transcriptase (hTERT) [from the group comprising a wild type catalytic subunit and/or its catalytically more powerful mutants], a human shelterin complex component [from the group comprising RAP1, TIN2, TRF1, TRF2, TPP1, POT1], and a human aging/longevity regulating proteins [from the group of SIRT proteins (e.g., SIRT-1, SIRT-2, SIRT-3, SIRT-4, SIRT-5, SIRT-6, SIRT-7), transcription factor JunD (JunD), growth differentiation factor 11 (GDF11), etc.] to form rejuvenated cells; (ii) induction of pluripotency via introduction of pluripotency-associated RNA transcripts, with or without cocktail of small molecules, to form rejuvenated cells representative of induced pluripotent stem cells (iPSCs); (iii) direct differentiation (trans-differentiation, or expression/overexpression process) of the rejuvenated cells obtained in (i) to form differentiated young or younger cells; and (iv) differentiation of the rejuvenated cells obtained in (ii) to form another kind of differentiated young or younger cells representative of differentiated iPSCs. Accordingly, customization of one or more rejuvenating formulations and/or compositions as described herein includes rejuvenating cells, and including at least some of the rejuvenating cells, and/or components thereof, and/or by-products thereof in the rejuvenating formulations and/or compositions.

In one or more embodiments, rejuvenated cells are prepared by providing a plurality of messenger RNA (mRNA) mimetics, with or without a cocktail of small molecules, to a sample, including cells, and in a suitable setting and/or environment, the sample and/or cells thereof are then conditioned to a conditioned or rejuvenated state, and when so conditioned and/or rejuvenated are suitable for further utilization in and/or for providing at least some of the cosmetic composition described herein.

In one or more embodiments, the plurality of mRNA mimetics may encode pluripotency-associated transcripts, with or without cocktail of small molecules, and are provided to a sample containing cells, the sample obtained from a subject for which a customized formulation will be provided to and/or representative of a subject for which a customized formulation will be provided to. The pluripotency-associated transcripts encode a suitable combination of Yamanaka and Thomson transcription factors, or at least some Yamanaka and Thomson transcription factors, or suitable alternatives thereof, such as suitable alternatives as is understood in the relevant field to the ordinary skilled artisan, that together induce the cells of the sample to pluripotency. Such mRNA mimetics are provided to the sample containing cells in a suitable setting and/or environment understood in the relevant art, to provide a conditioned or rejuvenated state, in which the conditioned or rejuvenated state includes rejuvenated cells, the rejuvenated cells being RNA-induced pluripotent stem cells (RiPSCs), or induced pluripotent embryonic-like stem cells (iPSCs).

In one or more embodiments, the plurality of mRNA mimetics may encode a hTERT, or a protein that is synergistic to hTERT (e.g., one or more shelterin complex proteins), or possesses hTERT catalytic or enzymatic activity, or a protein that activates endogenous hTERT catalytic or enzymatic activity, or a protein that activates endogenous hTERT expression, or a protein that regulates cell aging and longevity (e.g., one or more SIRT proteins, JunD, GDF11, etc.). Such mRNA mimetics are provided to a sample containing cells, the sample obtained from a subject for which a customized formulation will be provided to and/or representative of a subject for which a customized formulation will be provided to. In one or more embodiments, such mRNA mimetics for hTERT and/or shelterin complex proteins (or activators thereof) are provided to the sample containing cells in a suitable setting and/or environment understood in the relevant art, to provide a conditioned or rejuvenated state, in which the conditioned or rejuvenated state includes rejuvenated cells, the rejuvenated cells being RNA-induced rejuvenated cells that represent cells with increased telomerase length to enhance replicative capacity and/or decrease senescence. In one or more embodiments, mRNA mimetics for one or more proteins regulating cell aging and longevity (e.g. SIRTs, JunD, GDF11, etc.) provide cells in a conditioned or rejuvenated state, in which the conditioned or rejuvenated state includes rejuvenated cells, the rejuvenated cells being RNA-induced rejuvenated cells that represent cells with improved metabolism and mitochondrial function. In one or more embodiments, the mRNA mimetics may encode any such proteins described herein having an effect (including any combination having a synergistic effect) on cell rejuvenation as may be evaluated by exhibiting an improvement in replicative capacity and/or a decrease in stress-induced premature senescent markers (as compared with cells that have not been conditioned with the mRNA mimetics that encode the proteins described herein).

In one or more embodiments, upon providing the rejuvenated cells in any manner described herein, such rejuvenated cells may undergo differentiation to form differentiated young or younger cells. For example, rejuvenated cells that were rejuvenated by being conditioned with any of the described mRNA mimetics may be induced to undergo differentiation. Here, differentiation is provided by introducing lineage specific mRNA mimetics, which induces direct differentiation of the rejuvenated cells of (i), or transdifferentiation of the rejuvenated cells of (ii), forming differentiated young or younger cells, such that the lineage specific mRNA mimetics differ from the mRNA mimetics utilized for conditioning and forming the rejuvenated cells. The differentiated young or younger cells may be in the form of keratinocytes or keratinocyte-like cells, or in the form of melanocytes or melanocyte-like cells, or in the form of other skin cell types. The differentiated young or younger cells in the form of keratinocytes or keratinocyte-like cells may undergo differentiation by conditioning the rejuvenated cells with keratinocyte-specific mRNA mimetics. The differentiated young or younger cells in the form of melanocytes or melanocyte-like cells may undergo differentiation by conditioning the rejuvenated cells with melanocyte-specific mRNA mimetics. The differentiated young or younger cells in the form of other skin cells types may undergo differentiation by conditioning the rejuvenated cells with said skin cell type-specific mRNA mimetics. In one or more embodiments, additional rounds of rejuvenation may be applied to the differentiating cells before, during or after differentiation.

In one or more embodiments, the sample, including cells, is or includes a sample from hair and/or skin of a subject. The subject may be a donor. The subject may be an individual or customer having personalized needs. In one or more embodiments, the sample, including cells, from the subject or a representative of the subject is an original sample and/or includes original cells from the subject or a representative of the subject. In one or more embodiments, the sample, including cells, from the subject or a representative of the subject may be an original sample and/or original cells obtained from hair and/or skin of the subject for which at least one cosmetic composition is to be provided to. In one or more embodiments, the sample, including cells, may be an original sample and/or original cells obtained from hair and/or skin of a subject representative of but not the same as a subject for which at least one cosmetic composition is to be provided to. The sample containing cells and/or the original cells may be or may include fibroblasts. The sample containing cells and/or the original cells may be or may include keratinocytes. The sample containing cells and/or the original cells may be or may include melanocytes.

In one or more embodiments, rejuvenating cosmetic compositions and formulations described herein will include an extract obtained from rejuvenated cells and/or one or more select components thereof, in which the rejuvenated cells are rejuvenated from original cells in any manner described herein. The extract may comprise a whole cell extract. The extract may comprise an enriched extract by charge, size, shape, molecular weight and/or any other specification, enriched with one or more of the components of the rejuvenated cells (e.g. peptides, proteins, endogenous mRNA, endogenous microRNA (miRNA), exosomes and/or cargo thereof, carbohydrates, polysaccharides, proteoglycans, sugars, metabolites, lipids, prohormones, hormones, fatty acids, vitamins, metals, ions, co-factors, small molecules, as representative examples). The extract may comprise all or one or more select components synthesized by the rejuvenated cells. The extract may be comprised of components that are intracellular, membrane bound, or secreted, or a combination thereof. The original cells may be obtained from a sample of skin and/or hair of a subject for which at least one of the rejuvenating cosmetic compositions is to be provided to. The original cells may be obtained from a sample of hair and/or skin of a subject representative of (but not the same as) a subject for which at least one of the rejuvenating cosmetic composition is to be provided to.

In some embodiments, when the sample and/or cells thereof are so-conditioned or rejuvenated, the so-conditioned or rejuvenated sample and/or cells are differentiated to provide an extract and/or one or more components from the differentiated cells to at least one rejuvenating cosmetic compositions and/or formulation thereof.

In one or more embodiments, rejuvenating cosmetic compositions and formulations described herein will include an extract obtained from rejuvenated cells and/or one or more select components thereof, in which the rejuvenated cells have differentiated (into young or younger cells), and in which the rejuvenated cells (prior to, during, or after differentiation) are rejuvenated from original cells in any manner described herein. The original cells may be obtained from a sample of skin and/or hair of a subject for which at least one of the rejuvenating cosmetic compositions is to be provided to. The original cells may be obtained from a sample of hair and/or skin of a subject representative of (but not the same as) a subject for which at least one of the rejuvenating cosmetic composition is to be provided to. The differentiated young or younger cells may be keratinocytes, fibroblasts, melanocytes, squamous cells, Merkel cells, Langerhans cells, immune cells, endocrine cells, endothelial cells, and/or cells characterized as and/or resembling one or more of these cell types, or another cell type that affects skin form or function. The differentiated young or younger cells may be other skin cells, and/or cells characterized as and/or resembling other skin cells. In one or more embodiments, the differentiated young or younger cells may be used as substrates for preparation of extracts, and such extracts may be included in at least one of the rejuvenating cosmetic compositions described herein. The extract may comprise a whole cell extract. The extract may comprise an enriched extract, enriched with one or more of the components, on the basis of charge, size, shape, molecular weight and/or any other specification, of the differentiated cells or the components secreted by the differentiated cells. The extract may comprise all or one or more select components synthesized and/or released by the differentiated young or younger cells.

In one or more embodiments, the rejuvenating cosmetic compositions described herein or formulations thereof will include at least one or more of the following from the rejuvenated cells or cell culture media in which the cells have been cultured, rejuvenated in any manner as described herein: (i) a whole cell extract; (ii) an enriched cell extract; (iii) an extract representing one or more of, or a pool of, proteins and/or peptides; (iv) an extract representing one or more of, or a pool of, endogenous mRNA; (v) an extract representing one or more of, or a pool of, endogenous microRNA (miRNA); (vi) an extract representing one or more of, or a pool of, endogenous exosomes (and/or their cargo); (vii) an extract representing one or more of, or a pool of, small molecules; (viii) an extract representing one or more of, or a pool of, metabolites; (ix) an extract representing one or more of, or a pool of, carbohydrates; (x) an extract representing one or more of, or a pool of, lipids; (xi) an extract representing one or more of, or a pool of, fatty acids; (xii) an extract representing one or more of, or a pool of, vitamins; (xiii) an extract representing one or more of, or a pool of, metals; (xiv) an extract representing one or more of, or a pool of, ions; (xv) an extract representing one or more of, or a pool of, co-factors; (xvi) an extract representing one or more of, or a pool of, prohormones; (xvii) an extract representing one or more of, or a pool of, hormones; and (xviii) an extract representing a combination of one or more of the aforementioned components.

In one or more embodiments, the rejuvenating cosmetic compositions described herein or formulations thereof will include at least one or more of the following from the differentiated young or younger cells or conditioned media in which the cells are cultured, differentiated in any manner as described herein: (i) an extract representing one or more of, or a pool of, proteins and/or peptides; (ii) a whole cell extract; (iii) an enriched cell extract; (iv) an extract representing one or more of, or a pool of, endogenous mRNA; (v) an extract representing one or more of, or a pool of, endogenous micro RNA (miRNA); (vi) an extract representing one or more of, or a pool of, endogenous exosomes (and/or their cargo); (vii) an extract representing one or more of, or a pool of, small molecules; (viii) an extract representing one or more of, or a pool of, metabolites; (ix) an extract representing one or more of, or a pool of, carbohydrates; (x) an extract representing one or more of, or a pool of, lipids; (xi) an extract representing one or more of, or a pool of, fatty acids; (xii) an extract representing one or more of, or a pool of, vitamins; (xiii) an extract representing one or more of, or a pool of, metals; (xiv) an extract representing one or more of, or a pool of, ions; (xv) an extract representing one or more of, or a pool of, co-factors; (xvi) an extract representing one or more of, or a pool of, prohormones; (xvii) an extract representing one or more of, or a pool of, hormones; and (xviii) an extract representing a combination of one or more of the aforementioned components.

In one or more embodiments, the rejuvenating cosmetic compositions described herein or formulations thereof will include at least one or more of a mixture representing one or more or a pool of biologically active rejuvenating components (e.g., biopolymers as RNA, biopolymers as proteins and/or peptides, and/or exosomes, and/or cargo of exosomes, lipids, fatty acids, metabolites, metals, prohormones, hormones, vitamins, ions, co-factors, small molecules, or variations thereof). In some embodiments, the mixture representing one or more or a pool of biologically active rejuvenating components may be selected based on an environment of a sample (e.g., in which the sample comprises skin and/or hair of a subject for which the cosmetic composition is to be provided to, and/or is a representative sample comprising skin and/or hair representative of the subject for which the cosmetic composition is to be provided to). In some embodiments, the mixture representing one or more or a pool of biologically active rejuvenating molecules may be selected based on lifestyle habits associated with the sample (e.g., in which the sample comprises skin and/or hair of a subject for which the cosmetic composition is to be provided to, and/or is a representative sample comprising skin and/or hair representative of the subject for which the cosmetic composition is to be provided to). In one or more embodiments, the mixture representing one or more or a pool of biologically active rejuvenating components may be obtained and/or identified and/or selected for after performing an analysis of the rejuvenated cells (rejuvenated in any manner as described herein, and rejuvenated from a sample comprising skin and/or hair of a subject for which the cosmetic composition is to be provided to, and/or from a representative sample comprising skin and/or hair representative of the subject for which the cosmetic composition is to be provided to). In one or more embodiments, the mixture representing one or more or a pool of biologically active rejuvenating components may be obtained and/or identified and/or selected for after comparing rejuvenated cells and/or their components with original sample cells, in which the rejuvenated cells are rejuvenated in any manner as described herein, and are rejuvenated from a sample comprising skin and/or hair of a subject for which the cosmetic composition is to be provided to, and/or from a representative sample comprising skin and/or hair representative of the subject for which the cosmetic composition is to be provided to, and in which the original cells are from the sample comprising skin and/or hair of the subject for which the cosmetic composition is to be provided to, and/or from a representative sample comprising skin and/or hair representative of the subject for which the cosmetic composition is to be provided to. In one or more embodiments, the mixture representing one or more or a pool of biologically active rejuvenating components may be obtained and/or identified and/or selected for after comparing differentiated young or younger cells and/or their components against original sample cells or against cell types that were not subjected to rejuvenation as described herein (e.g., differentiated young or younger keratinocytes or differentiated young or younger keratinocyte-like cells compared against a known keratinocyte cell line or keratinocytes obtained from the sample and/or the subject). Here, the differentiated young or younger cells have differentiated from rejuvenated cells, rejuvenated and differentiated in any manner as described herein, and the rejuvenated cells are rejuvenated from a sample comprising skin and/or hair of a subject for which the cosmetic composition is to be provided to, and/or from a representative sample comprising skin and/or hair representative of the subject for which the cosmetic composition is to be provided to, and in which the original cells are from the sample comprising skin and/or hair of the subject for which the cosmetic composition is to be provided to, and/or from a representative sample comprising skin and/or hair representative of the subject for which the cosmetic composition is to be provided to.

In one or more embodiments, the rejuvenating cosmetic compositions described herein or formulations thereof will also include one or more or a plurality of small molecules. In some embodiments, the one or more or a plurality of small molecules may be selected based on an environment of a sample (e.g., in which the sample comprises skin and/or hair of a subject for which the cosmetic composition is to be provided to, and/or is a representative sample comprising skin and/or hair representative of the subject for which the cosmetic composition is to be provided to). In some embodiments, the one or more or a plurality of small molecules may be selected based on lifestyle habits associated with the sample (e.g., in which the sample comprises skin and/or hair of a subject for which the cosmetic composition is to be provided to, and/or is a representative sample comprising skin and/or hair representative of the subject for which the cosmetic composition is to be provided to). In one or more embodiments, the one or more or a plurality of small molecules may be obtained and/or identified and/or selected for after performing an analysis of the rejuvenated cells (rejuvenated in any manner as described herein, and rejuvenated from a sample comprising skin and/or hair of a subject for which the cosmetic composition is to be provided to, and/or from a representative sample comprising skin and/or hair representative of the subject for which the cosmetic composition is to be provided to). In one or more embodiments, the one or more or a plurality of small molecules may be obtained and/or identified and/or selected for after comparing rejuvenated cells and/or their components with original sample cells, in which the rejuvenated cells are rejuvenated in any manner as described herein, and are rejuvenated from a sample comprising skin and/or hair of a subject for which the cosmetic composition is to be provided to, and/or from a representative sample comprising skin and/or hair representative of the subject for which the cosmetic composition is to be provided to, and in which the original cells are from the sample comprising skin and/or hair of the subject for which the cosmetic composition is to be provided to, and/or from a representative sample comprising skin and/or hair representative of the subject for which the cosmetic composition is to be provided to. In one or more embodiments, the one or more or a plurality of small molecules may be obtained and/or identified and/or selected for after comparing differentiated young or younger cells and/or their components against original sample cells or against cell types that were not subjected to rejuvenation in any manner as described herein (e.g., differentiated young or younger keratinocytes or differentiated young or younger keratinocyte-like cells compared against a known keratinocyte cell line or keratinocytes obtained from the sample and/or the subject). The differentiated young or younger cells have differentiated from rejuvenated cells in any manner described herein. The rejuvenated cells are rejuvenated from a sample comprising skin and/or hair of a subject for which the cosmetic composition is to be provided to, and/or from a representative sample comprising skin and/or hair representative of the subject for which the cosmetic composition is to be provided to, and in which the original cells are from the sample comprising skin and/or hair of the subject for which the cosmetic composition is to be provided to, and/or from a representative sample comprising skin and/or hair representative of the subject for which the cosmetic composition is to be provided to.

In one or more embodiments, the rejuvenating cosmetic compositions described herein or formulations thereof will include one or more proteins (e.g., recombinant proteins and/or proteins rejuvenating skin, such as hTERT, SIRTs, JunD, GDF11, etc.) associated with skin (e.g., collagen, elastin, fibronectin, keratin, filaggrin, corneodesmosin, laminin, etc.) and/or one or more mRNA mimetics encoding one or more of such proteins. These one or more proteins and/or the mRNA mimetics may be selected based on an environment of a sample (e.g., in which the sample comprises skin and/or hair of a subject for which the cosmetic composition is to be provided to, and/or is a representative sample comprising skin and/or hair representative of the subject for which the cosmetic composition is to be provided to). In some embodiments, these one or more proteins and/or mRNA mimetics may be selected based on lifestyle habits associated with the sample (e.g., in which the sample comprises skin and/or hair of a subject for which the cosmetic composition is to be provided to, and/or is a representative sample comprising skin and/or hair representative of the subject for which the cosmetic composition is to be provided to). In one or more embodiments, these one or more proteins and/or mRNA mimetics may be obtained and/or identified and/or selected for after performing an analysis of the rejuvenated cells (rejuvenated in any manner as described herein, and rejuvenated from a sample comprising skin and/or hair of a subject for which the cosmetic composition is to be provided to, and/or from a representative sample comprising skin and/or hair representative of the subject for which the cosmetic composition is to be provided to). In one or more embodiments, these one or more proteins and/or mRNA mimetics may be obtained and/or identified and/or selected for after comparing rejuvenated cells and/or their components with original sample cells, in which the rejuvenated cells are rejuvenated in any manner as described herein, and are rejuvenated from a sample comprising skin and/or hair of a subject for which the cosmetic composition is to be provided to, and/or from a representative sample comprising skin and/or hair representative of the subject for which the cosmetic composition is to be provided to, and in which the original cells are from the sample comprising skin and/or hair of the subject for which the cosmetic composition is to be provided to, and/or from a representative sample comprising skin and/or hair representative of the subject for which the cosmetic composition is to be provided to. In one or more embodiments, the one or more proteins associated with skin may be obtained and/or identified and/or selected for after comparing differentiated young or younger cells and/or their components against original sample cells or against cell types that were not subjected to rejuvenation in any manner as described herein (e.g., differentiated young or younger keratinocytes or differentiated young or younger keratinocyte-like cells compared against a known keratinocyte cell line or keratinocytes obtained from the sample and/or the subject). The differentiated young or younger cells have differentiated from rejuvenated cells in any manner described herein. The rejuvenated cells are rejuvenated from a sample comprising skin and/or hair of a subject for which the cosmetic composition is to be provided to, and/or from a representative sample comprising skin and/or hair representative of the subject for which the cosmetic composition is to be provided to, and in which the original cells are from the sample comprising skin and/or hair of the subject for which the cosmetic composition is to be provided to, and/or from a representative sample comprising skin and/or hair representative of the subject for which the cosmetic composition is to be provided to.

In one or more embodiments, the rejuvenating cosmetic compositions described herein or formulations thereof will also include one or more of a telomerase activator, and/or inflammatory pathway factor repressor (e.g., repressors of nuclear factor kappa B, and/or chromatin modifying enzymes, such as SIRT family histone deacetylases). Such telomerase activators and/or inflammatory pathway factor repressors and/or chromatin modifying enzymes may be used independently on exogenously expressed telomerase, and/or to enhance rejuvenation provided by exogenously expressed telomerase. In one or more embodiments, the telomerase activators and/or inflammatory pathway factor repressors and/or chromatin modifying enzymes may be obtained and/or identified and/or selected for after performing an analysis of the rejuvenated cells (rejuvenated in any manner as described herein, and rejuvenated from a sample comprising skin and/or hair of a subject for which the cosmetic composition is to be provided to, and/or from a representative sample comprising skin and/or hair representative of the subject for which the cosmetic composition is to be provided to). In one or more embodiments, the telomerase activators and/or inflammatory pathway factor repressors and/or chromatin modifying enzymes may be obtained and/or identified and/or selected for after comparing rejuvenated cells and/or their components with original sample cells, in which the rejuvenated cells are rejuvenated in any manner as described herein, and are rejuvenated from a sample comprising skin and/or hair of a subject for which the cosmetic composition is to be provided to, and/or from a representative sample comprising skin and/or hair representative of the subject for which the cosmetic composition is to be provided to, and in which the original cells are from the sample comprising skin and/or hair of the subject for which the cosmetic composition is to be provided to, and/or from a representative sample comprising skin and/or hair representative of the subject for which the cosmetic composition is to be provided to. In one or more embodiments, the telomerase activators and/or inflammatory pathway factor repressors and/or chromatin modifying enzymes may be obtained and/or identified and/or selected for after comparing differentiated young or younger cells and/or their components against original sample cells or against cell types that were not subjected to rejuvenation in any manner as described herein (e.g., differentiated young or younger keratinocytes or differentiated young or younger keratinocyte-like cells compared against a known keratinocyte cell line or keratinocytes obtained from the sample and/or the subject). The differentiated young or younger cells have differentiated from rejuvenated cells in any manner described herein. The rejuvenated cells are rejuvenated from a sample comprising skin and/or hair representative of the subject for which the cosmetic composition is to be provided to, and in which the original cells are from the sample comprising skin and/or hair of the subject for which the cosmetic composition is to be provided to, and/or from a representative sample comprising skin and/or hair representative of the subject for which the cosmetic composition is to be provided to.

In one or more embodiments, the rejuvenating cosmetic compositions described herein or formulations thereof will include one or more small or microRNA (miRNA) [e.g., conserved non-coding small RNAs of about 10 to about 150 nucleotides, such as miRNA 10(a), miRNA 21(-3p, -5p), miRNA-29, miRNA-146(a), miRNA-155(-3p, -5p)], and/or anti-inflammatory miRNA, and/or an inhibitor of a pro-inflammatory miRNA, and various combinations thereof. An example of an inhibitor of an miRNA would be a nucleic acid with a sequence that is complementary to the target miRNA. The antagonists and/or inhibitors may be used to disrupt the otherwise pro-inflammatory action of one or more miRNA (e.g., miRNA identified in original cells of a sample obtained from a subject for which the cosmetic composition is to be provided to, and/or in original cells of a sample representative of a sample of a subject for which the cosmetic composition is to be provided to). In one or more embodiments, some or all of the miRNAs, as rejuvenating miRNA, are obtained and/or identified and/or selected for after performing an analysis of the rejuvenated cells (rejuvenated in any manner as described herein, and rejuvenated from a sample comprising skin and/or hair of a subject for which the cosmetic composition is to be provided to, and/or from a representative sample comprising skin and/or hair representative of the subject for which the cosmetic composition is to be provided to). In one or more embodiments, some or all of the miRNAs, as rejuvenating miRNA, are obtained and/or identified and/or selected for after comparing rejuvenated cells and/or their components with original sample cells, in which the rejuvenated cells are rejuvenated in any manner as described herein, and are rejuvenated from a sample comprising skin and/or hair of a subject for which the cosmetic composition is to be provided to, and/or from a representative sample comprising skin and/or hair representative of the subject for which the cosmetic composition is to be provided to, and in which the original cells are from the sample comprising skin and/or hair of the subject for which the cosmetic composition is to be provided to, and/or from a representative sample comprising skin and/or hair representative of the subject for which the cosmetic composition is to be provided to. In one or more embodiments, some or all of the miRNAs, as rejuvenating miRNA, are obtained and/or identified and/or selected for after comparing differentiated young or younger cells and/or their components against original sample cells or against cell types that were not subjected to rejuvenation in any manner as described herein (e.g., differentiated young or younger keratinocytes or differentiated young or younger keratinocyte-like cells compared against a known keratinocyte cell line or keratinocytes obtained from the sample and/or the subject). The differentiated young or younger cells have differentiated from rejuvenated cells in any manner described herein. The rejuvenated cells are rejuvenated from a sample comprising skin and/or hair of a subject for which the cosmetic composition is to be provided to, and/or from a representative sample comprising skin and/or hair representative of the subject for which the cosmetic composition is to be provided to, and in which the original cells are from the sample comprising skin and/or hair of the subject for which the cosmetic composition is to be provided to, and/or from a representative sample comprising skin and/or hair representative of the subject for which the cosmetic composition is to be provided to. Similarly, anti-inflammatory miRNA, and/or an inhibitor of a pro-inflammatory miRNA, and various combinations thereof may be obtained and/or identified and/or selected for in any of the embodiments described with the miRNAs that are considered rejuvenating miRNA.

In one or more embodiments, the rejuvenating cosmetic compositions described herein or formulations thereof will include one or more recombinant proteins (e.g., such as the one or more proteins described above) and/or mRNA mimetics, which are further combined with one or more anti-inflammatory miRNA and/or one or more inhibitors of pro-inflammatory miRNA as described above. Said combination provides a synergistic effect having anti-aging effects. Said synergistic combination, in one or more embodiments, may be obtained and/or identified and/or selected for after performing an analysis of the rejuvenated cells (rejuvenated in any manner as described herein, and rejuvenated from a sample comprising skin and/or hair of a subject for which the cosmetic composition is to be provided to, and/or from a representative sample comprising skin and/or hair representative of the subject for which the cosmetic composition is to be provided to). In one or more embodiments, some or all of such a synergistic combination may be obtained and/or identified and/or selected for after comparing rejuvenated cells and/or their components with original sample cells, in which the rejuvenated cells are rejuvenated in any manner as described herein, and are rejuvenated from a sample comprising skin and/or hair of a subject for which the cosmetic composition is to be provided to, and/or from a representative sample comprising skin and/or hair representative of the subject for which the cosmetic composition is to be provided to, and in which the original cells are from the sample comprising skin and/or hair of the subject for which the cosmetic composition is to be provided to, and/or from a representative sample comprising skin and/or hair representative of the subject for which the cosmetic composition is to be provided to. In one or more embodiments, some or all of the synergistic combination, as a synergistic rejuvenating combination, may be obtained and/or identified and/or selected for after comparing differentiated young or younger cells and/or their components against original sample cells or against cell types that were not subjected to rejuvenation in any manner as described herein (e.g., differentiated young or younger keratinocytes or differentiated young or younger keratinocyte-like cells compared against a known keratinocyte cell line or keratinocytes obtained from the sample and/or the subject). The differentiated young or younger cells have differentiated from rejuvenated cells in any manner described herein. The rejuvenated cells are rejuvenated from a sample comprising skin and/or hair of a subject for which the cosmetic composition is to be provided to, and/or from a representative sample comprising skin and/or hair representative of the subject for which the cosmetic composition is to be provided to, and in which the original cells are from the sample comprising skin and/or hair of the subject for which the cosmetic composition is to be provided to, and/or from a representative sample comprising skin and/or hair representative of the subject for which the cosmetic composition is to be provided to.

In one or more embodiments, the rejuvenating cosmetic compositions described herein or formulations thereof will include one or more short interfering RNA (siRNA) (e.g., short RNAs that inhibit expression of a target endogenous mRNA transcript). These siRNAs may be used to disrupt and/or silence expression of one or more target transcripts. In one or more embodiments, the siRNA are identified and/or selected for after an induction process utilizing pluripotency-associated transcripts provided to a sample containing cells. In one or more embodiments, some or all of the siRNAs, as inhibitors of expression of one or more target transcripts, are obtained and/or identified and/or selected for after performing an analysis of the rejuvenated cells (rejuvenated in any manner as described herein, and rejuvenated from a sample comprising skin and/or hair of a subject for which the cosmetic composition is to be provided to, and/or from a representative sample comprising skin and/or hair representative of the subject for which the cosmetic composition is to be provided to). In one or more embodiments, some or all of the siRNAs are obtained and/or identified and/or selected for after comparing rejuvenated cells and/or their components with original sample cells, in which the rejuvenated cells are rejuvenated in any manner as described herein, and are rejuvenated from a sample comprising skin and/or hair of a subject for which the cosmetic composition is to be provided to, and/or from a representative sample comprising skin and/or hair representative of the subject for which the cosmetic composition is to be provided to, and in which the original cells are from the sample comprising skin and/or hair of the subject for which the cosmetic composition is to be provided to, and/or from a representative sample comprising skin and/or hair representative of the subject for which the cosmetic composition is to be provided to. In one or more embodiments, some or all of the siRNAs are obtained and/or identified and/or selected for after comparing differentiated young or younger cells and/or their components against original sample cells or against cell types that were not subjected to rejuvenation in any manner as described herein (e.g., differentiated young or younger keratinocytes or differentiated young or younger keratinocyte-like cells compared against a known keratinocyte cell line or keratinocytes obtained from the sample and/or the subject). The differentiated young or younger cells have differentiated from rejuvenated cells in any manner described herein. The rejuvenated cells are rejuvenated from a sample comprising skin and/or hair of a subject for which the cosmetic composition is to be provided to, and/or from a representative sample comprising skin and/or hair of a subject for which the cosmetic composition is to be provided to, and/or from a representative sample comprising skin and/or hair representative of the subject for which the cosmetic composition is to be provided to, and in which the original cells are from the sample comprising skin and/or hair of the subject for which the cosmetic composition is to be provided to, and/or from a representative sample comprising skin and/or hair representative of the subject for which the cosmetic composition is to be provided to.

In one or more embodiments, the rejuvenating cosmetic compositions described herein or formulations thereof will include one or more recombinant proteins (e.g., such as the one or more proteins described above) and/or mRNA mimetics to upregulate one or more anti-aging proteins as described above, which are further combined with one or more siRNA and/or an siRNA cocktail as described above, the siRNA (or cocktail thereof) being used to disrupt and/or silence expression of one or more proteins associated with aging. Said combination provides a synergistic effect having anti-aging effects. Said synergistic combination, in one or more embodiments, may be obtained and/or identified and/or selected for after performing an analysis of the rejuvenated cells (rejuvenated in any manner as described herein, and rejuvenated from a sample comprising skin and/or hair of a subject for which the cosmetic composition is to be provided to, and/or from a representative sample comprising skin and/or hair representative of the subject for which the cosmetic composition is to be provided to). In one or more embodiments, some or all of such a synergistic combination may be obtained and/or identified and/or selected for after comparing rejuvenated cells and/or their components with original sample cells, in which the rejuvenated cells are rejuvenated in any manner as described herein, and are rejuvenated from a sample comprising skin and/or hair of a subject for which the cosmetic composition is to be provided to, and/or from a representative sample comprising skin and/or hair representative of the subject for which the cosmetic composition is to be provided to, and in which the original cells are from the sample comprising skin and/or hair of the subject for which the cosmetic composition is to be provided to, and/or from a representative sample comprising skin and/or hair representative of the subject for which the cosmetic composition is to be provided to. In one or more embodiments, some or all of the synergistic combination, as a synergistic rejuvenating combination, may be obtained and/or identified and/or selected for after comparing differentiated young or younger cells and/or their components against original sample cells or against cell types that were not subjected to rejuvenation in any manner as described herein (e.g., differentiated young or younger keratinocytes or differentiated young or younger keratinocyte-like cells compared against a known keratinocyte cell line or keratinocytes obtained from the sample and/or the subject). The differentiated young or younger cells have differentiated from rejuvenated cells in any manner described herein. The rejuvenated cells are rejuvenated from a sample comprising skin and/or hair of a subject for which the cosmetic composition is to be provided to, and/or from a representative sample comprising skin and/or hair representative of the subject for which the cosmetic composition is to be provided to, and in which the original cells are from the sample comprising skin and/or hair of the subject for which the cosmetic composition is to be provided to, and/or from a representative sample comprising skin and/or hair representative of the subject for which the cosmetic composition is to be provided to.

In one or more embodiments, the rejuvenating cosmetic compositions described herein or formulations thereof will include long non-coding RNA (long ncRNA) mimetics (e.g., non-protein coding RNAs that are generally longer than 200 nucleotides, and do not encode mRNA, rRNA, or tRNA). The long ncRNA may be ones that serve as a platform when assembling one or more RNA-protein complexes, or assists when recruiting and/or finding the RNA-protein complex, and/or binds to and sequesters one or more regulatory proteins away from the DNA target. In one or more embodiments, some or all of the long ncRNA are obtained and/or identified and/or selected for after performing an analysis of the rejuvenated cells (rejuvenated in any manner as described herein, and rejuvenated from a sample comprising skin and/or hair of a subject for which the cosmetic composition is to be provided to, and/or from a representative sample comprising skin and/or hair representative of the subject for which the cosmetic composition is to be provided to). In one or more embodiments, some or all of the long ncRNA are obtained and/or identified and/or selected for after comparing rejuvenated cells and/or their components with original sample cells, in which the rejuvenated cells are rejuvenated in any manner as described herein, and are rejuvenated from a sample comprising skin and/or hair of a subject for which the cosmetic composition is to be provided to, and/or from a representative sample comprising skin and/or hair representative of the subject for which the cosmetic composition is to be provided to, and in which the original cells are from the sample comprising skin and/or hair of the subject for which the cosmetic composition is to be provided to, and/or from a representative sample comprising skin and/or hair representative of the subject for which the cosmetic composition is to be provided to. In one or more embodiments, some or all of the long ncRNA are obtained and/or identified and/or selected for after comparing differentiated young or younger cells and/or their components against original sample cells or against cell types that were not subjected to rejuvenation in any manner as described herein (e.g., differentiated young or younger keratinocytes or differentiated young or younger keratinocyte-like cells compared against a known keratinocyte cell line or keratinocytes obtained from the sample and/or the subject). The differentiated young or younger cells have differentiated from rejuvenated cells in any manner described herein. The rejuvenated cells are rejuvenated from a sample comprising skin and/or hair of a subject for which the cosmetic composition is to be provided to, and/or from a representative sample comprising skin and/or hair of a subject for which the cosmetic composition is to be provided to, and/or from a representative sample comprising skin and/or hair representative of the subject for which the cosmetic composition is to be provided to, and in which the original cells are from the sample comprising skin and/or hair of the subject for which the cosmetic composition is to be provided to, and/or from a representative sample comprising skin and/or hair representative of the subject for which the cosmetic composition is to be provided to.

In one or more embodiments, the rejuvenating cosmetic compositions described herein or formulations thereof will include one or more recombinant proteins (e.g., such as the one or more proteins described above) and/or mRNA mimetics to upregulate one or more anti-aging proteins as described above, which are further combined with one or more long ncRNA, the long ncRNA providing conditions associated with anti-aging. Said combination provides a synergistic effect having improved anti-aging effects. Said synergistic combination, in one or more embodiments, may be obtained and/or identified and/or selected for after performing an analysis of the rejuvenated cells (rejuvenated in any manner as described herein, and rejuvenated from a sample comprising skin and/or hair of a subject for which the cosmetic composition is to be provided to, and/or from a representative sample comprising skin and/or hair representative of the subject for which the cosmetic composition is to be provided to). In one or more embodiments, some or all of such a synergistic combination may be obtained and/or identified and/or selected for after comparing rejuvenated cells and/or their components with original sample cells, in which the rejuvenated cells are rejuvenated in any manner as described herein, and are rejuvenated from a sample comprising skin and/or hair of a subject for which the cosmetic composition is to be provided to, and/or from a representative sample comprising skin and/or hair representative of the subject for which the cosmetic composition is to be provided to, and in which the original cells are from the sample comprising skin and/or hair of the subject for which the cosmetic composition is to be provided to, and/or from a representative sample comprising skin and/or hair representative of the subject for which the cosmetic composition is to be provided to. In one or more embodiments, some or all of the synergistic combination, as a synergistic rejuvenating combination, may be obtained and/or identified and/or selected for after comparing differentiated young or younger cells and/or their components against original sample cells or against cell types that were not subjected to rejuvenation in any manner as described herein (e.g., differentiated young or younger keratinocytes or differentiated young or younger keratinocyte-like cells compared against a known keratinocyte cell line or keratinocytes obtained from the sample and/or the subject). The differentiated young or younger cells have differentiated from rejuvenated cells in any manner described herein. The rejuvenated cells are rejuvenated from a sample comprising skin and/or hair of a subject for which the cosmetic composition is to be provided to, and/or from a representative sample comprising skin and/or hair representative of the subject for which the cosmetic composition is to be provided to, and in which the original cells are from the sample comprising skin and/or hair of the subject for which the cosmetic composition is to be provided to, and/or from a representative sample comprising skin and/or hair representative of the subject for which the cosmetic composition is to be provided to.

In one or more embodiments, the rejuvenating cosmetic compositions described herein or formulations thereof will include one or more endocrine molecules such as, without limitation, prohormones, hormones, or hormone-like molecules. In one or more embodiments, the endocrine molecules will be present in the composition or formulation at concentrations and ratios to each other similar to those concentrations and ratios found in extracts from rejuvenated cells and/or their culture media. Said combinations and ratios provide a synergistic effect having improved anti-aging effects. In one or more embodiments, the endocrine molecules will be obtained from the rejuvenated cells and/or their culture media. Said synergistic combinations, in one or more embodiments, may be obtained and/or identified and/or selected for after performing an analysis of rejuvenated cells and/or their culture media. Such rejuvenated endocrine hormone-producing cells may be obtained by rejuvenating, reprogramming, or rejuvenating and reprogramming (not necessarily in that order) cells from the subject or a representative of the subject into endocrine cells or endocrine-cell like cells, or immune cells or immune-cell like cells, or endothelial cells or endothelial cell-like cells. Such reprogramming and/or rejuvenating may involve first dedifferentiating cells, then differentiating them into endocrine-molecule producing cells; or, transdifferentiating cells into endocrine-molecule producing cells; or, rejuvenating cells that are already of an endocrine molecule-producing type. In one or more embodiments, some or all of such a synergistic combination may be obtained and/or identified and/or selected for after comparing rejuvenated cells and/or their components with original sample cells, in which the rejuvenated cells are rejuvenated in any manner as described herein, and are rejuvenated from a sample comprising skin and/or hair and/or blood and/or saliva and/or buccal cells and/or another tissue or cell type of a subject for which the cosmetic composition is to be provided to, and/or from a representative sample comprising skin and/or hair and/or blood and/or saliva and/or buccal cells and/or another tissue or cell type representative of the subject for which the cosmetic composition is to be provided to, and in which the original cells are from the sample comprising skin and/or hair and/or blood and/or saliva and/or buccal cells and/or another tissue or cell type of the subject for which the cosmetic composition is to be provided to, and/or from a representative sample comprising skin and/or hair and/or blood and/or saliva and/or buccal cells and/or another tissue or cell type representative of the subject for which the cosmetic composition is to be provided to. In one or more embodiments, some or all of the synergistic combination, as a synergistic rejuvenating combination, may be obtained and/or identified and/or selected for after comparing differentiated young or younger cells and/or their components against original sample cells or against cell types that were not subjected to rejuvenation in any manner as described herein (e.g., differentiated young or younger endocrine molecule-producing cells or differentiated young or younger endocrine molecule-producing cells compared against a known endocrine cell line or endocrine cells obtained from the sample and/or the subject). The differentiated young or younger cells have differentiated from rejuvenated cells in any manner described herein. The rejuvenated cells are rejuvenated from a sample comprising skin and/or hair and/or blood and/or saliva and/or buccal cells and/or another tissue or cell type of a subject for which the cosmetic composition is to be provided to, and/or from a representative sample comprising skin and/or hair and/or blood and/or saliva and/or buccal cells and/or another tissue or cell type representative of the subject for which the cosmetic composition is to be provided to, and in which the original cells are from the sample comprising skin and/or hair of the subject for which the cosmetic composition is to be provided to, and/or from a representative sample comprising skin and/or hair and/or blood and/or saliva and/or buccal cells and/or another tissue or cell type representative of the subject for which the cosmetic composition is to be provided to.

In one or more embodiments, the ratios of components of two or more of the cosmetic compositions are similar to the ratios of the components found in young skin or hair follicles, or in extracts from rejuvenated cells or their culture media. In various embodiments, the ratios are at least about 25%, about 50%, or about 75% similar to the ratios of the corresponding components as found in young skin or hair follicles, or in extracts from rejuvenated cells or their culture media. Such ratios can increase the synergistic effects of the components.

In one or more embodiments, the rejuvenating cosmetic compositions described herein or formulations thereof will include one or more of an antioxidant, anti-inflammatory, matrix metalloproteinase inhibitor, and various combinations thereof, for rejuvenation of skin.

In one or more embodiments, the rejuvenating cosmetic compositions described herein or formulations thereof will include a cosmetically acceptable carrier, including but not limited to a liposomal and/or lipodermal carrier. In one or more embodiments, the cosmetic compositions described herein will not include a cosmetically acceptable carrier. In addition, or as an alternative, the carrier may comprise a carrier oil, and/or carrier butter. In one or more embodiments, the carrier oil and/or carrier butter are provided as a base.

In one or more embodiments, the rejuvenating cosmetic compositions described herein or formulations thereof will not include an excipient.

In one or more embodiments, the rejuvenating cosmetic compositions described herein or formulations thereof will include one or more additives including but not limited to colorant, fragrance, UV protectant, moisturizer, vanishing agent.

In at least some of the embodiments, at least some of the components described above provided for at least one cosmetic composition and formulations thereof will be selectively customized for a specific and/or distinct and/or personal skin type, and/or skin profile. In at least some of the embodiments, at least some of the components described above provided for in at least one cosmetic composition and formulations thereof will be selectively customized for a specific and/or distinct and/or personal hair type, and/or hair profile.

In at least some of the embodiments, at least some of the components and rejuvenating formulations thereof will be selectively prepared for a subject from which skin and/or hair has been obtained, and for which at least one cosmetic composition is to be provided to. In at least some of the embodiments, at least some of the components and rejuvenating formulations thereof will be selectively representative of and/or prepared for one or more subjects, the one or more subjects representative of and/or resembling a subject from which skin and/or hair has been obtained from, and for which at least one cosmetic composition is to be provided to.

In one or more embodiments, the rejuvenating cosmetic compositions described herein or formulations thereof are customized and generated based on a specific and/or distinct and/or personal skin and/or hair type, and/or specific and/or distinct and/or personal skin and/or hair profile.

In one or more embodiments, the rejuvenating cosmetic compositions described herein or formulations thereof are customized and generated based on a customer skin and/or hair type, and/or customer skin and/or hair profile. The customer may be a single customer having a customer type and/or profile, or may be a group of customers representative of one customer type and/or profile. The customer may be a subject from which a sample has been obtained, and from which cells have been rejuvenated. The customer may be representative of a subject from which a sample has been obtained, and from which cells have been rejuvenated.

The rejuvenating cosmetic compositions described herein or formulations thereof described herein are considered stable.

The rejuvenating cosmetic compositions described herein or formulations thereof described herein are considered safe.

The rejuvenating cosmetic compositions described herein or formulations thereof described herein may be lipid-based, water-based, or alcohol-based.

In one or more embodiments, the rejuvenating cosmetic compositions described herein or formulations thereof will include at least some of the components described above.

In one or more embodiments, the rejuvenating cosmetic compositions described herein or formulations thereof will include a plurality of the components described above.

The rejuvenating cosmetic compositions described herein or formulations thereof described herein may be provided as a cream.

The rejuvenating cosmetic compositions described herein or formulations thereof described herein may be provided as a lotion.

The rejuvenating cosmetic compositions described herein or formulations thereof described herein may be provided as a gel.

The rejuvenating cosmetic compositions described herein or formulations thereof described herein may be provided as a foam.

The rejuvenating cosmetic compositions described herein or formulations thereof described herein may be provided as an ointment.

The rejuvenating cosmetic compositions described herein or formulations thereof described herein may be provided in a package or container, such as a jar, tube, bottle, metered syringe, and the like.

In one or more embodiments, a cosmetic formulation may be customized for a subject. In one or more embodiments, the cosmetic formulation comprises an extract from modified cells and/or media in which the modified cells have been cultured. In one or more embodiments, the modified cells may be produced by modifying cells from the subject or a representative of the subject to produce modified cells, and the modified cells are produced by one or more of: a) rejuvenation, b) reprogramming to a less differentiated state, c) differentiation, and d) transdifferentiation, in any order and in any number of repetitions.

In one or more embodiments, the cosmetic formulation further comprises at least a cosmetically acceptable base, and, optionally, a cosmetically acceptable penetration enhancer. In one or more embodiments, the cosmetically acceptable base and the cosmetically acceptable penetration enhancer may be provided in various ratios to provide varying penetration depth of the cosmetic formulation. In one or more embodiments, the cosmetically acceptable penetration enhancer comprises one or more of a pluronic lecithin organogel, a lipid component, a polymeric vehicle, a microparticle, a nanoparticle, a liposome component, and combinations thereof.

In one or more embodiments, the cosmetic formulation further comprises one or more cosmetically acceptable additives selected from the group consisting of an antioxidant, an anti-inflammatory, a matrix metalloproteinase inhibitor, and combinations thereof.

In one or more embodiments, the cosmetic formulation further comprises one or more of a colorant, a fragrance, an UV protectant, a preservative, a moisturizer, and a vanishing agent.

In one or more embodiments, the cosmetic formulation further comprises one or more modulating components that increase or decrease representation in the unmodified cells of one or more target molecular components expressed or produced by the modified cells. In one or more embodiments, the one or more modulating components may be selected from the group consisting of mRNA mimetics, long non-coding RNA mimetics, miRNA mimics, recombinant proteins, recombinant peptides, exosomes, carbohydrates, polysaccharides, proteoglycans, sugars, metabolites, lipids, prohormones, hormones, fatty acids, vitamins, metals, ions, co-factors, small molecules, and combinations thereof. In one or more embodiments, the modulating components cause the unmodified cells from the subject to increase representation of each of the one or more target molecules found in the modified cells, at a level within about 10%, about 20%, about 50%, about 100%, or about 200%, of the level found in the modified cells.

In one or more embodiments, the cosmetic formulation further comprises one or more miRNA mimics that target one or more mRNA or miRNA species expressed by the modified cells. In one or more embodiments, the mRNA or miRNA species that are targeted support one or more of senescence, inflammatory response, and oxidative stress.

In one or more embodiments, the cosmetic formulation further comprises one or more modulating components not naturally expressed or produced by the unmodified cells. In one or more embodiments, the modulating components stimulate or repress expression in the unmodified cells of one or more target molecular components expressed or produced by the modified cells. In one or more embodiments, the one or more modulating components may be selected from the group consisting of mRNA mimetics, long non-coding RNA mimetics, miRNA mimics, recombinant proteins, recombinant peptides, exosomes, carbohydrates, polysaccharides, proteoglycans, sugars, metabolites, lipids, prohormones, hormones, fatty acids, vitamins, metals, ions, co-factors, small molecules, and combinations thereof. In one or more embodiments, the modulating components cause the unmodified cells from the subject to stimulate each of the one or more target molecules found in the modified cells, at a level within about 10%, about 20%, about 50%, about 100%, or about 200%, of the level found in the modified cells.

In one or more embodiments, modifying the cells by one or more of reprogramming and rejuvenation involves increasing an amount of one or more of telomerase reverse transcriptase (TERT), RAP1, TIN2, TRF1, TRF2, TPP1, POT1, SIRT, SIRT-1, SIRT-2, SIRT-3, SIRT-4, SIRT-5, SIRT-6, SIRT-7, JunD, and GDF11 in the subject's cells.

In one or more embodiments, modifying the cells by differentiation produces cells characterized as one or more of immune cells, immune-like cells, vascular endothelial cells, vascular endothelial-like cells, endocrine cells, endocrine-like cells, fibroblasts, fibroblast-like cells, keratinocytes, keratinocyte-like cells, melanocytes, and melanocyte-like cells, or other skin cell types.

In one or more embodiments, modifying the cells by one or more of rejuvenating, reprogramming to a less differentiated state, differentiation, and/or transdifferentiation may be repeated more than once.

In one or more embodiments, the cells from the subject may be characterized as one or more of skin stem cells, immune cells, immune-like cells, vascular endothelial cells, vascular endothelial-like cells, endocrine cells, endocrine-like cells, fibroblasts, fibroblast-like cells, keratinocytes, keratinocyte-like cells, melanocytes, and melanocyte-like cells, or other skin cell types.

In one or more embodiments, a method of preparing a cosmetic formulation customized for a subject comprises: a) providing a sample containing cells from the subject or a representative of the subject, and modifying the cells by one or more of: i) rejuvenating the cells, ii) reprogramming the cells to a less differentiated state, iii) differentiating the cells; iv) transdifferentiating the cells, in any order and any number of repetitions to produce modified cells, b) obtaining an extract from the modified cells and/or their cell culture medium, and c) providing the extract to the cosmetic formulation.

In one or more embodiments, the cosmetic formulation further comprises at least a cosmetically acceptable base, and, optionally a cosmetically acceptable penetration enhancer. In one or more embodiments, the cosmetically acceptable base and the cosmetically acceptable penetration enhancer are provided in various ratios to provide a varying penetration depth of the cosmetic formulation. In one or more embodiments, the cosmetically acceptable penetration enhancer comprises one or more of a pluronic lecithin organogel, a lipid component, a polymeric vehicle, a microparticle, a nanoparticle, and a liposome component.

In one or more embodiments, the cosmetic formulation further comprises one or more cosmetically acceptable additives selected from the group consisting of an antioxidant, an anti-inflammatory, a matrix metalloproteinase inhibitor, and combinations thereof.

In one or more embodiments, the cosmetic formulation further comprises one or more of a colorant, a fragrance, a UV protectant, a preservative, a moisturizer, and a vanishing agent.

In one or more embodiments, the cosmetic formulation further comprises one or more modulating components that increase or decrease representation in the unmodified cells of one or more target molecular components expressed or produced by the modified cells. In one or more embodiments, the one or more modulating components may be selected from the group consisting of mRNA mimetics, long non-coding RNA mimetics, miRNA mimics recombinant proteins, recombinant peptides, exosomes, carbohydrates, polysaccharides, proteoglycans, sugars, metabolites, lipids, prohormones, hormones, fatty acids, vitamins, metals, ions, co-factors, small molecules, and combinations thereof. In one or more embodiments, the modulating components cause the unmodified cells from the subject to increase representation of each of the one or more target molecules found in the modified cells, at a level within about 10%, about 20%, about 50%, about 100%, or about 200%, of the level found in the modified cells.

In one or more embodiments, the cosmetic formulation further comprises one or more miRNA mimics that target one or more mRNA or miRNA species expressed by the modified cells. In one or more embodiments, the mRNA or miRNA species that are targeted support one or more of senescence, inflammatory response, oxidative stress.

In one or more embodiments, the cosmetic formulation further comprises one or more modulating components not naturally expressed or produced by the unmodified cells. In one or more embodiments, the modulating components stimulate or repress expression in the unmodified cells of one or more target molecular components expressed or produced by the modified cells. In one or more embodiments, the one or more modulating components may be selected from the group consisting of mRNA mimetics, long non-coding RNA mimetics, miRNA mimics recombinant proteins, recombinant peptides, exosomes, carbohydrates, polysaccharides, proteoglycans, sugars, metabolites, lipids, prohormones, hormones, fatty acids, vitamins, metals, ions, co-factors, small molecules, and various combinations thereof. In one or more embodiments, the modulating components stimulate the unmodified cells from the subject to express each of the one or more target molecules found in the modified cells, at a level within about 10%, about 20%, about 50%, about 100%, or about 200%, of the level found in the modified cells.

In one or more embodiments, modifying the cells by one or more of the reprogramming the cells to a less differentiated state step and the rejuvenating the cells step involves increasing an amount of one or more of telomerase reverse transcriptase, RAP1, TIN2, TRF1, TRF2, TPP1, POT1, SIRT, SIRT-1, SIRT-2, SIRT-3, SIRT-4, SIRT-5, SIRT-6, SIRT-7, JunD, and GDF11 in the subject's cells.

In one or more embodiments, the differentiating the cells step produces cells characterized as one or more of immune cells, immune-like cells, vascular endothelial cells, vascular endothelial-like cells, endocrine cells, endocrine-like cells, fibroblasts, fibroblast-like cells, keratinocytes, keratinocyte-like cells, melanocytes, and melanocyte-like cells, and other skin cell types.

In one or more embodiments, modifying the cells by one or more of the rejuvenating the cells step, the reprogramming the cells to a less differentiated state step, the differentiating the cells step, and the transdifferentiating the cells step may be repeated more than once.

In one or more embodiments, the cells from the subject may be characterized as one or more of skin stem cells, immune cells, immune-like cells, vascular endothelial cells, vascular endothelial-like cells, endocrine cells, endocrine-like cells, fibroblasts, fibroblast-like cells, keratinocytes, keratinocyte-like cells, melanocytes, and melanocyte-like cells, and other skin cell types.

In one or more embodiments, a method of preparing a cosmetic formulation customized for a subject comprises: a) providing a computer system, b) providing a sample containing cells from the subject or a representative of the subject, and using the information relating to the subject to modify the cells by one or more of: i) rejuvenating the cells, ii) reprogramming the cells to a less differentiated state, iii) differentiating the cells, iv) transdifferentiating the cells, in any order and any number of repetitions to produce modified cells, c) obtaining an extract from the modified cells and/or their cell culture medium, and d) providing the extract to the cosmetic formulation. In one or more embodiment, the computer system comprises: i) information relating to the subject from a user's information handling device, wherein the user's information handling device comprises a display screen, ii) a processor connected to a network for receiving the information, iii) a storage device connected to the processor, wherein the storage device is a nontransitory computer readable medium, iv) a computer program in the storage to access, analyze, acquire, collect, compare, enter, store, transmit and/or update information relating to the subject.

In one or more embodiments, the method further comprises providing access to the subject to the software program to access, acquire, collect, compare, enter, store, transmit and update information related to the subject.

In one or more embodiments, the software program runs on a computer, phone, tablet, or other personal computing device.

In one or more embodiments, the software program saves the information relating to the subject to the storage device.

In one or more embodiments, the information relating to the subject comprises one or more of lifestyle, stress, sun exposure, geographic location, skin type, diet, genetic background, cultural background, skin appearance, skin problems, medical history, travel history, cosmetics use, supplement use, drug use, or exercise. In one or more embodiments, the information relating to the subject comprises one or more of their social media account information, geographic location, movement, physiological parameters, heartbeat patterns, breathing patterns, or body temperature patterns.

In one or more embodiments, the method further comprises adding to or removing from the cosmetic formulation one or more cosmetically acceptable additives selected based on information relating to the subject.

In one or more embodiments, the software program provides suggestions to the user for customizing a cosmetic formulation.

In one or more embodiments, the software program provides the user with the ability to customize the cosmetic formulation.

In one or more embodiments, the software program provides the user with the ability to buy cosmetic formulations.

In one or more embodiments, the software program enables the user to take photographs of the subject's skin or hair, wherein photographs are used to evaluate the success of a cosmetic formulation. In one or more embodiments, the photographs of skin or hair may be processed using an artificial intelligence program to estimate the success of the cosmetic formulation. In one or more embodiments, the photographs of skin or hair may be evaluated by a human (self-assessment and/or by a professional) to estimate the success of the cosmetic formulation. In one or more embodiments, the photographs of skin or hair may be evaluated by presenting the photographs to individuals through a computer network or through the software program.

In one or more embodiments, the software program enables the user to save photographs of the appearance of the subject's skin or hair to the storage device.

In one or more embodiments, the software program enables the user to take photographs of the subject's food, wherein the photographs are used to estimate the composition of the diet of the subject.

In one or more embodiments, the software program, optionally, enables the user to save photographs of the subject's food to the storage device.

In one or more embodiments, the information relating to the subject may be used in an iterative feedback loop comprising a plurality of cycles. In one or more embodiments, the information relating to the subject may be collected in each cycle. In one or more embodiments, the cosmetic formulation may be adjusted according to the information relating to the subject, and the adjusted cosmetic formulation is provided to the subject.

In one or more embodiments, the method further comprises providing access to the subject to the software program to access, acquire, collect, compare, enter, store, transmit and update information related to the subject. In one or more embodiment, the information relating to the subject may be used in an iterative feedback loop comprising a plurality of cycles. In one or more embodiments, the information relating to the subject may be collected at a beginning of each cycle. In one or more embodiments, the cosmetic formulation may be adjusted according to the information relating to the subject, and the adjusted cosmetic formulation is provided to the subject.

These and additional embodiments are described below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a further understanding of the nature and objects of the present invention, reference should be made to the following detailed disclosure, taken in conjunction with the accompanying drawings, in which like parts are given like reference numerals, and wherein.

DETAILED DESCRIPTION OF EMBODIMENTS OF THE INVENTION

Figure 1:
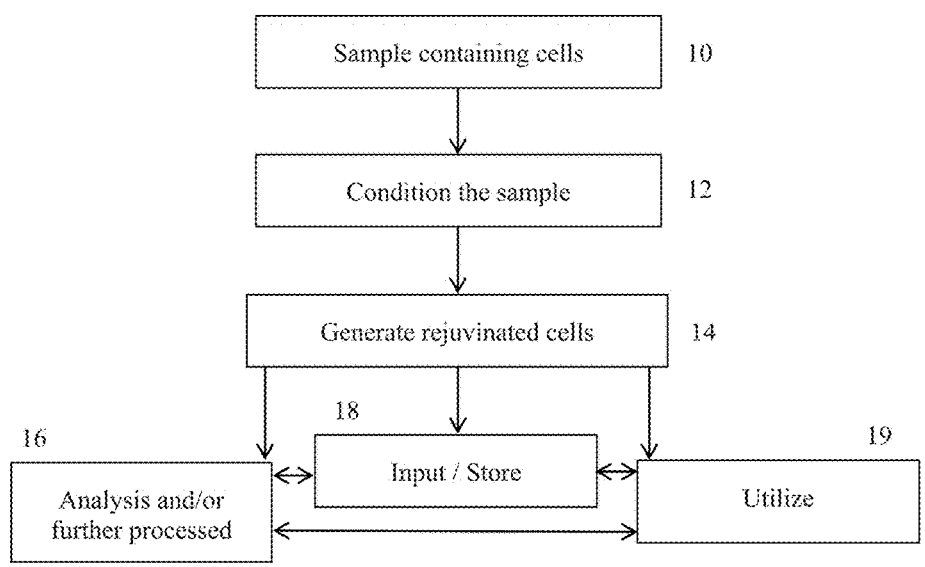
FIG. 1 depicts a first representative embodiment described herein.

The following detailed description of various embodiments of the present invention references the accompanying drawings, which illustrate specific embodiments in which the invention can be practiced. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains. Therefore, the scope of the present invention is defined only by the appended claims, along with the full scope of equivalents to which such claims are entitled.

Described herein are cosmetic compositions and formulations thereof, at least some of which are based in part on personalizing one or more cosmetic compositions and formulations. The cosmetic compositions and formulations described herein are topically based, for use on skin and/or hair. These cosmetic compositions and formulations include one or more components that are uniquely identified and/or selected for the skin and/or hair of a subject, the subject being one for whom at least one of the compositions and formulations is to be provided to, or one who is representative of or embodying the one for whom at least one of the compositions and formulations is to be provided to. From the subject or a representative of the subject, a sample is obtained, and from the sample, the one or more components that are uniquely identified and/or selected for are identified and/or obtained.

Generally, in one or more embodiments, at least one or more of the components provided in the cosmetic compositions and formulations described herein are selected for a customer. The customer may be the subject from whom the one or more components were uniquely identified and/or selected from, or the customer may be one who is representative of the subject from whom the one or more components were uniquely identified and/or selected from. The customer will have a skin type and/or skin profile, and/or a hair type and/or hair profile. A skin type and/or skin profile, and/or a hair type and/or hair profile are also associated with each subject. This provides a means for associating a customer (having a skin type and/or skin profile, and/or a hair type and/or hair profile) with the skin type and/or skin profile, and/or a hair type and/or hair profile of the subject. It also provides a means for the subject (from whom the one or more components were uniquely identified and/or selected from, and for which the one or more components were provided into a specific and/or distinct and/or personal cosmetic compositions and formulations), to become representative of or embodying the customer, such that the specific and/or distinct and/or personal cosmetic compositions and formulations that was created therefrom may be provided to the customer, when the customer is associated with a skin type and/or skin profile, and/or a hair type and/or hair profile of the subject. The type and/or profile may include any one or more of type and nature of the skin and/or hair, physiology, environment, ethnicity, age, geography, as examples.

In one or more embodiments, the one or more components and the formulation(s) containing the one or more components will be selective for a subject from which a sample (e.g., skin and/or hair) has been obtained. The subject is associated with a skin type and/or skin profile, and/or a hair type and/or hair profile. The formulation containing the one or more components may be provided to at least one cosmetic composition. The at least one composition may be provided and/or administered to the subject, or to a customer for whom the subject is representative of or embodying, in which the customer is associated with the skin type and/or skin profile, and/or a hair type and/or hair profile of the subject.

In one or more embodiments, the one or more components and the formulation(s) containing the one or more components will be selective for a plurality of subjects from which a plurality of samples (e.g., skin and/or hair) have been obtained. The plurality of subjects is associated with a skin type and/or skin profile, and/or a hair type and/or hair profile. The formulation containing the one or more components may be provided to at least one cosmetic composition. The at least one composition may be provided and/or administered to at least one of the plurality of subjects, or to a customer for whom the plurality of subjects are representative of or embodying, in which the customer is associated with the skin type and/or skin profile, and/or a hair type and/or hair profile of the plurality of subjects.

A type and/or profile as described herein may be provided by one or more samples from at least one subject. A type and/or profile may also be provided by one or more surveys. In one or more embodiments, a type and/or profile is utilized to formulate and provide a cosmetic composition that is unique and specific for a subject (from whom a sample was obtained, and utilized to formulate and to provide the cosmetic composition). Accordingly, in one or more embodiments, a customized cosmetic composition and formulation thereof is designed and/or generated from a sample, and is based, at least in part or in whole, on the sample's type and/or profile, the sample being obtained from at least one subject. In some embodiments, the subject may be the person or the animal for whom or which the cosmetic composition is to be provided to. In one or more embodiments, the cosmetic composition and formulation thereof may be further analyzed scientifically, and/or modified scientifically, and/or optimized scientifically, such as to enhance efficacy and/or stability. In one or more embodiments, the cosmetic composition and formulation thereof may be further modified, and/or optimized based on input from one or more customers.

In one or more embodiments, a type and/or profile is utilized to formulate and provide a cosmetic composition that is customized (unique and/or specific) for a customer (who is represented by and/or embodied by at least one sample, and/or type and/or profile thereof, the at least one sample being utilized to formulate and to provide the cosmetic composition). Accordingly, in one or more embodiments, a cosmetic composition and formulation thereof is designed and/or generated for the type and/or profile of a customer, and is based, at least in part or in whole, on the type and/or profile that is embodied and/or represented by the type and/or profile of the customer.

In addition, or as an alternative, a group type and/or group profile is utilized to formulate and provide a cosmetic composition that is customized (unique and/or specific) for a group of customers (who are represented by and/or embodied by at least one sample, and/or type and/or profile thereof, the at least one sample being utilized to formulate and to provide the cosmetic composition). Accordingly, in one or more embodiments, a cosmetic composition and formulation thereof is designed and/or generated for a group of customers, the group of customers embodying or representing one group type and/or group profile, such that the cosmetic composition and formulation thereof for the group of customers is based, at least in part or in whole, on the type and/or profile that is embodied or represented by the group type and/or group profile.

In one or more embodiments, a personalized cosmetic composition and formulation thereof is provided for an individual or customer, or for a group embodied by or representative of the individual, by one or more of: (i) utilization of one or more samples as described herein; (ii) a survey and/or series of self-evaluation questions as described herein; and (iii) a selection of one or more personal preferences regarding skin and/or hair care and/or products thereof. In some embodiments, a personalized cosmetic composition and formulation thereof for an individual is provided by utilizing (i) and (ii). In some embodiments, a personalized cosmetic composition and formulation thereof for an individual is provided by utilizing (i) and (iii).

In some embodiments, a personalized cosmetic composition and formulation thereof for an individual is provided by utilizing all of (i), (ii), and (iii).

In one or more embodiments, cosmetic compositions and formulations thereof may be updated/modified/optimized by any one or more of: best averages; subject feedback; personal preferences; seasonal trends and/or targets; best ingredients; and/or scientific findings. Any existing cosmetic composition and formulation thereof may be updated and/or enhanced at any time, in real-time, and/or on-demand.

In one or more embodiments, for every individual or customer for which a personalized cosmetic composition and formulation thereof is provided or may be provided, a profile of said individual is generated. Each profile will include at least one or more of: (a) components and/or ingredients in their personalized cosmetic composition and formulation thereof as described above; (b) strength and/or quantity of each component and/or ingredient in their personalized cosmetic composition and formulation thereof; (c) data about the one or more samples obtained from the individual, and/or that is embodied or representative of the individual; (d) the one or more personal preferences regarding skin and/or hair care and/or products thereof; and (e) survey and/or self-evaluation answers (in response to the survey and/or series of self-evaluation questions). In one or more embodiments, a profile for an individual is provided by utilizing at least three of the criteria identified as any one of (a), (b), (c), (d), and (e). In one or more embodiments, a profile for an individual is provided by utilizing at least four of the criteria identified as any one of (a), (b), (c), (d), and (e). In one or more embodiments, a profile for an individual is provided by utilizing all of (a), (b), (c), (d), and (e). In one or more embodiments, a profile for an individual may be modified, enhanced, and/or updated. The modification, enhancement, and/or update may be provided by the individual. In addition, or alternatively, modification, enhancement, and/or update may be provided utilizing a system through which the profile is generated.

In one or more embodiments, a profile for an individual or customer is utilized to provide a type and/or profile of the skin and/or hair of the individual or customer.

In one or more embodiments, a profile for an individual or customer, as well as a type and/or profile of a sample from that individual or customer, are utilized to provide a type and/or profile of the skin and/or hair of the individual or customer.

In one or more embodiments, a personalized cosmetic composition and formulation thereof, and a profile for an individual or customer, are included in an information technology (IT) system (local or networked system, and/or cloud-based) having hardware (e.g., one or more devices, routers, switches, cards, and/or cables, etc.), software (e.g., for operations, management, manufacturing, distribution, etc.), with storage capabilities (data storage media, data back-up, storage virtualization, and/or storage provisioning, etc.), with or without network enablement (internet connectivity, firewall, security, T-1 lines, DSL, satellite, wireless protocols, IP addressing, etc.). The system may be utilized to: (i) generate additional information about the individual or customer; (ii) update existing information about the individual or customer; (iii) modify the personalized cosmetic composition for the individual or customer; and/or (iv) optimize the personalized cosmetic composition for the individual or customer (e.g., based on one or more scientific analyses, clinical data, and/or other information received from or about the individual, and/or about the cosmetic composition). The system may include resource planning, customer relationship management, one or more productivity applications, and/or user authentication, as examples of further facilitative features of the system. The system may utilize a networked and/or cloud-based infrastructure, and may include one or more functional units in operable communication, the functional units involving one or more or all of the following: retail store, on-line store, workstation, mobile device, local application, mobile application, research facility, manufacturing facility, distribution facility, warehouse, data storage center, etc.

Any cosmetic composition and formulation thereof as described above or below, and as provided in any manner described herein, may be provided to, may be maintained/stored, may be analyzed by, may be communicated through, and/or may be updated by the system. Similarly, data about any one or more personalized cosmetic composition and formulation thereof for an individual or customer, or for a group of individuals or customers (e.g., ones that form a group type and/or group profile) may be provided to, may be maintained/stored, may be analyzed by, may be communicated through, and/or may be updated by the system. Similarly, data about any individual or customer, or group of individuals or customers (e.g., ones that form a group type and/or group profile), and data about any sample from the individual or customer or representative of the individual or customer may be provided to, may be maintained/stored, may be analyzed by, may be communicated through, and/or may be updated by the system.

Referring to FIG. 1, a flow chart depicting a representative type and profile process utilizing a sample as described herein is schematically illustrated. As shown in block 10, the sample must contain cells. More than one sample may be provided. Generally, each sample is processed independently. In some embodiments, more than one sample may be provided, and may be processed cooperatively, simultaneously, and/or in parallel. The sample may be a skin sample containing cells. The sample may be a hair sample containing cells. Generally, the sample provides "original" cells from a subject. The sample may be obtained by one or more noninvasive means (e.g., swab of the skin and/or hair). Invasive means may also be utilized (e.g., scratch, slice, prick, excision, etc., in which skin and/or hair is obtained, preferably without blood, or endothelial cells). In some embodiments, the subject is one for which a cosmetic composition and formulation is to be provided to. In some embodiments, the subject is a subject representative of a group type and/or group profile. Because the sample containing cells may be from a subject that is no longer young (e.g., no longer developing, and/or no longer 18 years or less), such a sample containing cells may, in some embodiments, be depicted as comprising "old" cells, or comprising "older" cells. Cells from the sample may be fibroblasts, or may include fibroblasts. In addition, or as an alternative, cells from the sample may be keratinocytes, or may include keratinocytes, or may be cells containing keratin.

The sample containing cells is conditioned, as depicted in block 12. In some embodiments, conditioning includes initially extracting the cells from the sample. In addition or as an alternative, the conditioning may include initially expanding the cells from the sample. The initial expanding is performed in vitro. The initial expanding of the cells from the sample may be performed utilizing a suitable tissue culture setting or environment. In at least some of the embodiments, the conditioning will generate modified cells (rejuvenated cells), ones that overexpress one or more proteins associated with and/or involved in regulating aging (e.g., hTERT, shelterin complex components, JunD, GDF11, etc.), as depicted in block 14. In one or more embodiments, the conditioning will generate modified cells (rejuvenated cells), ones that are reprogrammed as pluripotent cells (e.g., embryonic-like pluripotent stem cells or iPSCs). Any of such modifications cells may provide and/or define the rejuvenated cells. The rejuvenated cells, and/or one or more components thereof, may be utilized for at least one cosmetic composition described herein (block 19). The rejuvenated cells, and/or one or more components thereof, may be further analyzed and/or processed (block 16). The rejuvenated cells, and/or one or more components thereof, may be stored (block 18). When the rejuvenated cells, and/or one or more components thereof, are further processed and/or utilized, some, all, or at least a portion of the further processing and/or utilized product, and/or data thereof, may also be stored, and/or further processed, and/or further utilized.

Figure 2:
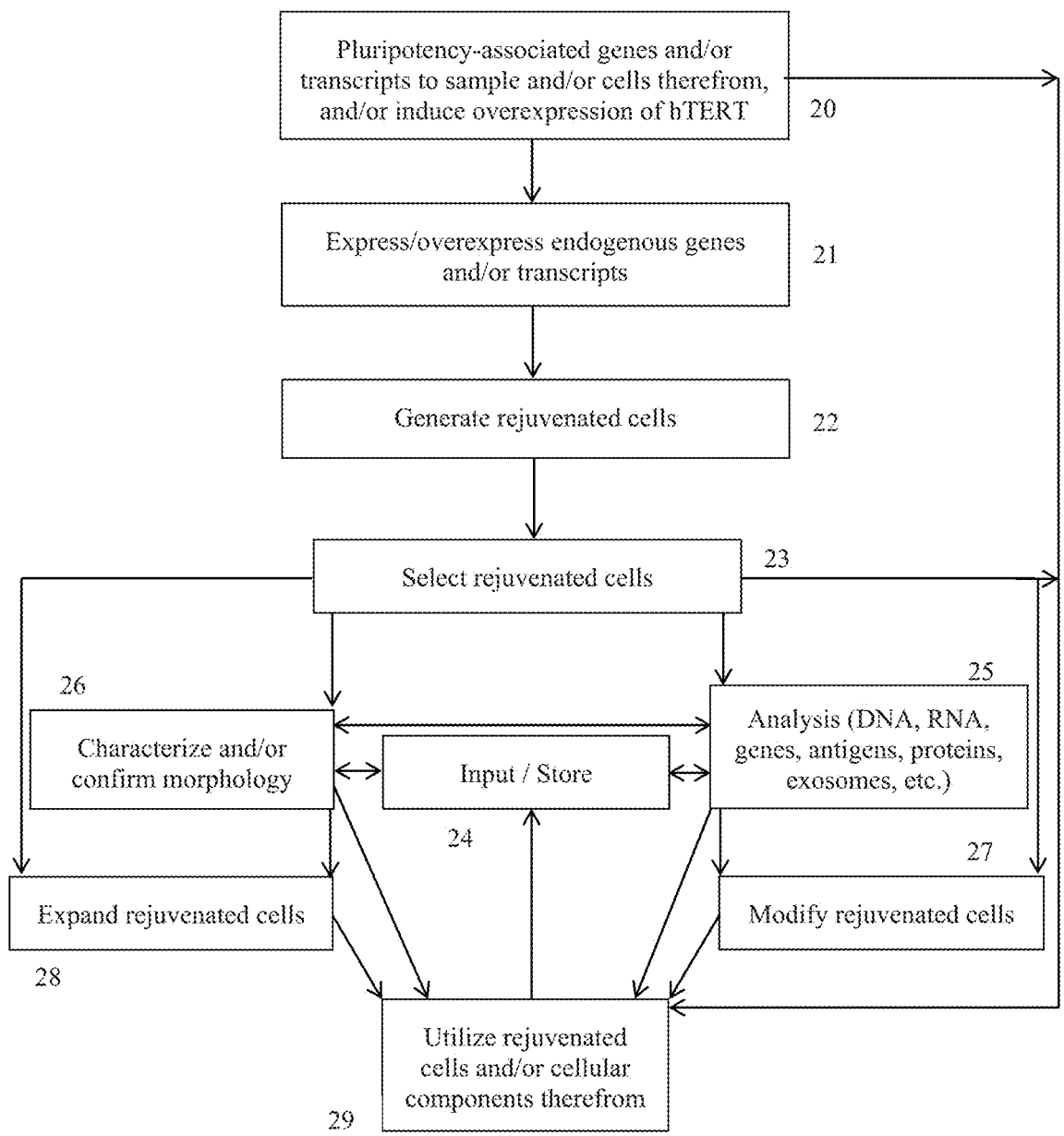
FIG. 2 depicts a second representative embodiment described herein.

A flow chart depicting a representative conditioning process to provide the rejuvenated cells as described herein is schematically illustrated in FIG. 2. One process is one in which cells from the sample are induced to express or overexpress, and/or suppress specific transcription factors, by a somatic cell reprogramming process. Here, pluripotency-associated genes and/or transcripts are provided to cells from the sample (block 20). The pluripotency-associated genes and/or transcripts are or include the Yamanaka or OSKM transcription factors (Oct3/4, Sox2, Klf4, cMyc), and/or Thomson or alternative transcription factors (Oct3/4, Sox2, Nanog, Lin28, used together, and/or with some or all of the Yamanaka or OSKM transcription factors), which may be augmented with one or more enhancers (e.g., REM2, cyclin D1, UTF1, SALL4, ESRRβ, NR5A2, TCL1A, TFCP2L1, TRIM71), and/or with downstream targets of the pluripotency-associated transcription factors, and/or by blocking of cell cycle-dependent kinase inhibitors (e.g., CIp1, INK4A, ARF), and/or suitable combinations thereof, as understood in the art, which has been described in at least the following: *Cell*, Nov. 30, 2007, 131(5):861-72; *Nature*, Aug. 7, 2009, 460(7259):1145-1148; *Cell Stem Cell*, Nov. 5, 2010, 7(5):618-630; *Nature Reviews Molecular Cell Biology* 2016, 17:183-193, all of which are incorporated herein by reference in their entirety, and to the maximal extent allowable.

The conditioning process of FIG. 2 may include having pluripotency-associated genes as open reading frames of the human genes for the pluripotency-associated transcription factors (e.g., the requisite OSKM transcription factors, and/or the requisite alternative transcription factors as described above and/or as understood in the art), and delivering to the sample containing cells, and/or to cells from the sample, as depicted in block 20. These may be delivered by providing the requisite pluripotency-associated genes on a vector (e.g., plasmid) and subsequently, via a carrier containing the vector (e.g., viral vector, adenovirus, transposon, phagemid, Sendai virus, plasmid, as examples), delivering directly to the cells (e.g., electroporation, infection, transduction, or transfection). In some embodiments, the OSKM factors (with or without additional transcription factors, enhancers, etc.) are provided in one polycistronic vector. In some embodiments, the OSKM factors (with or without additional transcription factors, enhancers, etc.) are provided in at least two or more vectors. Any of the vectors may be inducible (e.g., antibiotic induction, growth medium induction). Any of the vectors may further comprise a random tag or random nucleic acid sequence for later identification. Any of the vectors may express one or more markers for selection (e.g., antibiotic selection), so that following transfection/infection, transfected or infected cells may be selected by the selectable marker. Any of the vectors may further express one or more markers or marker proteins for characterization (e.g., proteins such as histidine, glutathione S-transferase, maltose binding protein, green fluorescent protein, APEX, etc.). In one embodiment, at least the OSKM factors (Oct3/4, Sox2, Klf4, cMyc) are provided via one or more vectors to cells from the sample. In one embodiment, the OSKM factors (Oct3/4, Sox2, Klf4, cMyc) and one or more additional transcription factors (e.g., Lin28, Nanog, or Lin28 and Nanog) are provided via one or more vectors to cells from the sample. The one or more vectors may be provided by the same carrier, or by different carriers. In one embodiment, cMyc is not provided as one of the pluripotency-associated transcription factors, as it is known to promote tumor growth. In one embodiment, transcription factors Esrrβ, Oct4, and Sox2 (with or without one or more additional transcription factors) are provided via one, or more than one vector, to cells from the sample, either by the same carrier, or by different carriers. In some embodiments, the one or more vectors are provided (with the same carrier, or by different carriers), and said carrier is then delivered to the cells under suitable settings or conditions for electroporation, infection, transduction or transfection, as is understood in the relevant field. The cells are supported in a suitable culture medium for delivery of the vector with the suitable carrier. Following transfection/infection with the vector (and/or the suitable carrier), which may or may not be repeated, transfected or infected cells may be selected by the selectable marker. Typically, the sample is provided on a tissue culture plate, and cells therefrom are grown for one to several passages in serum containing media before the pluripotency-associated genes on the one or more vectors are delivered to the cells. It is understood that the sample cells, the type of vector, and/or the chosen carrier will help dictate the settings or conditions for initial plating of cells, for passaging, and for delivery of the vector to the cells (e.g., via electroporation, infection, transduction or transfection), and will utilize known and/or suitable microbiologic tools, as understood by the skilled artisan. Examples of suitable representative methods of delivery of a suitable carrier containing a suitable vector to cells, utilized to induce pluripotency in a manner described herein, are provided at least in: *Cell*, Nov. 30, 2007, 131(5):861-72; *PNAS*, Feb. 26, 2008, 105(8):2883-2888; *Nature*, Aug. 7, 2009, 460(7259): 1145-1148; *Cell Stem Cell*, Nov. 5, 2010, 7(5):618-630, all of which are incorporated herein by reference in their entirety, and to the maximal extent allowable.

In one embodiment, pluripotency-associated transcripts are provided as mRNA mimetics, and are delivered to the sample containing cells, and/or cells from the sample, as depicted in block 20. The mRNA provides several advantages over use of DNA, or other approaches, for gene transfer and expression in cells, such as the lack of any requirement for nuclear localization or transcription, and the nearly negligible possibility of genomic integration of the delivered nucleic acid sequence. The mRNA mimetics will include any one or more of transiently expressed mRNA, modified mRNA (mmRNA), sequence-engineered mRNA (semRNA), and/or sequence-engineered mmRNA (semmRNA). The mRNA mimetics are generally synthesized using as a template one or more constructs (e.g., expression vector), each encoding at least a sequence for the open reading frame (ORF) of one or more human genes for the pluripotent-associated transcription factors (e.g., the OSKM transcription factors and/or the alternative transcription factors). The one or more constructs may be one or more plasmid constructs, an example of which is a plasmid construct synthesized, sequence verified, and supplied by a synthesis service, manufacturer, laboratory, etc. One suitable supplier is GenScript, in Piscataway, N.J. With use of a suitable construct, such as a plasmid, the plasmid may be linearized before the mRNA is transcribed under suitable transcription conditions, and is purified. The synthesized RNA is typically purified and quantitated (e.g., via spectrophotometer) before being provided in an RNA cocktail, in which the RNA cocktail contains at least the RNA suitable as pluripotency-associated transcripts (e.g., OSKM transcription factors and/or the suitable alternative transcription factors) for inducing pluripotency in the cells obtained from the sample, as described herein. In some embodiments, the RNA is further modified (either before or after synthesis) before providing in the RNA cocktail (e.g., by DNase treatment, and/or by incorporating modified ribonucleoside bases during RNA synthesis, such as 5-methylcytidine for cytidine, or pseudouridine for uridine). The RNA cocktail, or at least one of the synthesized RNA, may further comprise a random tag, or random nucleic acid sequence, that is associated with or is synthesized with at least one of the RNA, the tag being useful for later identification. The RNA cocktail may further comprise an additional RNA transcript for expression of one or more markers or marker proteins for characterization (e.g., proteins such as histidine, glutathione S-transferase, maltose binding protein, green fluorescent protein, APEX, etc.). In some embodiments, the synthesized RNA in the RNA cocktail is not modified, but is selected for optimum secondary structure using a method of correlated stem-loop prediction based on considering all stem-loop conformations, and averaging their interaction energy, and maximizing the minimum free energy of the RNA nucleotide sequence. An example of a suitable and representative method, utilized to prepare and provide mRNA mimetics in a manner described herein, is provided at least in: *Nucleic Acids Research*, 2013, 41(6):e73, which is incorporated herein by reference in its entirety, and to the maximal extent allowable. In one embodiment, the RNA cocktail includes RNA of at least the OSKM factors (Oct3/4, Sox2, Klf4, cMyc). In one embodiment, the RNA cocktail includes RNA of at least the OSKM factors (Oct3/4, Sox2, Klf4, cMyc) and RNA of one or more additional transcription factors (e.g., Lin28, Nanog, or Lin28 and Nanog). In one embodiment, the RNA cocktail does not include RNA of cMyc, as this factor is known to promote tumor growth. In one embodiment, the RNA cocktail includes RNA of at least the transcription factors Esrrβ, Oct4, and Sox2 (with or without one or more additional transcription factors). The RNA cocktail may be provided to the cells by a carrier (e.g., lipid carrier, cationic lipid vehicles), in which the carrier is initially incubated with the RNA cocktail, and the carrier containing the RNA cocktail is then provided and incubated with the cells under suitable transfection and/or electroporation conditions. Typically, the sample is provided on a tissue culture plate and cells therefrom are grown for one to several passages in serum containing media before the RNA cocktail contained in the carrier is delivered to the cells for transfection and/or electroporation. In some embodiments, the sample is grown on gelatin coated dishes with fibroblast media. It is understood that the cells from the sample, and/or the carrier chosen, will help dictate the conditions for initial plating of the cells, for passaging, and for delivery of the pluripotency-associated transcripts to the cells (via transfection and/or electroporation), and will utilize known and/or suitable microbiologic tools, as understood by the skilled artisan. The type of cells from the sample may be initially determined by immunostaining and/or other known procedures. Transfected or infected cells may be selected by a selectable marker. Examples of suitable representative methods of providing the RNA cocktail and/or delivery of an RNA cocktail are described at least in: *Cell Stem Cell*, Nov. 5, 2010, 7(5):618-630; *Biochem. Biophys. Res. Commun.* Mar. 26, 2010, 394(1):189-93; *Int. J. Mol. Sci.* Nov. 27, 2014, 15:21840-21864, all of which are incorporated herein by reference in their entirety, and to the maximal extent allowable.

Treatment of the sample, and or cells of the samples, with the requisite pluripotency-associated genes and/or transcripts (e.g., via mRNA mimetic cocktail or otherwise), may be for a few hours, up to 12 hours, or may include several days of treatment and incubation to express endogenous pluripotency-associated genes and/or transcripts (block 21, FIG. 2). This may, in some embodiments, include additional delivery of the requisite pluripotency-associated genes and/or transcripts (e.g., via mRNA mimetic cocktail or otherwise) to the cells, and/or removal of the carrier, and/or further incubation of the cells for a few days to several days after the one or more treatments with the requisite pluripotency-associated genes and/or transcripts (e.g., via mRNA mimetic cocktail or otherwise).

Referring again to the conditioning step of block 12 of FIG. 1 and as outlined in block 20 of FIG. 2, another representative conditioning process to provide the rejuvenated cells as described herein may comprise a somatic cell reprogramming or rejuvenating process involving overexpression of a human telomerase catalytic subunit (hTERT). In some embodiments, this may include inactivation of another path, such as pRB/p16$^{INK4a}$, but it not typically required for cells containing fibroblasts. Here, a construct containing hTERT is introduced to cells, the hTERT may be contained as cDNA and inserted in a suitable vector, with or without utilizing a carrier, the vector may be a plasmid, or the like, as described above, including one having a selectable marker. Sample cells may be transfected with the vector, and/or transduced/infected/co-precipitated with a carrier containing hTERT in a retroviral construct. Following transduction/transfection/infection, which may or may not be repeated, transduced or transfected or infected cells may be selected by the selectable marker. These and other examples known in the art may be utilized to introduce hTERT and induce overexpression in the sample cells, some of which are described at least in: *J. Biomed. Sci.*, Nov. 5, 2010, 17:64; *Cancer Research* 2006, 66(7):3531-3540, each of which is incorporated herein by reference in its entirety, and to the maximal extent allowable.

Upon performing any of the conditioning processes outlined above, including blocks 20 and 21 of FIG. 2, rejuvenated cells, as described herein, are generated, as depicted in block 22, FIG. 2. The rejuvenated cells may, in one or more embodiments, be referred to as induced pluripotent stem cells, or iPSCs, having or capable of being characterized as pluripotent stem cells, being taken from an older or adult tissue (e.g., skin and/or hair), and being genetically modified to behave like an embryonic stem cell, with an ability to differentiate into and/or form an adult cell type, as is further described herein. The rejuvenated cells may also, in one or more embodiments, be referred to as overexpressing cells, having or capable of being characterized as cells with increased telomere length and replicative capacity, and/or improved metabolism and mitochondrial function, and/or a reduction (e.g., significant reduction) in stress-induced premature cell senescent markers (via expression/overexpression of the one or more proteins, such as described above).

In some embodiments, generation of the rejuvenated cells, when reprogrammed as embryonic-like stem cells or iPSCs, may include introducing feeder cells to the cells that were initially delivered the pluripotency-associated genes and/or transcripts (e.g., the sample cells, or the original cells, or the old cells, or the older cells). This typically includes introducing the cells of block 21 to a feeder layer of cells (e.g., embryonic fibroblasts, irradiated and/or inactivated cells, and/or mitomycin-treated cells), and/or providing the sample cells on a non-adherent culture dish, and maintaining in an enriched culture condition for up to several days, or up to a few weeks, or one month. The enriched culture condition may include, and often includes, serum and one or more growth factors, such as human fibroblast growth factor (hFGF), basic hFGF (bhFGF), and/or human stem cell factor (hSCF), with suitable media changes.

Rejuvenated cells provide a distinct morphology that differs from the cells of the sample. The pluripotent cells or iPSCs that arise under these conditions that form the iPSCs often form colonies (akin to human embryonic stem cell colonies), express human embryonic stem cell genes (e.g., consensus signature genes), and are immunoreactive when using consensus human embryonic stem cell surface antigens, such as TRA-1-81, TRA-1-61, and SSEA-4, as examples. The rejuvenated cells that arise from overexpression of one or more proteins often exhibit enhanced replicative capacity, in addition to one or more of increased telomere length, improved metabolism and mitochondrial function, and reduction in stress-induced premature cell senescent markers.

From the generated rejuvenated cells, certain clones are picked (e.g., mechanically) and/or selected (e.g., via a selectable marker) in block 23. Cells and/or clones may be selected that: (i) exhibit a pluripotency marker (e.g., utilizing an immunocytochemistry marker for at least one of the pluripotent-associated transcription factors, such as the OSKM transcription factors and/or the alternative transcription factors (block 26); (ii) exhibit a high expression of human telomerase reverse transcriptase or the catalytic subunit (hTERT) (block 26); and/or (iii) exhibit a distinct morphology and growth rate that resemble, or are similar to, human embryonic stem cells (block 26); and/or (iv) exhibit an up-regulation of embryonic stem cell markers (block 25, block 26); and/or (v) undergo differentiation (block 27, block 28); and/or (vi) undergo embryoid body formation (block 27, block 28); and/or (vii) exhibit developmental potential using a teratoma formation assay (block 27, block 28); and/or (viii) exhibit increased telomere length; and/or (ix) exhibit increased replicative capacity; and/or (x) exhibit a reduction in a cell senescent marker. Characterization for embryoid body formation generally includes appropriate culture conditions with one or more tissue specific growth factors, as is understood in the relevant art, and/or use of coated tissue culture plates. Cells and/or clones may also be selected/picked that display, by semi-quantitative reverse transcriptase-PCR (RT-PCR), and/or microarray expression analysis, and/or flow cytometry, protein and/or gene expression resembling and/or representative of such cells (e.g., human embryonic stem cell gene consensus genes and/or their proteins and/or high expression of the one or more proteins utilized to induce rejuvenation) (block 25). RT-PCR may be performed to examine whether a cell marker sequence and/or gene (ones expressed by human embryonic stem cells, and/or ones included in or with the original vector/construct/cocktail) is expressed in the rejuvenated cells. Cells and/or clones may include ones in which there is efficient silencing of a virus transcription factor construct (when a viral carrier is used). In one or more embodiments, cells are selected that exhibit an up-regulation of hTERT, and/or have a high expression (over-expression) of hTERT. Examples of suitable representative methods of generating and selecting/picking cells (or iPSCs) are described at least in: *Cell*, Nov. 30, 2007, 131(5):861-72; *PNAS, Feb.* 26, 2008, 105(8):2883-2888; *Nature, Aug.* 7, 2009, 460(7259):1145-1148; *Cell Stem Cell*, Nov. 5, 2010, 7(5):618-630, all of which are incorporated herein by reference in their entirety, and to the maximal extent allowable.

As depicted in FIG. 2, selected rejuvenated cells may be characterized and/or further analyzed as shown in blocks 25 and 26. Analysis of the rejuvenated cells may include morphological analysis (block 26). Analysis of the rejuvenated cells may include compositional analysis (e.g., membrane composition, intracellular composition, protein composition, nucleic acid composition, etc.) (block 26). Further analysis may include a comparative analysis of the selected rejuvenated cells, or one or more components thereof, against the sample cells or original cells from which they originated from. Rejuvenated cells that are selected, as described above, may be stored (block 24), expanded (block 28), modified (block 27), and/or utilized (block 29). Any one or more components, and/or combinations thereof, obtained from and/or derived from the rejuvenated cells whether analyzed, and/or stored, and/or expanded, and/or modified, may be provided in a cosmetic composition as described herein (block 29).

Figure 3:
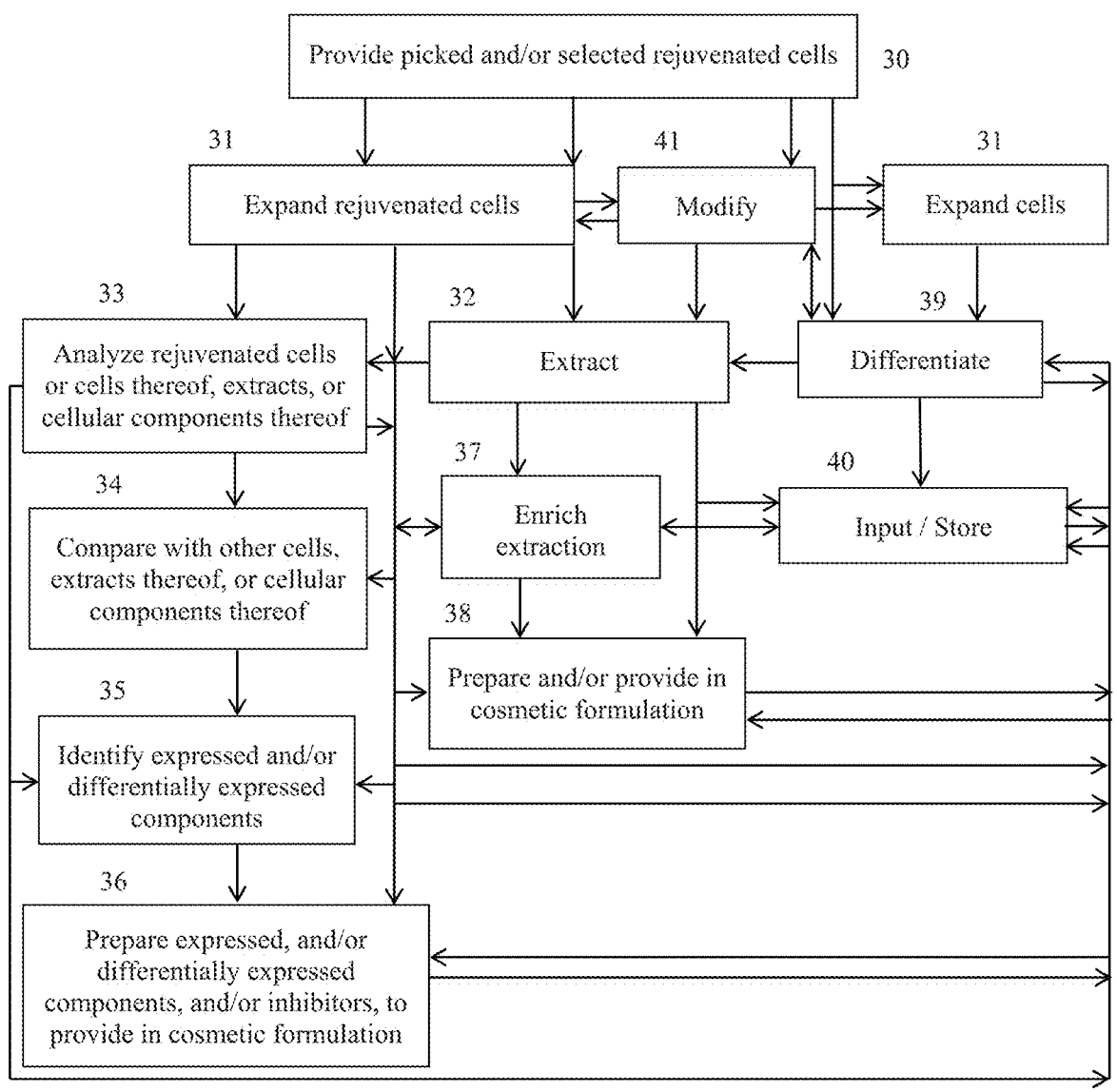
FIG. 3 depicts a third representative embodiment described herein.

Utilization, analyses, modification of, and/or expansion of rejuvenated cells are depicted in FIG. 3, in which selected rejuvenated cells provided in block 30, and subsequently expanded (block 31), modified (block 41), extracted (block 32), and/or analyzed (blocks 33, 34, 35). The compositional analyses may comprise analyses of whole cells, whole cell extracts, one or more enriched extracts, and/or one or more of cellular DNA, cellular RNA of one or more or all types, gene sequences, polypeptides, proteins/peptides, organelles, cellular compartments. In one or more embodiments, analysis of the selected or picked rejuvenated cells may initially include an expansion or growth thereof, as depicted in block 31. Expansion may not always be necessary. In one or more embodiments, the analysis of the selected or picked rejuvenated cells may further include a disassociation and/or extraction, as depicted in block 32. The extraction may be a whole cell extraction, or an extraction of one or more of nucleic acids (DNA, mRNA, miRNA, long ncRNA), proteins/peptides, exosomes (and/or their cargo), metals, hormones, prohormones, lipids, fatty acids, metabolites, vitamins, ions, small molecules, carbohydrates, polysaccharides, and/or proteoglycans, or variations thereof, or other extraction of one or more cellular components, and/or cellular compartments, and/or one or more secreted components and/or compartments. The extraction may be further analyzed (block 33), such as for identification of and/or absence of one or more of the cellular components, and/or one or more of the cellular compartments, and/or one or more of the secreted components and/or compartments.

In one or more embodiments, the rejuvenated cells when grown and/or expanded (block 31), are disassociated, harvested and lysed, to provide whole cell lysates (block 32). In one or more embodiments, the whole cells lysates may be provided to the cosmetic formulation described herein, as depicted in block 38.

In one or more embodiments, the rejuvenated cells, when grown and/or expanded, are disassociated, harvested and/or lysed, and may be enriched (block 37) for purposes of providing to the cosmetic formulation described herein, as depicted in block 38. The provided component from such a process comprises at least one enriched pool of one or more cellular components and/or cellular compartment, including but not limited to proteins and/or peptides, cellular nucleic acids (DNA, and/or mRNA, and/or miRNA, and/or long ncRNA), and/or cellular RNA (mRNA and/or miRNA and/or long ncRNA), and/or exosomes (and/or their cargo), metals, hormones, prohormones, lipids, fatty acids, metabolites, vitamins, ions, small molecules, carbohydrates, polysaccharides, and/or proteoglycans, or variations thereof. In one or more embodiments, the rejuvenated cells are expanded (block 31), extracted (block 32), and the extraction is enriched (block 37), in which the extraction comprises an enriched pool of one or more of the cellular components, and/or one or more of the cellular compartments. The enriched pool or pools may be further analyzed (block 33), such as for identification of and/or absence of one or more components. The enriched pool or pools may be further prepared and provided to the cosmetic formulation described herein, as depicted in block 38. Preparation may include a type of partial purification, and/or isolation, and/or providing in a suitable solvent for solubility, structural integrity, and biologic activity.

Analysis of the rejuvenated cells, as described above, may further comprise extracting DNA, amplifying the DNA, sequencing the amplified DNA, and identifying DNA sequences, particularly genes found in the rejuvenated cells that are associated with healthy and/or young skin and/or hair, and/or that are identified and/or predominate in the rejuvenated cells (e.g., genes for various types of skin and/or hair proteins, such as collagen, elastin, fibronectin, keratin, laminin, filaggrin, corneodesmosin, etc.). In addition, or as an alternative, the analysis may comprise or may further comprise extracting proteins (e.g., from the entire cell, or compartmentally from different organelles and/or locations), identifying one or more proteins in their native and/or modified form (e.g., via mass spectrometry-based techniques, and/or via antibodies or the enzyme-linked immunosorbent assay, and/or gel electrophoresis by Western blot, and/or two-dimensionally), with or without protein separation techniques, which may or may not be accompanied by sequencing of the protein, Edman degradation, chromatography, and/or separation techniques, to provide one or more proteins and/or peptides found in the rejuvenated cells that are associated with healthy and/or young skin and/or hair, and/or that are identified and/or predominate in the rejuvenated cells (e.g., proteins, such as collagen, elastin, fibronectin, keratin, filaggrin, corneodesmosin, laminin, etc.). In addition, or as an alternative, proteins and/or peptides secreted by the rejuvenated cells may be collected and analyzed in a known manner, and/or in a similar manner as describe above, to provide one or more proteins and/or peptides found in the rejuvenated cells that are associated with healthy and/or young skin and/or hair, and/or that are identified and/or predominate in the rejuvenated cells (e.g., proteins, such as collagen, elastin, fibronectin, keratin, filaggrin, corneodesmosin, laminin, etc.). In addition, or as an alternative, analysis may comprise or may further comprise profiling and/or identifying small RNA and/or miRNAs of the rejuvenated cells, or one or more of the most predominant small RNA and/or miRNAs, utilizing known techniques, to provide one or more small RNA and/or miRNAs found in the rejuvenated cells that are associated with healthy and/or young skin and/or hair, and/or that are identified and/or predominate in the rejuvenated cells (e.g., proteins, such as collagen, elastin, fibronectin, keratin, filaggrin, corneodesmosin, laminin, etc.). Small RNA/miRNA may be analyzed using known techniques, or high-throughput sequencing platforms, such as extracting total RNA, and fractionating/profiling small or miRNAs, and ligating/amplifying and/or sequencing, which may or may not include 454 sequencing (e.g., utilizing Roche 454 Pyrosequencer) and/or Solexa/Illumina sequencing and/or SOLiD sequencing, and/or microRNA arrays (e.g., Agilent), and/or processing reads, and/or mapping sequence reads to a database of known RNAs (e.g., in library), and/or in which expression levels are, for example, determined by the number of sequence reads mapped to known miRNAs, and normalized by the total number of miRNA reads in the library, which is described at least in: Wu, et al., J. Biomedicine and Biotechnology 2011:1-7; Hafner, et al., Methods 2008; 44:3-12; Rajasethupathy, et al., Neuron 2009; 63:803-817, each of which is incorporated herein in its entirety and to the maximal allowable. Small RNAs may be sorted and further profiled, such as by utilizing a photoactivatable ribonucleoside-enhanced cross-linking and immunoprecipitation method (PAR-CLIP) that captures AGO2 binding to mRNAs, and which may be utilized to identify a full range of small and/or miRNA target sites, which is described at least in Hafner, et al., Cell 2010; 141:129-141, incorporated herein in its entirety and to the maximal allowable. In addition, or as an alternative, long ncRNA may be analyzed and/or extracted using known techniques, to provide one or more long ncRNA found in the rejuvenated cells that are associated with healthy and/or young skin and/or hair, and/or that are identified and/or predominate in the rejuvenated cells. Long ncRNA may be isolated by collecting total RNA from an extract, and/or by RNA immunoprecipitation (RIP) techniques performed with or without cross-linking (before or after making cell extracts) followed often by dissociation from chromatin. Long ncRNA may be identified from total RNA, or one or more RNA pools, by amplification (e.g., RT-PCR), and/or by a microarray-based approach (e.g., microarray, tiling array), and/or next generation RNA sequencing of total RNA or one or more RNA pools, utilizing known sequencing techniques that generate reads, and/or in which expression levels are determined, for example, by the number of sequence reads mapped to known long ncRNAs (e.g., in a library), and normalized by the total number of long ncRNAs reads in the library, such as described above, and/or as described at least in Lee, et al., Cell & Bioscience 2012; 2:37, and/or references therein, all of which are incorporated herein in their entirety and to the maximal allowable.

In one or more embodiments, from the compositional analysis of the rejuvenated cells which includes analysis and identification of one or more components selected from the group consisting of genes, proteins, RNA (block 35), carbohydrates, polysaccharides, proteoglycans, sugars, metabolites, lipids, prohormones, hormones, fatty acids, vitamins, metals, ions, co-factors, small molecules, at least some of these one or more components identified in the rejuvenated cells are utilized, and in some embodiments, what is identified, or a portion thereof, is provided in the cosmetic formulation described herein, as depicted in block 36. For example, in one or more embodiments, from identified genes, at least some of the identified translatable genes are to design, generate, and/or synthesize proteins and/or peptides in a suitable form for the cosmetic formulation, such as for solubility, structural integrity, and/or longevity. In addition, or as an alternative, in one or more embodiments, from identified proteins and/or peptides, at least some of the identified proteins and/or peptides are directly utilized from the rejuvenated cells (e.g., extracted, purified), and/or are utilized to design, generate, and/or synthesize proteins and/or peptides in a suitable form for the cosmetic formulation, such as for solubility, structural integrity, and/or longevity. In addition, or as an alternative, from the identified cellular RNA (e.g., mRNA, small RNA, miRNA, long ncRNA), at least some of the identified cellular RNA are directly utilized from the rejuvenated cells (e.g., extracted, purified), and/or are utilized to design, generate, and/or synthesize RNA in a suitable form for the cosmetic formulation (e.g., as mRNA mimetics, miRNA mimics, anti-miRNA mimics, siRNA mimics, long ncRNA mimetics, etc.). In addition, or as an alternative, from the other identified one or more components, at least some of the components are directly utilized from the rejuvenated cells (e.g. extracted, purified), and/or are utilized to design, generate, and/or synthesize the identified one or more components in a suitable form for the cosmetic formulation.

Any analysis of the rejuvenated cells in block 33 may further comprise an analysis and/or identification of one or more cellular components, or extract thereof, from original cells or sample cells (e.g., old cells, older cells, and/or cells from which the rejuvenated cells originated from), in the manner described above, and/or utilizing known or available techniques for identifying one or more cellular components, including, but not limited to, proteins and/or peptides, nucleic acid sequences, organelles, exosomes (and/or their cargo), metals, hormones, prohormones, lipids, fatty acids, metabolites, vitamins, ions, small molecules, carbohydrates, polysaccharides, and/or proteoglycans, or variations thereof, etc., of the original or sample cells. This provides compositional information about the original cells, or sample cells (cells from the original skin and/or hair sample). Such information about the original or sample cells may be utilized for comparison with compositional information obtained from and/or about the rejuvenated cells, or cells obtained therefrom. In some embodiments, the original sample of cells is from an older subject, a less healthy subject, and/or is a sample that has been damaged, and/or is aged. In one or more embodiments, the one or more cellular components, and/or extracts thereof, and/or proteins, peptides, and/or nucleic acids, and/or exosomes (and/or their cargo), and/or organelles, metals, hormones, prohormones, lipids, fatty acids, metabolites, vitamins, ions, small molecules, carbohydrates, polysaccharides, and/or proteoglycans, or variations thereof, therefrom, obtained from the original cells or sample cells, are compared with those of the rejuvenated cells (block 34). The comparison may include identifying, in block 35, one or more gene sequences, proteins or peptides, RNA (mRNA, small RNA, miRNA, long ncRNA, etc.), organelles, exosomes (and/or their cargo), metals, hormones, prohormones, lipids, fatty acids, metabolites, vitamins, ions, small molecules, carbohydrates, polysaccharides, proteoglycans, or variations thereof, in the rejuvenated cells that are in a lower amount. The comparison may also include identifying, in block 35, one or more gene sequences, proteins or peptides, RNA (mRNA, small RNA, miRNA, long ncRNA, etc.), organelles, exosomes (and/or their cargo), metals, hormones, prohormones, lipids, fatty acids, metabolites, vitamins, ions, small molecules, carbohydrates, polysaccharides, proteoglycans, or variations thereof, that are less expressed in the original cells or sample cells. The comparison may also include identifying, in block 35, one or more gene sequences, and/or proteins or peptides, and/or RNA (mRNA, small RNA, miRNA, long ncRNA, etc.), and/or organelles, and/or exosomes (and/or their cargo), metals, hormones, prohormones, lipids, fatty acids, metabolites, vitamins, ions, small molecules, carbohydrates, polysaccharides, and/or proteoglycans, or variations thereof, that are not expressed in the rejuvenated cells, and/or are not expressed in the original cells or sample cells. Additional comparisons may be made in view of what is known in the field and/or by the skilled artisan. In one or more embodiments, from the differentially expressed or differentially represented gene sequences, and/or proteins or peptides, and/or RNA, and/or organelles, and/or exosomes (and/or their cargo), metals, hormones, prohormones, lipids, fatty acids, metabolites, vitamins, ions, small molecules, carbohydrates, polysaccharides, and/or proteoglycans, or variations thereof, the most differentially expressed (e.g., providing the greatest difference between the rejuvenated cells, and the original cells or sample cells) are utilized to provide such proteins, peptides, RNA sequences (mRNA, small RNA, miRNA, and/or long ncRNA), organelles, exosomes (and/or their cargo), metals, hormones, prohormones, lipids, fatty acids, metabolites, vitamins, ions, small molecules, carbohydrates, polysaccharides, proteoglycans, or variations thereof, to the cosmetic formulation described herein, as depicted in block 36. In addition, or as an alternative, from the differentially expressed or differentially represented gene sequences, proteins or peptides, RNA, organelles, exosomes (and/or their cargo), metals, hormones, prohormones, lipids, fatty acids, metabolites, vitamins, ions, small molecules, carbohydrates, polysaccharides, proteoglycans, or variations thereof, some or all of the components that are differentially expressed are utilized to design, and/or generate recombinant, and/or synthetic components, in block 36, in which the generated recombinant, and/or synthetic components, represent, and/or mimic, and/or block, one or more of the components that are differentially expressed, and, in which the one or more recombinant, and/or synthetic components when prepared are in a suitable form for the cosmetic formulation, having, for example, suitable solubility, structural integrity, and/or longevity.

In one or more embodiments, an analysis at block 33 may comprise or may further comprise an analysis and/or identification of one or more cellular components, or extract thereof, of differentiated cells of block 39 (e.g., cells differentiated from the rejuvenated cells forming young or younger cells), which may be performed in the manner described above, and/or utilizing known or available techniques for identifying one or more cellular components, including, but not limited to, proteins, peptides, nucleic acid sequences, organelles, exosomes (and/or their cargo), metals, hormones, prohormones, lipids, fatty acids, metabolites, vitamins, ions, small molecules, carbohydrates, polysaccharides, proteoglycans, or variations thereof, of the differentiated young or younger cells of block 39. This provides compositional information about cells induced to differentiate from the rejuvenated cells. Such information may be utilized for comparison with compositional information obtained from and/or about the rejuvenated cells. Such information may be utilized for comparison with compositional information obtained from normal differentiated cells (cells that are naturally differentiated, and/or from a known differentiated cell line). Such information may also be utilized in whole or in part for comparison with compositional information obtained from and/or about the original cells or sample cells, or for comparison with the known (normal) differentiated cells. The comparison may include identifying, in block 35, one or more gene sequences, proteins, peptides, RNA species (mRNA, small RNA, miRNA, long ncRNA, etc.), organelles, exosomes (and/or their cargo), metals, hormones, prohormones, lipids, fatty acids, metabolites, vitamins, ions, small molecules, carbohydrates, polysaccharides, proteoglycans, or variations thereof, in the differentiated young or younger cells described herein that are in a lower amount. The comparison may also include identifying, in block 35, one or more gene sequences, and/or proteins or peptides, and/or RNA (mRNA, small RNA, miRNA, long ncRNA, etc.), and/or organelles, and/or exosomes (and/or their cargo), that are absent in the differentiated young or younger cells described herein. Additional comparisons may be made in view of what is known in the field and/or by the skilled artisan. In one or more embodiments, from the differentially expressed or differentially represented gene sequences, proteins, peptides, RNA species, organelles, exosomes (and/or their cargo), metals, hormones, prohormones, lipids, fatty acids, metabolites, vitamins, ions, small molecules, carbohydrates, polysaccharides, proteoglycans, or variations thereof, some or all of those differentially expressed (e.g., providing a difference or a greater difference between the differentiated young or younger cells and the rejuvenated cells from which the differentiated young or younger cells originated from) are utilized to provide such proteins, peptides, RNA sequences (mRNA, small RNA, miRNA, and/or long ncRNA), organelles, exosomes (and/or their cargo), metals, hormones, prohormones, lipids, fatty acids, metabolites, vitamins, ions, small molecules, carbohydrates, polysaccharides, proteoglycans, or variations thereof, to the cosmetic formulation described herein, as depicted in block 36. In addition, or as an alternative, from the differentially expressed or differentially represented gene sequences, proteins, peptides, RNA species, organelles, exosomes (and/or their cargo), metals, hormones, prohormones, lipids, fatty acids, metabolites, vitamins, ions, small molecules, carbohydrates, polysaccharides, proteoglycans, or variations thereof, some or all of the components that are differentially expressed are utilized to design, and/or generate recombinant, and/or synthetic components, in block 36, in which the generated recombinant, and/or synthetic components, represent, and/or mimic, and/or block, one or more of the components that are differentially expressed, and, in which the one or more recombinant, and/or synthetic components when prepared are in a suitable form for the cosmetic formulation, having, for example, suitable solubility, structural integrity, and/or longevity.

In one or more embodiments, the analyses described above (e.g., beginning at block 33 of FIG. 3) will provide a repertoire of small RNA and/or miRNA that are expressed. In addition, or as an alternative, the comparison described above (e.g., block 34 of FIG. 3) will provide a repertoire of small RNA and/or miRNA that are differentially expressed between the original cells, and (i) the rejuvenated cells, and/or (ii) cells that differentiate from the rejuvenated cells (e.g., block 39 of FIG. 3). Similarly, a comparison may be between the rejuvenated cells, and the cells that differentiate from rejuvenated cells (e.g., block 39). In addition, or as an alternative, a comparison may be between the differentiated young or younger cells described herein (e.g., characterized as keratinocytes or keratinocyte-like, and/or as melanocytes or melanocyte-like), and normal or known differentiated cells (e.g., normal or known keratinocytes, and/or normal and/or known melanocytes, respectively). Small RNA and/or miRNA are conserved non-coding small RNAs of about 10-150 nucleotides, and sometimes less than 50 nucleotides, or smaller, often acting as post-transcriptional inhibitors of gene expression. Several miRNA have been identified as pro-inflammatory miRNAs. These include miRNA 10(a), miRNA 21(-3p, -5p), miRNA-29, miRNA-146(a), miRNA-155(-3p, -5p)]. Inhibitors and/or anti-miRNA mimics may be used to disrupt and/or silence expression of the expressed pro-inflammatory miRNA, and/or the pro-inflammatory miRNA that are differentially expressed (e.g., expressed more in the original cells, or the sample cells; and/or expressed less and/or is absent in the differentiated cells of block 39, as compared with the original cells, and/or expressed less and/or is absent in the differentiated cells of block 39, as compared with the rejuvenated cells from which they were obtained). In one or more embodiments, anti-pro-inflammatory miRNA mimics, an inhibitor of such pro-inflammatory miRNA, and/or various combinations thereof, that target some or all of the expressed and/or differentially expressed miRNA are provided in the cosmetic formulation described herein. These antagonists and/or inhibitors may be used, for example, to disrupt the otherwise pro-inflammatory action of miRNA found to be present in the original cells, and/or found to have an increased expression in the original cells, as compared with the rejuvenated cells. Synthetic miRNA may be engineered in the laboratory, and/or chemically synthesized by a commercial manufacturer. Precursor molecules (pre-miRNA) for many pro-inflammatory miRNAs are presently and/or commercially available. Pro-inflammatory miRNA inhibitors, including ones based on small molecules, are available (commercially, or otherwise). In addition, anti-miRNA inhibitors are also available (commercially, or otherwise). These short oligonucleotides are preferably provided by and in a cationic lipid or liposome and/or polymer-based delivery vehicle, or are chemically modified to allow for cellular uptake when included in the formulation.

In one or more embodiments, the analyses described above (e.g., beginning at block 33 of FIG. 3) will provide a repertoire of mRNA that are expressed. In addition, or as an alternative, the comparison described above (e.g., block 34 of FIG. 3) will provide a repertoire of mRNA that are differentially expressed (e.g., between the original cells, and (i) the rejuvenated cells of block 34, and/or (ii) cells that differentiate from the rejuvenated cells of block 39, and/or other comparisons as described above). Short interfering RNA (siRNA) mimics may be used to disrupt and/or silence expression of one or more target mRNA transcripts. In one or more embodiments, siRNA mimics that target some or all of the expressed and/or differentially expressed mRNA are provided in the cosmetic formulation described herein, in which the target is an mRNA transcript found to be present in the original cells and less or absent in the rejuvenated cells, and/or is found to have an increased expression in the original cells as compared with the rejuvenated cells. In addition, or as an alternative, the target may be an mRNA transcript found to be absent in the differentiated young or younger cells of block 39 (as compared with the original cells), and/or is found to have a decreased expression in the differentiated young or younger cells of block 39, as compared with the rejuvenated cells, from which the differentiated cells of block 39 were obtained. Synthetic siRNA may be engineered in the laboratory, and/or chemically synthesized by a commercial manufacturer. These short oligonucleotides are preferably provided by and in a cationic lipid and/or polymer-based reagent, or are chemically modified to allow for cellular uptake when included in the formulation.

The analyses of sample (original) cells, selected rejuvenated cells, and/or differentiated young or younger cells (and/or any other analyses or comparisons described above) provides data about the sample or cell, and the subject from which the sample or cell is obtained. The data includes cellular data, DNA data, RNA data, gene data, protein/peptide/polypeptide data, extract data, and other data regarding one or more cellular components, and/or one or more cellular characteristics, morphology, etc. In addition, data may provide information about unique proteins/polypeptides, DNA, RNA and/or gene sequence(s) contained by the subject, the sample, and/or any cell therefrom, and/or about proteins/polypeptides, DNA, RNA and/or gene sequence(s) not contained by the subject, the sample, and/or any cell therefrom. All of said data may be stored, as depicted in FIGS. 1-3, and may be used to provide a unique cosmetic formulation for the subject. The data stored may be physical, such as in the form of cells, extracts, DNA, RNA, protein, polypeptide, exosome, etc. The data stored may be physical, such as in the form of paper. Such physical storage may be in a suitable storage environment (e.g., in vials stored in liquid nitrogen, in petri dishes, etc.). The data stored may be electronic and/or digital data, stored in a digital storage or memory, which may or may not be directly accessible by a central processing unit (CPU) of a computing device, and may or may not be under the control of the CPU.

Any information identified and/or obtained about the subject, the sample, and/or any cell therefrom, can be stored as electronic and/or digital data. Such data may be stored on a computer-readable medium such as memory of a storage device (e.g., RAM, or cache memory), and/or stored on the storage device (e.g., hard disk, floppy disk, magnetic disk, tape, CD-ROM, magneto-optical disks, fixed disks, recordable CD, DVD, recordable DVD (e.g., DVD-R, DVD+R, DVD-RW, DVD+RW, HD-DVD, or Blu-ray Disc), flash, and/or on other nonvolatile solid-state storage device, such as USB flash drive, solid state drive (SSD), battery-backed-up volatile memory, tape storage, reader, and other similar media utilized, known, and/or available in the art, and various combinations of these.

Generally, any of the preparations provided after expansion (block 31) and/or extraction (block 32) of the rejuvenated cells may be: (i) utilized directly to provide some or all of the cellular and/or secreted components to at least one cosmetic formulation described herein; and/or (ii) utilized to enrich some or all of the cellular and/or secreted components in order to provide the enriched component(s) to at least one cosmetic formulation described herein; and/or (iii) utilized to design and generate synthetic and/or mimetic components, and/or inhibitor thereof, for providing in at least one cosmetic formulation described herein; and/or (iv) stored in any of the forms described herein, including (i), (ii) and/or (iii). In some embodiments, the preparation, after expansion and/or extraction may be purified. In some embodiments, the preparation, after expansion and/or extraction may be enriched and/or purified. The preparation, after expansion and/or extraction may be further processed to isolate one or more of the components, such as but not limited to one or more polypeptides, proteins, nucleic acid sequences, organelles, and/or exosomes (and/or cargo therein). In one or more embodiments, a "purified" preparation may have at least about 70% of the one or more components in the preparation by weight, or at least about 85% of the one or more components in the preparation by weight, or more than about 85% of the one or more components in the preparation by weight.

It is noted that molecular biology tools described herein, including vector constructs, tissue culturing, extraction, enrichment, purification, amplification, and/or sequencing, as examples, will utilize known and/or existing tools and steps existing and/or known to one skilled in the art in the fields of molecular biology, including those utilized in microbiology, chemistry, biochemistry, genetic analysis, sequencing, recombinant DNA, polymerase chain reaction (PCR), oligonucleotide synthesis and modification, next generation and/or sanger nucleic acid sequencing, nucleic acid hybridization, and related fields, and that are within the skill of the artisan in the field. One or more conventional techniques may be used. Some of the techniques are described in at least the following documents, all of which are incorporated herein by reference in their entirety, and to the maximal extent allowable: Maniatis, et al., (1982, and updates through present) *Molecular Cloning: A Laboratory Manual*, Cold Spring Harbor Laboratory Press; Sambrook, et al., (2001, and updates through present), *Molecular Cloning: A Laboratory Manual*, Third Edition, Cold Spring Harbor Laboratory Press; Ausubel et al., *Current Protocols in Molecular Biology*, John Wiley & Sons (1987 and annual updates through present); Gait (Ed.) (1984, and updates through present) *Oligonucleotide Synthesis: A Practical Approach*, IRL Press; Eckstein (Ed.) (1991, and updates through present) Oligonucleotides and Analogues: A Practical Approach, IRL Press; Birren et al., (Eds.) *Genome Analysis: A Laboratory Manual* (1999, and updates through present) Cold Spring Harbor Laboratory Press. Kits, machines, and/or laboratories for applying many of the molecular biology tools and techniques described herein that are commercially and/or otherwise known and/or available to the skilled artisan may be utilized.

For identification and/or comparison of nucleic and/or amino acid sequences, as described herein, the process will often include aligning two sequences (e.g., between a known sequence and an extracted sequence; and/or between extracted rejuvenated cells sequence and extracted original sequence; and/or between extracted rejuvenated cells sequence and extracted differentiated young or younger sequence). Sequence alignment and comparison may be conducted using known or available algorithms provided in the art (e.g. Smith and Waterman, 1981, *Adv. Appl. Math.* 2:482; Needleman and Wunsch, 1970, *J. Mol. Biol.* 48:443; Pearson and Lipman, 1988, *Proc. Natl. Acad. Sci., USA,* 85:2444) and/or by computerized versions of these algorithms (e.g., Wisconsin Genetics Software Package Release 7.0, Genetics Computer Group, Madison, Wis.), including those publicly available (e.g., BLAST, FASTA, and ENTREZ, which is available through the National Institutes of Health, Bethesda, Md.), all representations and references of which are incorporated herein by reference in their entirety, and to the maximal extent allowable. In one or more embodiments, the percent identity may be at least 70%, which includes sequences that range from about 70% to about 99.99% identity to the indicated sequence(s), and includes all ranges or values in between. In some embodiments, the determination of percent identity is determined using an algorithm, such as an algorithm described herein. In some embodiments, sequence homology may be at least about 50% or more, and includes all ranges or values in between.

In one or more embodiments, the differentially identified and/or expressed DNA and/or gene sequences, provided in a suitable construct, are utilized to generate one or more recombinant proteins, and/or synthetic mRNA mimetics, and/or synthetic siRNA mimics, which, when expressed, are included in at least one cosmetic formulation described herein. In some embodiments, the at least one cosmetic formulation is for the subject who provided the original cells or sample cells from which rejuvenated cells (and/or differentiated young or younger cells) were generated/induced, which were utilized for differential expression. In some embodiments, the at least one cosmetic formulation is for a subject representative of and/or represented by a subject who provided the original cells or sample cells from which rejuvenated cells (and/or differentiated cells) were generated/induced, which were utilized for differential expression.

In one or more embodiments, the differentially identified and/or expressed DNA and/or gene sequences may be used to generate peptides and/or polypeptides, and/or synthetic mRNA(s), which are provided to the rejuvenated cells (e.g., block 41, FIG. 3), and/or utilized to selectively program and/or modify rejuvenated cells (e.g., see FIG. 2, block 23), and/or utilized to selectively express genes, protein(s) and/or RNA in the rejuvenated cells, and/or in differentiated young or younger cells that have differentiated from any of the rejuvenated cells described herein, any of which may also be provided in the cosmetic formulation described herein. And such cells and/or components thereof (e.g., that have been identified, expressed and/or extracted) may be periodically or regularly stored (e.g., FIG. 3, block 40).

In one or more embodiments, rejuvenated cells, generated as previously described (e.g., FIG. 1, FIG. 2), are expanded (block 31, FIG. 3), and differentiated into keratinocytes (block 39, FIG. 3). This may include subcloning of selected rejuvenated cells, or of colonies formed therefrom (such as from a suspension culture, and/or from generated embryonic bodies), and providing on a gelatinous basement-like preparation, and/or on an extracellular matrix-like mixture, such as ones comprising collagen, proteoglycans, and growth factors (e.g., MATRIGEL®, from Corning Life Sciences, or CULTREX®, from Trevigen, Inc.), followed by providing a known differentiation-inducing media (e.g., for keratinocytes, including one or more of a bone morphogenetic protein (BMP), such as BMP-4, retinoic acid, and/or ascorbic acid). Quantitative RT-PCR may be performed to identify and/or determine when the differentiated cells express keratinocytes markers. Immunofluorescence and/or flow cytometry may also be utilized to characterize the keratinocytes. Examples of suitable representative methods of generating and selecting/picking pluripotent cells, with differentiation into keratinocytes, are described in at least: *Cell Stem Cell, Sep.* 11, 2008, 3(3):340-345; *Curr. Pathobiol.,* Mar. 31, 2013, 1:119-128; *J. Investigative Dermatology,* 2014, 134:e23, each of which is incorporated herein by reference in its entirety, and to the maximal extent allowable.

In one or more embodiments, rejuvenated cells generated as previously described (e.g., FIG. 1, FIG. 2), are expanded (block 31, FIG. 3), and differentiated into melanocytes. This may include similar steps, as described above, including selection of rejuvenated cells, or colonies formed therefrom (such as from a suspension culture, and/or from generated embryonic bodies), and/or subcloning, and providing on fibronectin coated plates, and/or on an extracellular matrix-like mixture (e.g., comprising fibronectin), followed by providing suitable and known differentiation-inducing media (e.g., for melanocytes, by including one or more growth factors, such as BMP-4, SCF, endothelin-3, bFGF, and Wnt3a, and/or conditioned media from L-WNt3a cells, and/or conditioned media from L-Wnt3a cells, with or without other factors, such as linoleic acid, bovine serum albumin, ascorbic acid). Quantitative RT-PCR may be performed to identify and/or determine when the differentiated cells express melanocytic markers. Immunofluorescence and/or flow cytometry may also be utilized to characterize the melanocytes, and melanosomes. Examples of representative and suitable methods of generating and selecting/picking pluripotent cells, and differentiation into melanocytes or melanosomes, are described in at least: *Am. J. Pathology,* June 2006, 168(6):1879-1888; *J. Investigative Dermatology,* 2011(131):2458-2466, each of which is incorporated herein by reference in its entirety, and to the maximal extent allowable.

In one or more embodiments, the differentiated young or younger cells are considered rejuvenated cells, having differentiated from the rejuvenated cells that were considered young cells. One or more components and/or whole cell extracts and/or enriched extracts of the differentiated young or younger cells may be provided to at least one cosmetic formulation described herein.

Any of the differentiated young or younger cells and/or components thereof may be stored (block 40), and/or modified (block 41), and/or extracted, and/or enriched (e.g., providing any one or more of whole cells extracts, DNA, RNA, proteins, exosomes and/or cargo thereof, etc.), metals, hormones, prohormones, lipids, fatty acids, metabolites, vitamins, ions, small molecules, carbohydrates, polysaccharides, proteoglycans, or variations thereof, as depicted blocks 32, 34, 35, 36, 37.

In one or more embodiments, differentiated young or younger cells, which may be expanded, are harvested and lysed, to provide whole cell lysates (block 32). The whole cell lysates may be provided to at least one cosmetic formulation described herein, as depicted in block 38.

In one or more embodiments, differentiated young or younger cells, which may be expanded, are harvested and lysed, and further enriched to provide an enriched extraction (block 37). The enriched extraction may comprise an enriched pool(s) of any one of, or more than one of: proteins and/or peptides, cellular RNA (mRNA and/or small RNA and/or miRNA and/or long ncRNA), and/or exosomes (and/or cargo thereof), metals, hormones, prohormones, lipids, fatty acids, metabolites, vitamins, ions, small molecules, carbohydrates, polysaccharides, proteoglycans, or variations thereof. The enriched pool(s) may be prepared (all or a portion thereof) and provided to at least one cosmetic formulation described herein (block 38). The enriched pool(s) may be further analyzed (block 33, and/or 34 and 35) and/or further enriched (block 37), in which an enriched preparation (all or a portion thereof) is provided to at least one cosmetic formulation described herein, as depicted in block 38. The preparations may comprise providing the extraction, or enriched extraction, in a suitable form (e.g., solubility, structural integrity, and/or longevity) for the at least one cosmetic formulation.

In one or more embodiments, a cosmetic formulation described herein is individualized and/or personalized for a subject and comprises any of a combination of mRNA mimetics and/or one or more recombinant proteins and/or peptides as described above, in combination with any one or more of miRNA mimetic cocktail, siRNA mimetic cocktail, and/or ncRNA mimetic cocktails, in which such cocktails provide anti-aging properties, and are identified by any of the comparisons (differential expressions) described herein.

In one or more embodiments, a cosmetic formulation described herein is individualized and/or personalized for a subject, the cosmetic formulation comprising at least:

Cell extract of cells from the subject or a representative of the subject, the cells from the subject or a representative of the subject being reprogrammed and characterized as rejuvenated cells (via an induction and/or reprogramming process, or expression/overexpression process), and the cell extract obtained from the rejuvenated cells.

In one or more embodiments, a cosmetic formulation described herein is individualized and/or personalized for a subject, the cosmetic formulation comprising at least:

Cell extract of cells obtained from and/or representative of and/or embodying certain cells of the subject, the certain cells being cells from hair and/or skin, the certain cells being reprogrammed and characterized as rejuvenated cells (via an induction and/or reprogramming process, or expression/overexpression process), and the cell extract obtained from the rejuvenated cells.

In one or more embodiments, a cosmetic formulation described herein is individualized and/or personalized for a subject, the cosmetic formulation comprising or further comprising at least:

Enriched cell extract of cells from the subject or a representative of the subject, the cells from the subject or a representative of the subject being reprogrammed and characterized as rejuvenated cells, the cell extract obtained from the rejuvenated cells (via a reprogramming process, or expression/overexpression process), and the cell extract being enriched for one or more of cellular RNA (mRNA, miRNA, and/or long ncRNA), peptides, polypeptides, exosomes and/or cargo thereof, metals, hormones, prohormones, lipids, fatty acids, metabolites, vitamins, ions, small molecules, carbohydrates, polysaccharides, proteoglycans, or variations thereof.

In one or more embodiments, a cosmetic formulation described herein is individualized and/or personalized for a subject, the cosmetic formulation comprising at least:

Enriched cell extract of cells obtained from and/or representative of and/or embodying certain cells of the subject, the certain cells being cells from hair and/or skin, the certain cells being reprogrammed and characterized as rejuvenated cells (via a reprogramming process, or expression/overexpression process), the cell extract obtained from the rejuvenated cells, and the cell extract being enriched for one or more of cellular RNA (mRNA, small RNA, miRNA, and/or long ncRNA), peptides, polypeptides, exosomes and/or cargo thereof, metals, hormones, prohormones, lipids, fatty acids, metabolites, vitamins, ions, small molecules, carbohydrates, polysaccharides, proteoglycans, or variations thereof.

In one or more embodiments, a cosmetic formulation described herein is individualized and/or personalized for a subject, the cosmetic formulation comprising or further comprising at least:

Cell extract of differentiated cells, the differentiated cells having been initially reprogrammed and characterized as rejuvenated cells (via a reprogramming process, and/or expression/overexpression process) from original cells from the subject or a representative of the subject, and thereafter induced from the rejuvenated cells into the differentiated cells, the differentiated cells being characterized as keratinocytes, keratinocyte-like cells, melanocytes, and/or melanocyte-like cells, endocrine cells, and/or endocrine cell-like cells, immune cells, and/or immune cell-like cells, endothelial cells, and/or endothelial cell-like cells, and the cell extract obtained from the differentiated cells.

In one or more embodiments, a cosmetic formulation described herein is individualized and/or personalized for a subject, the cosmetic formulation comprising or further comprising at least:

Cell extract of differentiated cells, the differentiated cells having been initially obtained from and/or representative of and/or embodying certain cells of the subject, the certain cells being cells from hair and/or skin, the certain cells being reprogrammed and characterized as rejuvenated cells (via a reprogramming process, and/or expression/overexpression process), and thereafter induced into the differentiated cells, the differentiated cells being characterized as keratinocytes, keratinocyte-like cells, melanocytes, and/or melanocyte-like cells, endocrine cells, and/or endocrine cell-like cells, immune cells, and/or immune cell-like cells, endothelial cells, and/or endothelial cell-like cells, or other skin cell type and the cell extract obtained from the differentiated cells.

In one or more embodiments, a cosmetic formulation described herein is individualized and/or personalized for a subject, the cosmetic formulation comprising or further comprising at least:

Enriched cell extract of differentiated cells, the differentiated cells having been initially reprogrammed and characterized as rejuvenated cells (via a reprogramming process, and/or expression/overexpression process) from original cells from the subject or a representative of the subject, and thereafter induced from the rejuvenated cells into the differentiated cells, the differentiated cells being characterized as keratinocytes, keratinocyte-like cells, melanocytes, and/or melanocyte-like cells, endocrine cells, and/or endocrine cell-like cells, immune cells, and/or immune cell-like cells, endothelial cells, and/or endothelial cell-like cells, or other skin cell type, the cell extract obtained from the differentiated cells, and the cell extract being enriched for one or more of cellular RNA (mRNA, small RNA, miRNA, and/or long ncRNA), peptides, polypeptides, exosomes and/or cargo thereof, metals, hormones, prohormones, lipids, fatty acids, metabolites, vitamins, ions, small molecules, carbohydrates, polysaccharides, proteoglycans, or variations thereof.

In one or more embodiments, a cosmetic formulation described herein is individualized and/or personalized for a subject, the cosmetic formulation comprising or further comprising at least:

Enriched cell extract of differentiated cells, the differentiated cells initially obtained from and/or representative of and/or embodying certain cells of the subject, the certain cells being cells from hair and/or skin, the certain cells being reprogrammed and characterized as rejuvenated cells (via a reprogramming process, or expression/overexpression process), and thereafter induced from the rejuvenated cells into the differentiated cells, the differentiated cells being characterized as keratinocytes, keratinocyte-like cells, melanocytes, and/or melanocyte-like cells, the cell extract obtained from the differentiated cells, and the cell extract being enriched for one or more of cellular RNA (mRNA, small RNA, miRNA, and/or long ncRNA), peptides, polypeptides, exosomes and/or cargo thereof, metals, hormones, prohormones, lipids, fatty acids, metabolites, vitamins, ions, small molecules, carbohydrates, polysaccharides, proteoglycans, or variations thereof.

In one or more embodiments, a cosmetic formulation that is individualized and/or personalized for the subject comprises, or further comprises, one or more of:

One or more cellular components, such as RNA (mRNA, small RNA, miRNA, and/or long ncRNA), peptides, proteins, polypeptides, metals, hormones, prohormones, lipids, fatty acids, metabolites, vitamins, ions, small molecules, carbohydrates, polysaccharides, proteoglycans, that are associated with and/or identified with differentiated cells obtained from and/or representative of and/or embodying the subject, the differentiated cells being differentiated from rejuvenated cells that were reprogrammed from the certain cells, and characterized as rejuvenated cells (via a reprogramming process, or expression/overexpression process); and/or One or more cellular components, such as RNA (mRNA, small RNA, miRNA, and/or long ncRNA), peptides, polypeptides, metals, hormones, prohormones, lipids, fatty acids, metabolites, vitamins, ions, small molecules, carbohydrates, polysaccharides, proteoglycans, that are associated with and/or identified with rejuvenated cells that were reprogrammed from certain cells, and characterized as the rejuvenated cells (from a reprogramming process), the certain cells being obtained from and/or representative of and/or embodying the subject; and/or One or more cellular components, such as RNA (mRNA, small RNA, miRNA, and/or long ncRNA), peptides, polypeptides, proteins, metals, hormones, prohormones, lipids, fatty acids, metabolites, vitamins, ions, small molecules, carbohydrates, polysaccharides, proteoglycans, or variations thereof, that are associated with and/or identified through a differentially represented component or differentially expressed or differentially represented gene and/or protein, the differentially represented component or differentially expressed or differentially represented gene and/or protein obtained after analyzing certain cells obtained from and/or representative of and/or embodying the subject, and comparing with rejuvenated cells, the rejuvenated cells having been reprogrammed from the certain cells, and characterized as rejuvenated cells (after a reprogramming process, or expression/overexpression process); and/or One or more cellular components, such as RNA (mRNA, small RNA, miRNA, and/or long ncRNA), peptides, polypeptides, proteins, metals, hormones, prohormones, lipids, fatty acids, metabolites, vitamins, ions, small molecules, carbohydrates, polysaccharides, proteoglycans, and variations thereof, that are associated with and/or identified through a differentially represented component, or expressed gene and/or protein, the differentially represented component or differentially expressed or differentially represented gene and/or protein obtained after analyzing certain cells obtained from and/or representative of and/or embodying the subject, and comparing with differentiated cells, the differentiated cells being differentiated from rejuvenated cells that were reprogrammed from the certain cells, and characterized as rejuvenated cells (after a reprogramming process, or expression/overexpression process); and/or One or more inhibitors, such as anti-miRNA mimics, anti-pro-inflammatory miRNA mimics, inhibitor of a pro-inflammatory miRNA, and/or variations thereof, the one or more inhibitors targeting one or some or all of the expressed mRNA and/or differentially expressed mRNA, the expressed mRNA and/or differentially expressed mRNA obtained from and/or representative of and/or embodying mRNA of the subject; and/or One or more siRNA mimics that target one or some or all of expressed mRNA and/or differentially expressed mRNA, the expressed mRNA and/or differentially expressed mRNA obtained from and/or representative of and/or embodying mRNA of the subject; and/or One or more components that increase representation of what is naturally expressed or produced by the rejuvenated cells, the one or more components selected from the group consisting of mRNA mimetics, long non-coding RNA mimetics, recombinant proteins, recombinant polypeptides and/or peptides, exosomes, metals, hormones, prohormones, lipids, fatty acids, metabolites, vitamins, ions, small molecules, carbohydrates, polysaccharides, proteoglycans, and various combinations thereof; and/or One or more inhibitors that target one or more mRNA naturally expressed by the somatic cells, the inhibitors comprising one or more of anti-miRNA mimics, anti-pro-inflammatory miRNA mimics, an inhibitor of a pro-inflammatory miRNA, and various combinations thereof; and/or One or more siRNA mimics that target one or more mRNA naturally expressed by the somatic cells, the mRNA associated with pro-senescence, pro-inflammatory response, pro-oxidative stress, and various combinations thereof.

Preferably, any form of RNA, when provided as an oligonucleotide (single stranded or double stranded), is provided by and with a cationic lipid, or liposome, and/or with a polymer-based delivery vehicle.

In one or more embodiments, the compositions and/or formulations when individualized and/or personalized, as described herein, further comprise at least a cosmetically acceptable base, a cosmetically acceptable penetration enhancer, and optionally one or more cosmetically acceptable additives.

The cosmetically acceptable base is a topical compounding base. Representative examples include, but are not limited to, VERSABASE®, PRACASIL®, OCCLUSADERM®, all registered by Professional Compounding Centers of America, Inc., Houston, Tex. The cosmetically acceptable base may include a carrier oil, and/or carrier butter. In one or more embodiments, the cosmetic compositions described herein will not include such a carrier.

The penetration enhancer improves topical adsorption of the extracts, enriched extracts, and/or components described herein. The penetration enhancer may include a pluronic lecithin organogel, and/or a liposome component, for delivery of the extracts, enriched extracts, and/or other components described above. A representative example provided with a cosmetically acceptable base includes, but is not limited to, LIPODERM®, registered by Professional Compounding Centers of America, Inc., Houston, Tex. In some embodiments, the compositions and/or formulations described herein do not include lecithin.

In one or more embodiments, the one or more cosmetically acceptable additives are selected from one or more of an antioxidant, anti-inflammatory, matrix metalloproteinase inhibitor, and various combinations thereof, for further rejuvenation of skin.

The compositions and/or formulations individualized and/or personalized, as described herein, may further comprise one or more of the following cosmetically acceptable additives: alpha-hydroxy acids (e.g., glycolic acid, lactic acid, tartaric acid, citric acid), beta-hydroxy acids (e.g., salicylic acid), hydroquinone, hyaluronic acid and/or an alternative thereof (sodium hyaluronate), retinol, copper peptide, dimethylaminoethanol, glutathione, co-enzyme Q-10 (and/or a synthetic analog thereof, such as ldebenone), one or more essential vitamins (e.g., methylcobalamin, ascorbic acid, etc.), one or more free form amino acids, acetyl-hexapeptide 3, 5, 7, betaine anhydrous, green tea, white tea, biotin.

In some embodiments, the compositions and/or formulations individualized and/or personalized, as described herein, may further comprise one or more of a colorant, fragrance, UV protectant, preservative, moisturizer, vanishing agent.

In some embodiments, the compositions and/or formulations individualized and/or personalized, as described herein, do not include gluten, casein, egg, wheat germ, paraben, butylated hydroxytoluene, and/or soy.

In one or more embodiments, at least the base and the penetration enhancer are provided in a specific ratio to provide a suitable penetration depth of the extract, enriched extract and/or components thereof.

Figure 4:
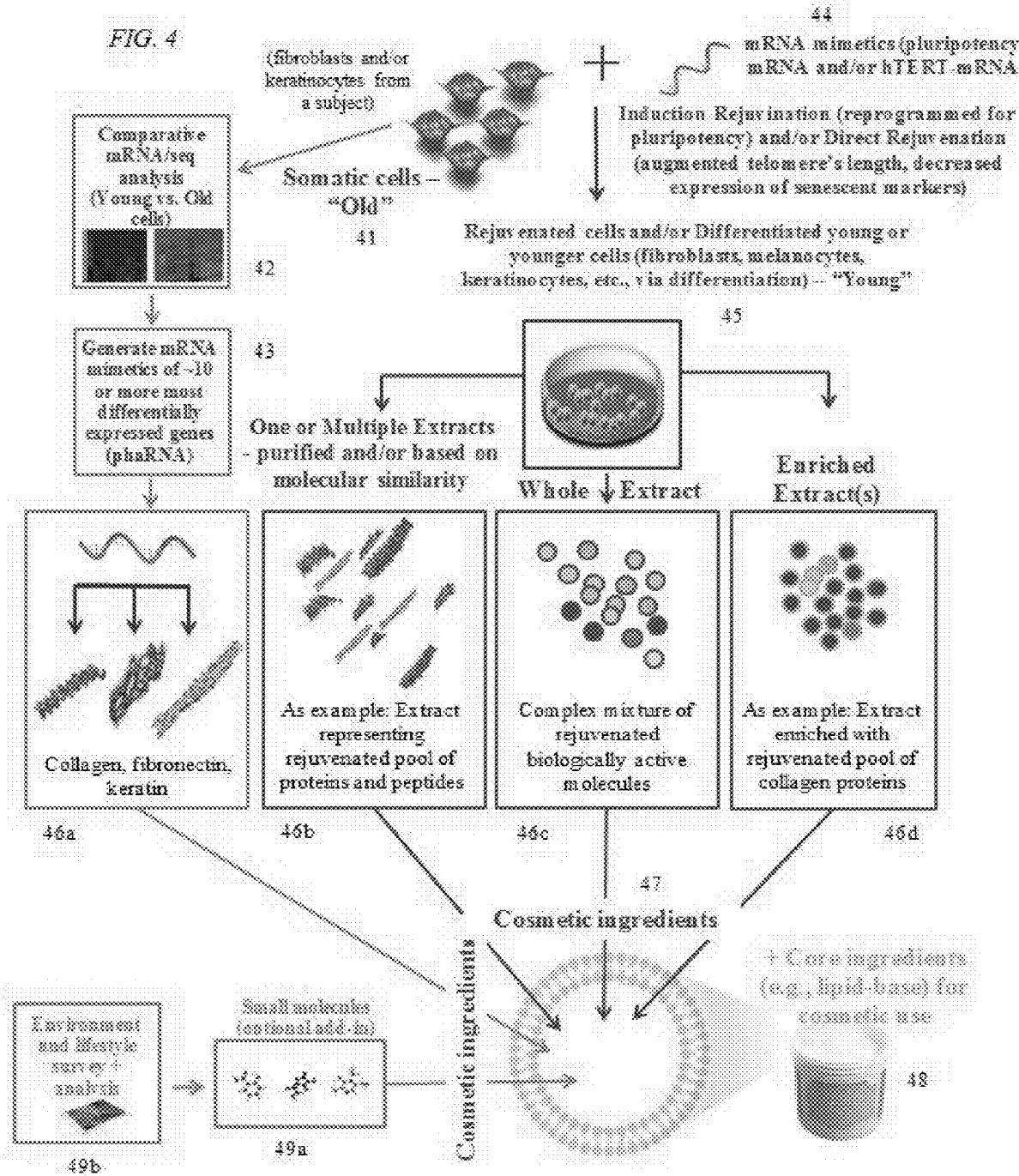
FIG. 4 depicts a fourth representative embodiment described herein.

Exemplary embodiments of compositions and/or formulations individualized and/or personalized, as described herein, are depicted in FIG. 4. Here, exemplary embodiments include ones having one or more personalized and/or individualized components provided in any one or more of block 46a (e.g. skin and/or hair proteins, synthetic or otherwise, such as those identified by differential expression as obtained via blocks 41, 42, 43), block 46b (e.g., extract of rejuvenated cells and/or differentiated young or younger cells, such as those identified from block 45), block 46c (e.g., extract of rejuvenated cells, with a mixture of one or more biologic components and/or biologically active molecules, which may include at least one component and/or biologically active molecule identified in and/or differentiated young or younger cells, such as those identified from block 45, and/or may include at least one component and/or biologically active molecule identified in differentially expressed rejuvenated cells and/or differentiated young or younger cells, when compared with sample or original cells of block 41), and block 46d (e.g., enriched extract from rejuvenated cells and/or differentiated young or younger cells). Personalized and/or individualized components of any one or more of blocks 46a, 46b, 46c, and 46d are included and/or compounded with core cosmetic ingredients (e.g., the cosmetically acceptable base and the cosmetically acceptable penetration enhancer) in block 47, to provide the cosmetic compositions and/or formulations of block 48. In addition, one or more cosmetically acceptable additives and/or small molecules of block 49a may also be included and/or compounded therein to provide the compositions and/or formulations of block 48. And, whether or not one or more cosmetically acceptable additives and/or small molecules of block 49b are included, additional cosmetically acceptable additive(s) may be selected for when preparing the individualized and/or personalized cosmetic compositions and/or formulations, these additives of block 49b being selected for and/or based on one or more personalized surveys performed by an individual. The individual performing the survey may or may not be the same individual (subject) from which the sample cells (old or original cells) of block 41 were obtained. In some embodiments, the individual performing the survey is the subject from which the sample cells (old or original cells) of block 41 were obtained. In some embodiments, the individual performing the survey is the representative of and/or embodies the subject from which the sample cells (old or original cells) of block 41 were obtained.

Any of the personalized and/or individualized compositions and/or formulations may be stored as digital data in a storage device, which may or may not be the same storage device storing information and/or data about the subject, and/or information and/or data about the rejuvenated cells, and/or about the pluripotent cells or iPSCs, and/or information and/or data about the differentiated young or younger cells, and/or information and/or data about any comparison thereof.

Figure 5:
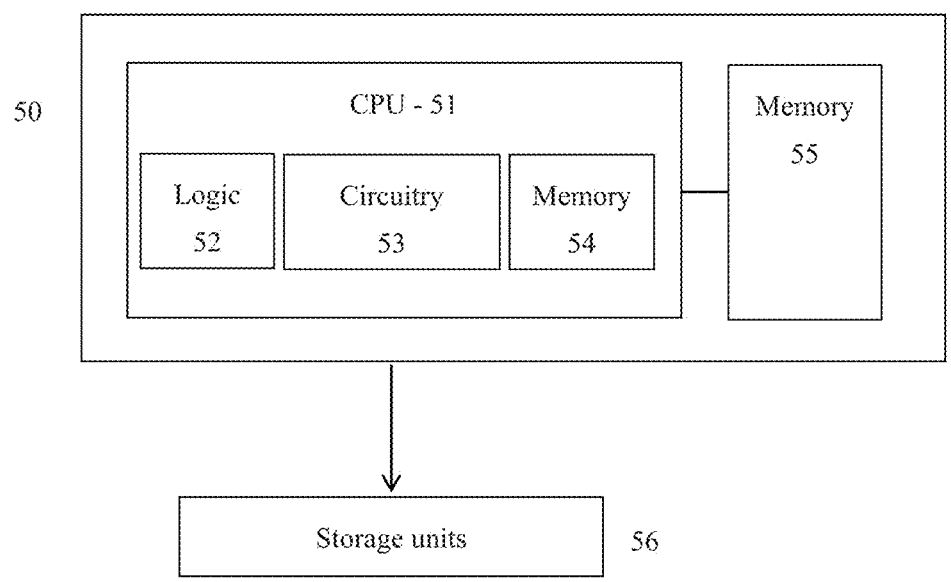
FIG. 5 depicts a portion of a system described herein.

Any of the data described here may be processed and/or accessed by one or more suitable computing devices 50, such as the type having a central processing unit 51 comprising logic 52, control circuitry 53, and memory 54 (e.g., volatile memory, cache memory) in addition to storage space or memory 55 (e.g., non-volatile memory), as depicted in FIG. 5. The computing device may be any form (e.g., desktop computer form, portable computing form, smartphone, personal computer, laptop, electronic tablet device, global positioning system (GPS) receiver, portable media player, personal digital assistant (PDAs), and/or network access device), including any processing device capable of receiving and transmitting data. Such a computing device for accessing and/or analyzing the data (e.g., about the subject, and/or information and/or data about the rejuvenated cells, and/or information and/or data about the differentiated young or younger cells, and/or information and/or data about any comparison thereof) may be the same device that stores such data (thereby, having a computer readable medium), or may be a different device. The computing device will include at least one processor, and may or may not include a telephonic portion (and associated radios/receivers), and may or may not have touch screen display for accessing some or all of the data, and/or a keyboard for accessing some or all of the data. The memory 55 will at least store some or all of the data described herein (e.g., about the subject, and/or information and/or data about the rejuvenated cells and/or information and/or data about the differentiated young or younger cells, and/or information and/or data about any comparison thereof), and may also store data associated with one or more application programs (for tables, graphics, pictures, and/or videos, and generally including a browser), and may further comprise memory to store data of a telephonic portion (e.g., contacts, phone numbers). The computing device may include and/or be associated with a camera (e.g., front facing camera or rear camera, or both) for taking pictures and video of the subject, of the sample obtained therefrom, and/or of any of the cells, and/or any analytics obtained therefrom. A user should be able to interface with at least one computing device 50, such as when there is a plurality of computing devices in a system.

The data described herein (e.g., about the subject, and/or information and/or data about the rejuvenated cells, and/or information and/or data about the differentiated young or younger cells, and/or information and/or data about any comparison thereof, which may include one or more of tables, graphics, pictures, and/or videos) may be accessed by software (e.g., a binary, machine-executable version) that is stored on at least one of the computing devices 50 in the memory 55 (e.g., RAM) and/or in the memory 54 (e.g., cache memory), and/or is stored on one or more alternative storage units 56 (e.g., hard disk, magnetic disk, tape, or CD-ROM, one or more servers) and accessible by at least one of the computing devices 50. As a further example, code or the software may be accessible and/or transmitted via wires, radio waves, cloud computing, and/or through a network such as the Internet.

A computer-implemented or computer-executable version or computer program product of any of the compositions and/or formulations described herein, and/or any methods described herein may be embodied using, stored on, and/or associated with a computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or certain RAM. Transmission media may include coaxial cables, copper wire, fiber optic lines, and wires arranged in a bus. Transmission media may also take the form of electromagnetic, radio frequency, acoustic, or light waves, such as those generated during data communications, such as radio wave, and/or infrared data communications.

For one or more formulations and/or compositions and/or methods described herein in which data from and/or about the sample, or cells thereof, or components thereof, is transmitted, analyzed, compared, and/or stored, and/or in which information about a subject is transmitted, analyzed, compared, and/or stored, a method may comprise:
 providing a sample containing cells from the subject or a representative of the subject;
 reprogramming the cells from the subject or a representative of the subject, the cells from the subject or a representative of the subject reprogrammed as rejuvenated cells;
 obtaining an extract from the rejuvenated cells; and
 providing the extract to the cosmetic formulation.

For one or more formulations and/or compositions and/or methods described herein in which data from and/or about the sample, or cells thereof, or components thereof, is transmitted, analyzed, compared, and/or stored, and/or in which information about a subject is transmitted, analyzed, compared, and/or stored, a method may comprise a method of preparing a cosmetic formulation customized for a subject, the method comprising:
 providing a sample containing cells from the subject or a representative of the subject;
 reprogramming the cells from the subject or a representative of the subject, the cells from the subject or a representative of the subject reprogrammed as rejuvenated cells;
 inducing differentiation of the rejuvenated cells to provide differentiated cells;
 obtaining an extract from the differentiated cells; and
 providing the extract to the cosmetic formulation.

In any of the methods, the method may further comprise providing at least a cosmetically acceptable base, a cosmetically acceptable penetration enhancer, and optionally one or more cosmetically acceptable additives to the cosmetic formulation.

In any of the methods, the method may further comprise a method wherein at least one of the one or more cosmetically acceptable additives selected in accordance with input from the subject or a representative of the subject regarding one or more of lifestyle of the subject, stress of the subject, sun exposure of the subject, geographic residence of the subject, skin type of the subject, diet of the subject, and exercise of the subject.

In any of the methods, the method may further comprise providing one or more cosmetically acceptable additives in the cosmetic formulation, at least one of the one or more cosmetically acceptable additives being selected by the subject.

In any of the methods, the method may further comprise a method in which the extract is a whole cell extract from the rejuvenated cells.

In any of the methods, the method may further comprise a method in which the extract is an enriched extract from the rejuvenated cells, the enriched extract having been enriched for at least one component naturally expressed or produced by the rejuvenated cells, the at least one component selected from the group consisting of protein, peptide, mRNA, microRNA, long non-coding RNA, exosomes, and various combinations thereof.

In any of the methods, the method may further comprise a method in which the extract is a whole cell extract from cells differentiated from the rejuvenated cells.

In any of the methods, the method may further comprise a method in which the extract is an enriched extract from cells differentiated from the rejuvenated cells, the enriched extract having been enriched for at least one component naturally expressed or produced by the rejuvenated cells, the at least one component selected from the group consisting of protein, peptide, mRNA, microRNA, long non-coding RNA, exosomes, and various combinations thereof.

For one or more formulations and/or compositions and/or methods described herein in which data from and/or about the sample, or cells thereof, or components thereof, is transmitted, analyzed, compared, and/or stored, and/or in which information about a subject is transmitted, analyzed, compared, and/or stored, the one or more formulations and/or compositions and/or methods will often include and/or operate in a system comprising one or more computer devices 50 used to execute software accessible by and/or associated with the one or more computing devices 50, which will be involved in implementing one or more of the embodiments and/or steps of the embodiments described herein.

In one or more embodiments, a computer system includes a computing device 50, which may include a monitor, touch-screen (user or interface display) and/or keyboard, and one or more storage units 56. In some embodiments, the computer system may include any of: a monitor, screen, keyboard or other user input device and/or interface, a mouse, and/or a pointing device. In some embodiments, the computer system includes one or more of a smartphone, personal computer, laptop, electronic tablet device, global positioning system (GPS) receiver, portable media player, personal digital assistant (PDA), a network access device, and a processing device capable of receiving or transmitting data. A computer system may further include subsystems such as: one or more central processors, system memory (volatile and/or nonvolatile), input/output (I/O) controller, display adapter, serial or universal serial bus (USB) port, one or more network interfaces, and camera, and/or speaker. Additional or fewer subsystems may be included. The system may be a multiprocessor system. The processor of computing device 50 may comprise and/or be associated with multiple processors, or a multicore processor, which may permit parallel processing of information described herein. Other configurations of subsystems suitable for use with the embodiments described herein will be readily apparent to one of ordinary skill in the art. Suitable operating systems may be from a Microsoft WINDOWS® family from Microsoft Corporation (e.g., Windows 95, 98, Me, Windows NT, Windows 2000, Windows XP, Windows XP x64 Edition, Windows Vista, Windows 7, Windows 8, Windows CE, Windows Mobile, Windows RT), or from any one of Symbian OS, Tizen, Linux, HP-UX, UNIX, Sun OS, Solaris, Mac OS X, Apple iOS, Android, Alpha OS, AIX, IRIX32, or IRIX64, as non-limiting examples.

It is further noted that any computer software product may be written in any suitable programming language, such as but not limited to C, C++, C#, Pascal, Fortran, Perl, Matlab (from MathWorks, www.mathworks.com), SAS, SPSS, JavaScript, AJAX, Java, Erlang, and Ruby on Rails. The computer software product may be an independent application with data input and data display modules. In addition, or as an alternative the computer software product may also be component software (e.g., such as Java Beans (Sun Microsystems), or Enterprise Java Beans (Sun Microsystems)).

In one or more embodiments, the computer system, comprising one or more computing devices 50 as described herein, is connected to a network. The computer system may interface with other computers using the network, including one or more computers that capture at least some of the data associated with the cells and/or their components, and/or one or more computers that capture at least some of the information from and/or associated with the subject (e.g., IT system). The network may be an intranet, internet, or the Internet, as examples. The network may be a wired network, telephone network, packet network, and/or optical network (e.g., using optical fiber). In addition, or as an alternative, the network may be a wireless network. As an example, the network may be a wireless network using a protocol such as Wi-Fi (under IEEE standard, e.g., 802.11, 802.11a, 802.11b, 802.11e, 802.11g, 802.11i, 802.11n, 802.11ac, and 802.11ad), and/or a near field communication (NFC), and/or a radio-frequency identification (RFID), and/or a mobile and/or cellular wireless communication (e.g., 2G, 3G, 4G, 3GPP LTE, WiMAX, LTE, LTE Advanced, Flash-OFDM, HIPERMAN, iBurst, EDGE Evolution, UMTS, UMTS-TDD, 1×RDD, and EV-DO).

In at least one embodiment, the IT system is or includes a computer system having a workstation operable with and executing a web browser that is accessible to the computer system on the World Wide Web (WWW or web) through the Internet. The web browser provides web pages and content thereon in suitable formats (e.g., HTML, XML, text, PDF, postscript). The web browser allows data to be downloaded from the web pages, and may be used to upload other data, which may be accessible to other parts of the system, such as by hypertext transfer protocol (HTTP) for transferring files on the web. Examples of web browsers include, but are not limited to Internet Explorer (provided by Microsoft Corporation), Firefox (provided by Mozilla), Chrome (provided by Google), Safari (provided by Apple, Inc.).

A user, who may be a subject, as described herein, a manufacturer, a distributor, and the like, will access the IT system through either or both a local application, and a web-based application, generally provided by one or more servers, generally using a network connection with the one or more servers, in which the local application and/or the web-based application may be loaded and accessible in a web browser. The local application may be on the hard drive or a disk, as examples. In some embodiments, the local application may be updated (e.g., periodically or on demand) via a direct internet upgrade linking mechanism, or through an applications storehouse (e.g., Apple iTunes and App store, Google Play store, Windows Phone App store, etc.). In some embodiments, the web-based application may be associated with a cloud infrastructure, relying on a virtual desktop, and having accessible software associated with the system stored remotely on one or more remote storage units 56. The cloud infrastructure may comprise any of a number of suitable platforms (e.g., software as a service (SaaS), platform as a service (PaaS), infrastructure as a service (IaaS), combinations, and/or improvements thereof. Examples of cloud computing services are Google Drive, Apple iCloud, Microsoft OneDrive, Microsoft Office Online, Amazon Cloud Drive, that may be adapted to a system described herein. Certain computing devices may also be included with the IT system described herein, in which the device is considered cloud-centric. An example is Chromebook, or Chromebit, by Google.

One or more servers may be associated with the one or more computing devices 50 of the IT system. The one or more servers may include a client system operably coupled with and/or in communication with the network (e.g., via an access provider, and/or a server system). The client system(s) typically request information from the server system, which provides the information. In some embodiments, a computer system may act as both a client system and a server system depending on whether the computer system is requesting or providing information, and/or may act as a stand-alone computer system. In some embodiments, the computer system may include a cloud infrastructure. In some embodiments, the computer system may include virtualization.

Figure 6:
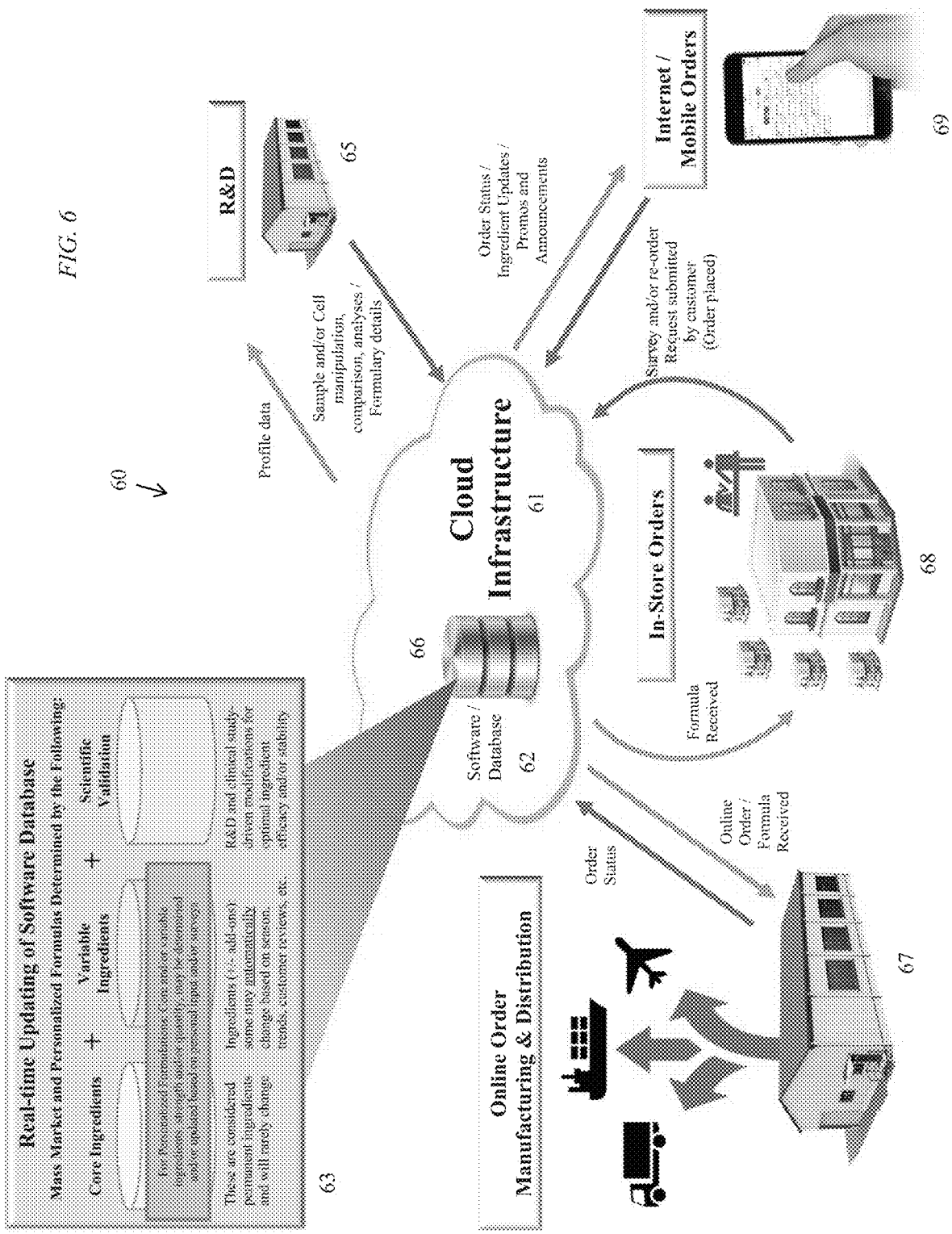
FIG. 6 depicts a representative information technology (IT) system described herein.

A representative IT system 60 is depicted in FIG. 6, which includes a cloud infrastructure 61 and one or more databases 62 associated with one or more storage units 66 on which data is provided and/or accessed and/or shared and/or stored, said data and the cloud infrastructure being in communication with and accessible by one or more computer systems (65, 67, 68, 69). The data will include information about compositions and formulations described herein, as well as about one or more samples described herein, the cells thereof, the components thereof, and/or the sample subjects. Data may also include data from and/or about a customer, including input from a survey, and/or queries from a customer, and/or requests from a customer. The customer may be an individual for whom the composition is to be provided to. The computer system from and to which the data is accessible may include a computing device 69, which may be mobile or portable or stationary. The computer system from and to which the data is accessible may include a retail store 68, the retail store having at least one computing device, which may be mobile or portable or stationary. The computer system from and to which the data is accessible may include a manufacturer and/or distributor 67, the manufacturer and/or distributor having at least one computing device, which may be mobile or portable or stationary. The computer system from and to which the data is accessible may include a research and development unit 65, having at least one computing device, which may be mobile or portable or stationary. In some embodiments, the research and development unit 65 may be associated with or may be the manufacturer and/or distributer 67. In some embodiments, the manufacturer and/or distributer 67 may comprise separate entities, one being a manufacturer, and one being a distributor.

At least some of the software associated with the IT system 60 and accessible by the one or more computer systems (65, 67, 68, 69) will include customized and/or inventive applications, such as ones identified in block 63 of FIG. 6. The customized and/or inventive software may be utilized to: (i) prepare one or more personalized compositions and/or formulations thereof; and/or (ii) modify strength and/or quantity of one or more personalized compositions and/or formulations thereof, which may or may not be based on personalized input/feedback, and/or seasons/trends, and/or scientific analysis/clinical study; and/or (iii) update one or more components of one or more personalized compositions and/or formulations thereof, which may or may not be based on personalized input/feedback, and/or seasons/trends, and/or scientific analysis/clinical study; and/or (iv) optimize one or more components of one or more personalized compositions and/or formulations thereof, which may or may not be based on personalized input/feedback, and/or seasons/ trends, and/or scientific analysis/clinical study access. The customized and/or inventive software may also be utilized to: (a) obtain, analyze, compare, store, and/or organize information about a customer (for whom there is or will be at least one personalized and/or customized composition and/or formulation); (b) obtain, analyze, compare, store, and/or organize information about one or more samples and/or cells and/or components therefrom, in which the one or more samples are from the customer, or are representative of and/or an embodiment of the customer; (c) obtain, analyze, compare, store, and/or organize information about one or more subjects from whom a sample has been obtained, in which the subject is the customer, or is representative of and/or an embodiment of the customer.

In one or more embodiments, information may be continually added into the IT system 60. The information that is added may be from a customer (e.g., via computer systems 68, 69, such as to update and/or alter at least one personalized composition described herein and/or a formulation thereof, to modify an order comprising at least one personalized composition described herein). The information that is added may be from a distributor (e.g., via computer system 67, such as to update and/or modify an order). The information that is added may be from a manufacturer (e.g., via computer system 67, such as to update and/or alter at least one personalized composition described herein and/or a formulation thereof and/or packaging thereof). The information that is added may be from a research and development facility (e.g., via computer system 65, such as to update and/or alter at least one personalized composition described herein and/or a formulation thereof). From such information, the system may be utilized to generate a highly responsive means and process for continuously creating new, personalized and customized cosmetic formulations, which are not only responsive to changes in individual or personalized needs, but to changes in market trends, seasons, clinical analyses, and/or regulations. From such information, data (e.g., preferences, best averages, trends, regulatory, scientific, etc.) may be utilized to provide cosmetic formulations that evolve, in real-time and/or on-demand, and in synchrony with such changes, and may be utilized to generate and provide group types and/or group profiles (e.g., one or more cosmeceutical lines) for one or more environments, physiology, geography, etc. In addition or alternatively, from such information, formulations may be optimized in view of data obtained regarding, e.g., the most popular additives, the least popular additives, efficacy, adverse effects, etc., in which such data is obtained over a period of time (short, long, any desired period, or at any time).

Figure 7:
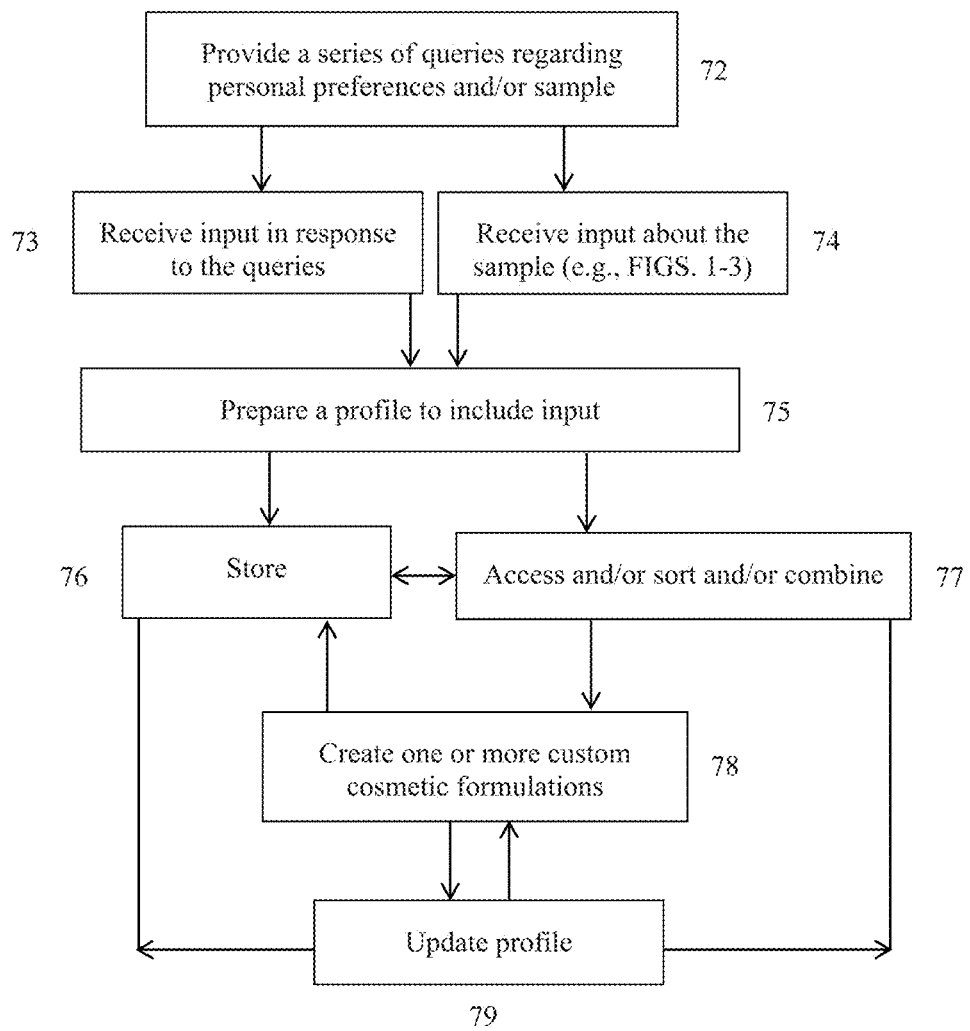
FIG. 7 depicts a first representative embodiment of utilizing the system described herein.

In a first representative embodiment of utilizing the system, a method may include providing a series of queries regarding personal skin care preferences as depicted in FIG. 7 (block 72). The queries may include a series of questions about one's skin and/or hair. The queries may include questions about a sample that is provided, in which the sample include cells, and the sample is from skin and/or hair, and is provided in the manner described previously. Input regarding and/or in response to the queries is provided in block 73. Input regarding the sample is provided in block 74. From the input, a profile is prepared in block 75. Thus, the profile may include the input in response to the queries. In addition, the profile may include information about the sample obtained as described above, and/or as depicted in any of FIGS. 1-3. The profile provides all such information as digital data, to create a unique, personalized profile. The profile may be stored (block 76). In addition, or as an alternative, information as digital data in the profile may be accessed, sorted, and/or combined with other information (e.g., from another sample in a same group, or be combined to form a group, etc.) as depicted in block 77. In this manner, personalized information about each customer of the system, about each sample obtained from the customer, or about each sample representative of the consumer, may be provided to the system. Such information may then be utilized to provide at least one customized, personalized skin care formulation for each customer (block 78). Accordingly, with the system described herein, for each customer, a profile is created that describes, in detail, information about the customer, compositional information about their skin, compositional information about a sample obtained from and/or representative of the customer, and about additional selections made by the customer (e.g., selections such as fragrance, type of skin care product, SPF protection, product size, other requested additives, or add-ons, etc.). In addition to the compositional information (scientific information about their sample, or the representative sample), and the personal preferences and/or selections, the profile will further comprise specific ingredients in the formulation, strength and amount/quantity of the ingredients in the formulation. Such information allows any formulation to be formulated and/or re-tabulated in terms of strength and/or quantity when the ingredients are provided in a different formulation (e.g., from cream to lotion, or on-demand), and/or with addition of one or more seasonal ingredients and/or seasonal adjustments to such ingredients (e.g., higher concentrations of SPF in summer and/or in southern climates), and/or with addition of one or more geographic ingredients and/or geographic adjustments to such ingredients. Moreover, the profile may be updated at any time (block 79). In one embodiment, the profile is updated by providing, periodically, an additional set of queries to the customer, and from these, new input from such queries is provided and included in the profile. Such new input may be used to update the profile and/or replace a portion of information in the profile. The profile may also be updated by the system, such as when an improvement to one or more of the additives, or base formulation, is made, and/or when there is a new regulation regarding one or more of the components/additives in the formulation, and/or when additional testing of a sample or cell thereof is performed or requested. The profile may also be updated by the customer or the system, on request, such as when a new ingredient is available or in trend, and/or is removed on request by the customer, and/or by the system. The profile may be updated by the customer by providing a sample or another sample, in which the profile will include, when requested, only the updated information about the sample (or cells, or components thereof), so that any previous information is replaced with the updated information. Any of the information provided in the process of FIG. 7 will be stored, such as in a cloud-based infrastructure, and will be accessible and communicable through the system, such as from one or more of a store, website, mobile application, research and development unit or laboratory, and manufacturing and/or distribution facility. In some embodiments, at least some of the information provided to the system and/or uploaded to the cloud will change every time there is an input, a customer request, or an order submitted into the system.

In one or more embodiments, a customer may order a cosmetic composition utilizing a system described herein, such as the system of FIG. 6. An order may be fulfilled quickly, competitively, and on demand.

In one or more embodiments, a line of customized cosmetic compositions based on the sample data provided by one or more customers, and on personal information provided by one or more customers may be provided utilizing a system described herein, such as the system of FIG. 6. For example, information stored as digital data in the one or more databases 62 of FIG. 6 may be sorted to form a group (e.g., by age, location, ethnicity, and/or diet, etc.); and the sorted information, in addition to sample information provided by one or more samples representative of the group, may be utilized to prepare one or more formulations for the group. In addition, any of the compositions and formulations described herein, and/or the line of customized cosmetic compositions for the group, may be updated and/or changed at any time, such as in view of one or more seasonal ingredients, trends, newer ingredients, best averages, best ingredients, etc. Accordingly, any customized cosmetic composition, and/or line of customized cosmetic compositions, may constantly change and/or adapt with data provided to the system to allow such customized cosmetic composition, and/or line of customized cosmetic compositions to remain effective and/or adaptable with new market trends, preferences, and/or regulatory changes. This prevents stagnation of a cosmetic product line, and provides fast moving new lines of products, that remain personalized and/or customized for a customer (type and/or profile) and/or a group of customers (group type and/or group profile).

Figure 8:
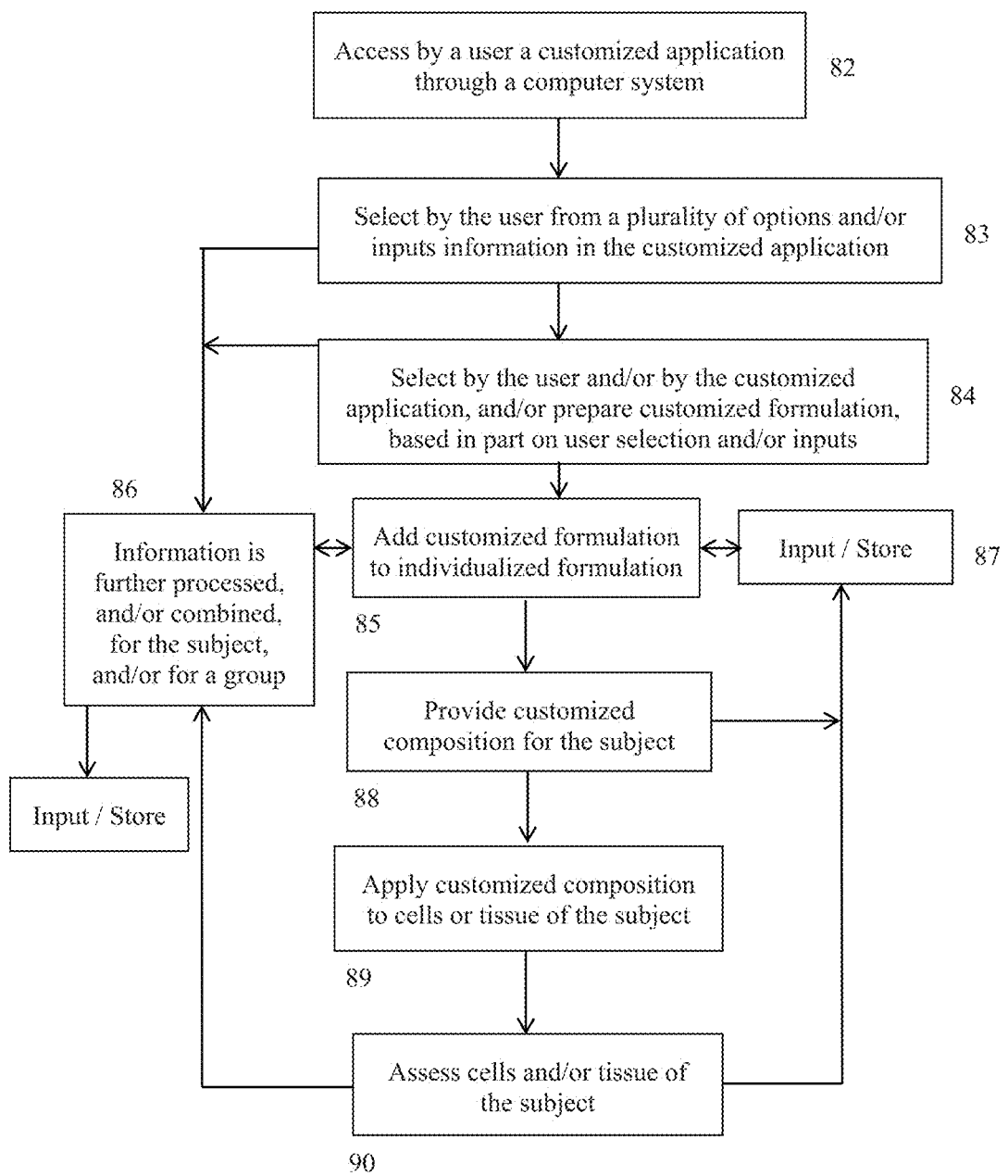
FIG. 8 depicts another representative embodiment of utilizing a system described herein.

In at least one embodiment, a customer may utilize the system described herein as depicted in FIG. 8, in which a user, such as a customer (who may or may not be the subject providing a sample), accesses a local application or a web browser application executed on either the computer system and/or the client system(s), as depicted block 82. The application is accessible by the computing device and is stored on the one or more servers, the client system(s), and or locally, as was described above. From the application, the user selects from a plurality of options provided in the application (e.g., from a drop down menu), and/or inputs information in response to a plurality of queries provided in one or more entry locations with the application, as depicted in block 83. In one or more embodiments, the user selection and/or input is in response to a plurality of questions about the subject, such as lifestyle, stress level, sun exposure, geographic residence, skin type, diet and/or diet restrictions, and/or exercise schedule, the questions provided by the application either sequentially, and/or simultaneously, and/or on one or more web pages that may be navigated to through the application. Based on the user selection and/or input, a customized formulation is selected by the application. In one or more embodiments, the customized formulation is selected from a plurality of already prepared customized formulations. The already prepared customized formulations will include at least one of the one or more ingredients described above. The ingredients in the already prepared customized formulation are based on ingredients associated with the user selection and/or inputs (e.g., lifestyle, stress level, sun exposure, geography, skin type, diet and/or diet restrictions, and/or exercise schedule) (block 84). For example, the already prepared customized formulations may be pre-formulated for a category type (e.g., high stress, oily skin, high sun exposure as one category, or low stress, oily skin, high sun exposure as another category, etc.). In addition, or as an alternative, such as when there is no category associated with the user selection and/or input, a customized formulation may be provided by the application, this customized formulation being based on at least one, some, or all of the user selections and/or inputs provided by the user through the application. In some embodiments the user selection and/or input is provided to a separate application, and the separate application selects from the one or more ingredients to provide and prepare the customized formulation. The customized formulation, whether already prepared or not, will include the one or more ingredients described above, which are included in accordance with the user selection and/or input. The customized formulation being selected by the application (or by the individual and/or separate application) is further provided to a cosmetic formulation individualized for the subject, and comprising the extract, enriched extract, and/or components thereof, as depicted in block 85. The cosmetic formulation personalized for the subject (e.g., comprising the extract, enriched extract, and/or components thereof) is formulated in accordance with the above description, and/or as outlined in any of FIGS. 1-3. The providing of the cosmetic formulation (selected by the application) with the customized formulation (comprising the extract, enriched extract, and/or components thereof of the subject) may be performed by hand, by an automated process (such as by utilizing a compounding machine and/or system for compounding the one or more cosmetic applications, the machine or system receiving the data regarding the customized formulation or necessary data to prepare such a formulation, the data input by hand and/or transmitted by wire or wirelessly to one or more processors of the machine or system), or by combinations thereof, which is used to provide a customized composition for the subject (block 86). Some or all of the data and/or actual formulations may be stored (block 87). Data storing is in one or more of the servers and/or the client system. Formulation storage is in one or more suitable containers.

The user selection and/or input of block 83 may also be incorporated and/or tabulated and/or combined with other users having similar preferences, in which the users may be formed as a group. Any of the information input and/or tabulated and/or combined may be stored in one or more data files and/or look-up tables (block 87). Any of the stored data in the one or more files and/or look-up tables may be available to select and/or prepare the customized formulation of block 84. In some embodiments, a self-assessment by the user (subject assessment) may be replaced and/or accompanied by an assessment performed by a health care professional, such as a dermatologist, and such information may be provided for selection and/or preparation of the customized formulation, and/or may be stored. The preparing and/or selecting of the customized formulation may also be monitored and/or coordinated by a health care professional, and/or a dermatologist. Once the appropriate composition(s)/ingredients for the customized formulation has been selected, the formulation may be prepared at that time, and/or data stored for later preparation, the preparation of which occurs manually, and/or automatically (e.g., using an automated machine, having or containing the composition(s)/ingredients and/or one or more already prepared customized formulations). In some embodiments, the subject (and/or the healthcare professional) may further select one or more ingredients to include in the customized formulation (block 84). For example, the subject or professional may desire to add a sunscreen agent. In some embodiments, the subject (and/or the healthcare professional) may further select the form that the customized and/or personalized formulation with be provided as. For example, the subject or professional may desire that the final formulation be provided as a lotion, or as a cream. In some embodiments, the subject (and/or the healthcare professional) may further select the container that the customized and/or personalized formulation will be provided in. For example, the subject or professional may desire that the final formulation be provided in a bottle, or in a tube.

Upon providing a final formulation in any of the embodiments described herein, a method as described herein may additionally comprise providing all or some of the cosmetic composition as a final formulation to the subject (block 88). In addition, the method as described herein may additionally include applying the final formulation as a cosmetic composition to cells or tissue of the subject needing rejuvenation. The cells or tissue may be at or near the location where the sample containing the cells as described with FIG. 1, block 10 were obtained from. The final cosmetic composition may be applied at least once per day, and may be applied twice per day, or more than twice a day. The final cosmetic compositions may be applied daily (or more often) for several days, for weeks, and/or months, or more. The final dosage and time period of application and/or treatment may vary depending upon the condition of the subject, and/or the nature of the cosmetic composition applied.

In one or more embodiments, the subject may perform at least a second self-assessment after treatment with the cosmetic composition, which may be replaced and/or accompanied by a second assessment performed by a health care professional (block 90). Data about the second assessment (self-assessment and/or by a professional) may be input to the customized application described with FIG. 8. Any such data may be tabulated and/or combined and/or stored with one or more data files and/or look-up tables. The data may be the same data files and/or look-up tables used to provide the customized formulation, and/or may be different, and/or new data files and/or look-up tables. Such data may provide useful as to the performance of the cosmetic composition for the individual, and/or for a group, of which the subject may be a part of or for which the cosmetic composition has been applied to. In one or more embodiments, the subject receiving the cosmetic composition is part of a group, the subject being representative of a group for which at least a portion of the composition was provided for (which may or may not include an individualized formulation being prepared for a sample containing cells, in which the sample was representative of a group in which the subject is a part of). In some embodiments, treatment is repeated and/or extended for some period of time only after the second assessment. For example, a self-assessment and/or professional assessment may be performed after some period of applying the cosmetic composition (e.g., after one week of applying the cosmetic composition on a daily basis), and with a positive assessment (e.g., visible improvement, and/or at least no negative effects), the subject continues application of the cosmetic composition.

In one or more embodiments, the customized application described above, and associated with any of FIGS. 6-8, is provided at a store and/or in a health care professional office, for initiating selection and/or preparation of a cosmetic composition that is individualized for the subject.

In one or more embodiments, the customized application described above, and associated with any of FIGS. 6-8, is provided as an on-line store for a customer.

In one or more embodiments, the customized application described above, and associated with any of FIGS. 6-8, is accessible by any mobile device.

In one or more embodiments, the customized application described above, and associated with any of FIGS. 6-8, provides a log-in for the customer, for ordering, re-ordering, re-formulating, and/or shipping of a cosmetic composition described herein.

In one or more embodiments, the customized application described above, and associated with any of FIGS. 6-8, manages the one or more ingredients for the cosmetic compositions described herein, including inventory, and/or pricing.

In one or more embodiments, the customized application described above, and associated with any of FIGS. 6-8, provides a video and/or consultation option for consulting, and/or assessment with one or more health care professionals.

The foregoing description provides representations and examples embodying, at least in part, teachings of the invention. The invention, as defined by the appended claims, is not limited to the described embodiments. Alterations and modifications to the disclosed embodiments may be made without departing from the invention. For example, flows and methods described herein are not limited, and may have additional steps (not necessarily described herein), different steps that replace some of the steps presented, fewer steps or a subset of the steps presented, or steps in a different order than presented, or any combination of these. Further, certain steps in other implementations may not be exactly the same as the steps presented and may be modified or altered as appropriate based on the data, knowledge, and understanding, such as described herein.

The meaning of the terms used in this specification are, unless expressly stated otherwise, intended to have ordinary and customary meaning and are not intended to be limited to the details of the illustrated structures or the disclosed embodiments. Although the foregoing description of embodiments have shown, described and pointed out certain novel features of the invention, it will be understood that various omissions, substitutions, and changes in the form of the detail as illustrated as well as the uses thereof, may be made by those skilled in the art, without departing from the scope of the invention. Particularly, it will be appreciated that the one or more embodiments may manifest itself in other configurations as appropriate for the end use of the material made thereby.

Definitions

The following definitions are meant to help clarify without being limiting.

As used herein, the terms "a," "an," "the," and "said" means one or more, unless the context dictates otherwise.

As used herein, the term "about" means the stated value plus or minus a margin of error or plus or minus 10% if no method of measurement is indicated.

As used herein, the term "or" means "and/or" unless explicitly indicated to refer to alternatives only or if the alternatives are mutually exclusive.

As used herein, the phrase "cell aging" refers to one or more of: an increase in cell damage and/or loss of function and/or loss of morphology and/or loss of behaviors and/or loss of capabilities, all typically associated with chronological aging of cells in vitro or in vivo.

As used herein, the phrase "cell type" refers to a set of capabilities, behaviors, morphological features, and functions of a cell that together enable the cell to perform a specific role that can contribute to the health and function of an organism. The set of all cell types forms a continuum of types more than a set of discrete types. As a practical necessity given technological modifications of cells into types similar to but not exactly the same as natural cells, cell types also include types found in vitro or resulting from manipulation, which approximate, but do not necessarily exactly recapitulate, cell types found in vivo.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "containing," "contains," and "contain" have the same open-ended meaning as "comprising," "comprises," and "comprise," provided above.

As used herein, the terms "having," "has," and "have" have the same open-ended meaning as "comprising," "comprises," and "comprise," provided above.

As used herein, the terms "including," "includes," and "include" have the same open-ended meaning as "comprising," "comprises," and "comprise," provided above.

As used herein, the phrase "consisting of" is a closed transition term used to transition from a subject recited before the term to one or more material elements recited after the term, where the material element or elements listed after the transition term are the only material elements that make up the subject.

As used herein, the term "de-differentiation" refers to changes in a cell type to a cell type that is capable of changing into a larger number of cell types than the original cell, or changes in the cell type in the direction towards the zygote in the cell lineage tree.

As used herein, the term "differentiation" refers to changes in a cell type to a cell type that is capable of changing into a smaller number of other cell types, or a cell type that is relatively further from the zygote in the cell lineage tree compared to the starting cell type.

As used herein, the term "reprogramming" refers to changes in a cell to a different cell type, or to a cell approximating a different cell type, and is thus a broad term. Herein, reprogramming can include reprogramming to a less differentiated cell type (also called dedifferentiation), a more differentiated cell type (also called differentiation), or a cell type that is different in more ways from the original cell type than its degree of differentiation (also called transdifferentiation). Reprogramming and rejuvenation are different processes, and reprogramming may happen with or without rejuvenation.

As used herein, the term "rejuvenation" refers to reversing at least one aspect of cell aging, as defined above. Rejuvenation can happen with or without reprogramming.

As used herein, the phrase "reprogramming to a more rejuvenated (young or younger) state", or variations thereof, refer to reprogramming and rejuvenating a cell, or in other words, changing the type and age of a cell. It is emphasized that although reprogramming and rejuvenation are different processes that can occur separately, they can and do sometimes occur together. Some embodiments of the invention combine reprogramming and rejuvenation, or in other words, changing both cell type and cell age. Some embodiments involve rejuvenating more than once. Some embodiments of the invention involve rejuvenation without reprogramming.

As used herein, the term "simultaneously" means occurring at the same time or about the same time, including concurrently.

As used herein, the term "transdifferentiation" refers to changes in a cell type without necessarily differentiating or de-differentiating the cell, as defined above.

INCORPORATION BY REFERENCE

All patents and patent applications, articles, reports, and other documents cited herein are fully incorporated by reference to the extent they are not inconsistent with this invention.

What is claimed is:

1. A cosmetic formulation customized for a subject, the cosmetic formulation comprising cell-free conditioned media, wherein:
    i) the cell-free conditioned media is cell culture media in which modified rejuvenated skin cells have previously been cultured,
    ii) the modified rejuvenated skin cells are produced by transfecting skin cells obtained from the subject or a representative of the subject with:
        (a) one or more synthetic messenger RNAs (mRNA) mimetic encoding a protein selected from each of:
            (1) a telomerase reverse transcriptase (TERT) or a variant thereof,
            (2) a human sheltering complex component selected from RAP1, TIN2, TRF1, TRF2, TPP1, or POT1, and
            (3) a human aging/longevity protein selected from SIRT proteins, JunD, GDF11, or growth factor, and
        (b) one or more of miRNA 10(a), miRNA 21, miRNA-29, miRNA-146(a), miRNA-155, an anti-inflammatory miRNA, or an inhibitor of a pro-inflammatory miRNA; and
    iii) the cell-free conditioned media is substantially free of the modified skin cells or intracellular or membrane bound components of the modified skin cells.

2. The cosmetic formulation of claim 1, further comprising at least one of: a cosmetically acceptable base and a cosmetically acceptable penetration enhancer.

3. The cosmetic formulation of claim 1, further comprising one or more cosmetically acceptable additives selected from the group consisting of an antioxidant, an anti-inflammatory, a matrix metalloproteinase inhibitor, and combinations thereof.

4. The cosmetic formulation of claim 1, further comprising one or more of a colorant, a fragrance, an UV protectant, a preservative, a moisturizer, and a vanishing agent.

5. The cosmetic formulation of claim 2, wherein the cosmetically acceptable base and the cosmetically acceptable penetration enhancer are provided in various ratios to provide varying penetration depth of the cosmetic formulation.

6. The cosmetic formulation of claim 2, wherein the cosmetically acceptable penetration enhancer comprises one or more of a pluronic lecithin organogel, a lipid component, a polymeric vehicle, a microparticle, a nanoparticle, a liposome component, and combinations thereof.

7. The cosmetic formulation of claim 1, wherein the modified skin cells have increased expression of one or more proteins selected from telomerase reverse transcriptase (TERT), RAP1, TIN2, TRF1, TRF2, TPP1, POT1, SIRT, SIRT-1, SIRT-2, SIRT-3, SIRT-4, SIRT-5, SIRT-6, SIRT-7, JunD, GDF11, and growth factor.

8. A method of preparing a cosmetic formulation customized for a subject, the method comprising:
    a) culturing modified rejuvenated skin cells in a culture media to generate conditioned media, wherein the modified rejuvenated skin cells are produced by transfecting skin cells obtained from the subject or a representative of the subject with:

(i) at least one synthetic messenger RNA (mRNA) mimetic encoding a protein selected from each of:
(1) telomerase reverse transcriptase (TERT) or a variant thereof,
(2) a human shelterin complex component selected from RAP1, TIN2, TRF1, TRF2, TPP1, or POT1, and
(3) a human aging/longevity regulating protein selected from SIRT proteins, JunD, GDF11, or growth factor;
(ii) one or more of miRNA 10(a), miRNA 21, miRNA-29, miRNA-146(a), miRNA-155, an anti-inflammatory miRNA, or an inhibitor of a pro-inflammatory miRNA; and
b) obtaining a cell-free conditioned media from the conditioned media by collecting the conditioned media from the cultured modified rejuvenated skin cells and removing cells from the conditioned media, wherein the cell-free conditioned media is substantially free of the modified rejuvenated skin cells or intracellular or membrane bound components of the modified skin cells; and
c) formulating the cell-free conditioned media in a cosmetic formulation.

9. The method of claim 8, wherein the cosmetic formulation further comprises at least one of: a cosmetically acceptable base and a cosmetically acceptable penetration enhancer.

10. The method of claim 8, wherein the cosmetic formulation further comprises one or more cosmetically acceptable additives selected from the group consisting of an antioxidant, an anti-inflammatory, a matrix metalloproteinase inhibitor, and combinations thereof.

11. The method of claim 8, wherein the cosmetic formulation further comprises one or more of a colorant, a fragrance, an UV protectant, a preservative, a moisturizer, and a vanishing agent.

12. The method of claim 9, wherein the cosmetically acceptable base and the cosmetically acceptable penetration enhancer are provided in various ratios to provide varying penetration depth of the cosmetic formulation.

13. The method of claim 9, wherein the cosmetically acceptable penetration enhancer comprises one or more of a pluronic lecithin organogel, a lipid component, a polymeric vehicle, a microparticle, a nanoparticle, and a liposome component.

14. The method of claim 8, wherein the modified skin cells have increased expression of one or more proteins selected from telomerase reverse transcriptase, RAP1, TIN2, TRF1, TRF2, TPP1, POT1, SIRT, SIRT-1, SIRT-2, SIRT-3, SIRT-4, SIRT-5, SIRT-6, SIRT-7, JunD, GDF11, and growth factor.

15. The cosmetic formulation of claim 1, wherein the modified skin cells have increased expression of telomerase reverse transcriptase (TERT).

16. The cosmetic formulation of claim 1, wherein the modified skin cells have increased expression of the growth factor.

17. The cosmetic formulation of claim 1, wherein the growth factor is selected from human fibroblast growth factor (hFGF), basic hFGF (bhFGF), and human stem cell factor (hSCF).

18. The cosmetic formulation of claim 1, wherein the modified skin cells have been transfected with at least one synthetic mRNA encoding TERT.

19. The cosmetic formulation of claim 1, wherein the modified skin cells have been transfected with at least one synthetic mRNA encoding the growth factor.

20. The cosmetic formulation of claim 19, wherein the growth factor is selected from human fibroblast growth factor (hFGF), basic hFGF (bhFGF), and human stem cell factor (hSCF).

21. The cosmetic formulation of claim 1, wherein the modified skin cells have been transfected with at least two synthetic mRNAs encoding at least two growth factors.

22. The cosmetic formulation of claim 1, wherein the two growth factor are selected from human fibroblast growth factor (hFGF), basic hFGF (bhFGF), and human stem cell factor (hSCF).

23. The cosmetic formulation of claim 22, wherein the two growth factor are human fibroblast growth factor (hFGF) and basic hFGF (bhFGF).

24. The cosmetic formulation of claim 18, wherein the modified skin cells have been transfected with at least one synthetic mRNA encoding the growth factor.

25. The cosmetic formulation of claim 18, wherein the modified skin cells have been transfected with at least two synthetic mRNAs encoding at least two growth factors.

26. The cosmetic formulation of claim 25, wherein the two growth factor are human fibroblast growth factor (hFGF) and basic hFGF (bhFGF).

27. The method of claim 8, wherein the skin cells have been transfected with at least one synthetic mRNA encoding TERT.

28. The method of claim 8, wherein the skin cells have been transfected with at least one synthetic mRNA encoding the growth factor.

29. The method of claim 28, wherein the growth factor is selected from human fibroblast growth factor (hFGF), basic hFGF (bhFGF), and human stem cell factor (hSCF).

30. The method of claim 8, wherein the modified skin cells have been transfected with at least two synthetic mRNAs encoding at least two growth factors.

31. The method of claim 30, wherein the two growth factor are selected from human fibroblast growth factor (hFGF), basic hFGF (bhFGF), and human stem cell factor (hSCF).

32. A cosmetic formulation customized for a subject, the cosmetic formulation comprising cell-free conditioned media and a matrix metalloproteinase inhibitor, wherein:
i) the cell-free conditioned media is cell culture media in which modified rejuvenated skin cells have previously been cultured,
ii) the modified rejuvenated skin cells are produced by transfecting skin cells obtained from the subject or a representative of the subject with:
(a) one or more synthetic messenger RNAs (mRNA) mimetic encoding a protein selected from each of:
(1) a telomerase reverse transcriptase (TERT) or a variant thereof,
(2) a human sheltering complex component selected from RAP1, TIN2, TRF1, TRF2, TPP1, or POT1, and
(3) a human aging/longevity protein selected from SIRT proteins, JunD, GDF11, or growth factor, and
(b) one or more of miRNA 10(a), miRNA 21, miRNA-29, miRNA-146(a), miRNA-155, an anti-inflammatory miRNA, or an inhibitor of a pro-inflammatory miRNA; and iii) the cell-free conditioned media is substantially free of the modified skin cells or intracellular or membrane bound components of the modified skin cells.

\* \* \* \* \*